United States Patent [19]
Thaisrivongs et al.

[11] Patent Number: 6,150,385
[45] Date of Patent: Nov. 21, 2000

[54] 1,3,4-THIADIAZOLES USEFUL FOR THE TREATMENT OF CMV INFECTIONS

[75] Inventors: Suvit Thaisrivongs; Steven Ronald Turner, both of Kalamazoo, Mich.

[73] Assignee: Pharmacia & Upjohn Company, Kalamazoo, Mich.

[21] Appl. No.: 09/270,429

[22] Filed: Mar. 16, 1999

Related U.S. Application Data

[60] Provisional application No. 60/078,528, Mar. 19, 1998.
[51] Int. Cl.$^7$ ..................... C07D 285/135; A61K 31/433
[52] U.S. Cl. ............................................ 514/363; 548/139
[58] Field of Search .............................. 548/139; 514/363

[56] References Cited

FOREIGN PATENT DOCUMENTS

| | | | |
|---|---|---|---|
| 0 061 434A | 9/1982 | European Pat. Off. | ...... C07D 285/12 |
| 0 229 501A | 7/1987 | European Pat. Off. | .......... C12N 5/00 |
| 0 785 193A | 7/1997 | European Pat. Off. | ...... C07D 285/10 |
| WO 93/20814 | 10/1993 | WIPO | ............................ A61K 31/41 |

OTHER PUBLICATIONS chemical abstracts v.52 #11823f, 1958.
Kurzer J Chem Soc (C) 1970 (26) 1805.
Okawara, T, et al., "A New Route to 1,2,4–Triazoles and 1,3,4–Thiadiazoles from 1–Acylbithiourea," J. Heterocyclic Chem., 25:1071–1075 (1988).
F. Kurzer, "Heterocyclic Compounds from Urea Derivatives. Part XXI. Adducts from Thiocarbonohydrazides and Aroyl Isothiocyanates and Their Cyclisation," J. Chem. Soc. (C), 2932–2938 (1971).
F. Kurzer, "Heterocyclic Compounds from Urea Derivatives. Part XVIII. Adducts from Aminoguanidines and Aroyl Isothiocyanates and Their Cyclisation, " J. Chem. Soc. (C), 1805–1813 (1970).
F. Kurzer, "Heterocyclic Compounds from Urea Derivatives. Part XIX. Adducts from Diaminoguanidines and Aroyl Isothiocyanates and Their Cyclisation," J. Chem. Soc. (C), 13:1813–1823 (1970).
"Production of 2–acylamino–1,3,4–thiadiazole derivs.—by reacting n–acylimino:carbonic acid ester(s) with thiosemicarbazide or di:thiocarbazinic acid ester(s)" Derwent Abstracts 07484C/05.
"*Anti–inflammatory composition containing 1,3,4–thiadiazole derivatives as active agent*," Derwent Abstracts 46012X/24.
Patent Abstracts of Japan—vol. 199, No. 510; JP 07 188017 A, Jul. 25, 1995.
Patent Abstracts of Japan—vol. 199, No. 509, JP 07 149748 A, Jun. 13, 1995.

*Primary Examiner*—Robert Gerstl
*Attorney, Agent, or Firm*—Lucy X. Yang

[57] ABSTRACT

The present invention presents novel 1,3,4-thiadiazole derivatives of formula I

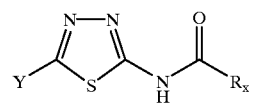

which have useful antiviral activity against herpes virus, cytomegalovirus (CMV).

14 Claims, No Drawings

1,3,4-THIADIAZOLES USEFUL FOR THE TREATMENT OF CMV INFECTIONS

CROSS-REFERENCE TO RELATED APPLICATIONS

This application claims the benefit of provisional application U.S. Ser. No. 60/078,528, filed Mar. 19, 1998, under 35 USC 119(e)(i).

BACKGROUND OF THE INVENTION

The present invention relates to novel 1,3,4-thiadiazole derivatives having useful antiviral activity against herpes virus, cytomegalovirus (CMV). The invention also relates to a pharmaceutical composition containing such compounds and methods for the treatment of such viral infections. Many of these compounds are also active against other herpes viruses, such as the varicella zoster virus, the Epstein-Barr virus, the herpes simplex virus, and the human herpes virus type 8 (HHV-8).

INFORMATION DISCLOSURE

Derwent Abstracts 07484C/05 discloses 2-acylamino-1, 3,4-thiadiazole derivatives useful as pesticides, optical brightening agents, and intermediates for pharmaceuticals.

Derwent Abstracts 46012X/24 discloses anti-inflammatory composition containing 1,3,4-thiadiazoles derivatives as active agents.

J. Chem. Soc. (C), Vol. 13, 1813–1823, (1970) describes addition-cyclisation reactions undergone by aroyl isothiocyanates with NN'-diaminoguanidines.

J. Heterocyclic Chem. Vol. 25, 1071–1074 describes a new route to 1,2,4-triazoles and 1,3,4-thiadiazoles from 1-acylbithiourea.

SUMMARY OF THE INVENTION

The present invention provides a compound of formula I

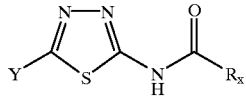

I or pharmaceutically acceptable salts thereof wherein:

Y is
  a) —$NHR_1$, or
  b)
  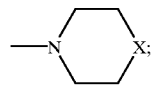

X is —O—, —S(=O)$_h$—, —$CH_2$—, or —$NR_2$—;

$R_1$ is
  a) $C_{1-18}$ alkyl,
  b) —$(CH_2)_i$—$C_{3-7}$ cycloalkyl,
  c) —$(CH_2)_i$-bicycloalkyl,
  d) —$(CH_2)_j$-M,
  e) —$(CH_2)_j$-W,
  f) —$(CH_2)_k$ aryl, wherein aryl may be substituted with one to three $R_3$,
  g) —$(CH_2)_k$-het, wherein het may be substituted with one to three $R_3$,
  h) —$(CH_2)_k$-Q, wherein Q may be substituted with one to three $R_3$, or
  i) H;

$R_2$ is
  a) H,
  b) $C_{1-4}$ alkyl,
  c) —C(=O)$C_{1-4}$ alkyl,
  d) —S(=O)$C_{1-4}$ alkyl,
  e) —$CO_2C_{1-4}$ alkyl, or
  f) —$CO_2CH_2$phenyl;

$R_3$ is
  a) halo,
  b) $C_{1-4}$ alkyl,
  c) $C_{1-4}$ alkoxy,
  d) benzyl,
  e) —CN,
  f) —$SO_2F$,
  g) —$SO_2NH_2$,
  h) —$CF_3$,
  i) —$NO_2$,
  j) —$OCH_2O$—,
  k) —$CO_2(C_{1-4}$ alkyl),
  l) —C(=O)$C_{l-4}$ alkyl,
  m) —C(=O)$NH_2$,
  n) —$NHCO_2(C_{1-4}$ alkyl), or
  o) —C(=O)—O—C(=O)—;

M is
  a) —CN
  b) halo,
  c) —$CO_2C_{1-4}$ alkyl,
  d) —CH(phenyl)$_2$, e)
  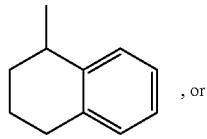
  , or f)
  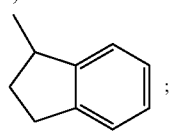
  ;

W is
  a) —$OR_4$,
  b) —$SR_4$,
  c) —$NHR_5$, or
  d) —$NR_6R_7$;

$R_4$ is
  a) $C_{1-4}$ alkyl,
  b) $C_{3-7}$ cycloalkyl, or
  c) aryl, $R_5$ is
  a) $C_{1-7}$ alkyl,
  b) $C_{3-7}$ cycloalkyl,
  c) aryl, or
  d) —C(=O)$C_{1-4}$ alkyl;

$R_6$ and $R_7$ are independently
  a) $C_{1-4}$ alkyl, or
  b) $R_6$ and $R_7$ together with nitrogen form a 4- to 6-membered saturated heterocyclic moiety having one to two atoms selected from the group consisting of oxygen, nitrogen, and sulfur;

$R_x$ is
  a) $C_{1-18}$ alkyl,
  b) $C_{2-18}$ alkenyl,
  c) $C_{2-18}$ alkynyl,
  d) $C_{2-6}$ alkyl substituted with one to three halo, $C_{1-3}$ alkoxy, —OH, —SH, or —$CO_2H$,
  e) $C_{2-6}$ alkenyl substituted with aryl, wherein the aryl may be in turn substituted with one to three $R_2$,
  f) —$(CH_2)_i$-aryl, wherein aryl may be substituted with one to three $R_3$,
  g) —$(CH_2)_i$-Q, wherein Q may be substituted with one to three $R_3$, or
  h) —$(CH_2)_i$-U, wherein U may be substituted with one to three $R_3$;

aryl is phenyl or naphthyl;

het is 5- to 10-membered unsaturated heterocyclic moiety having one to three atoms selected from the group consisting of oxygen, nitrogen, and sulfur;

U is 5- to 9-membered unsaturated heterocyclic moiety having one to three atoms selected from the group consisting of oxygen, nitrogen, and sulfur;

Q is 5- or 6-membered saturated heterocyclic moiety having one to two atoms selected from the group consisting of oxygen, nitrogen, and sulfur, wherein nitrogen atom may be in turn substituted with $C_{1-4}$ alkyl, phenyl, benzyl, —C(=O)$C_{1-4}$ alkyl, or —$CO_2C_{1-4}$ alkyl;

h is 0, 1, or 2; i is 0, 1, 2, 3, or 4; j is 2, 3, or 4; k is 0, 1, 2, 3, 4, 5, or 6;

and with the following provisos:
  a) where $R_3$ is phenyl or 4-methoxyphenyl, $R_1$ is other than phenyl, 4-methoxyphenyl, or 4-chlorophenyl;
  b) where $R_3$ is —$CH_2$phenyl, $R_1$ is other than phenyl or —$CH_2$phenyl;
  c) where $R_3$ is H, substituted or unsubstituted alkyl or phenyl, $R_1$ is other than unsubstituted alkyl or phenyl.

The compounds of the present invention have antiviral activity against cytomegalovirus (CMV), a member of herpes virus.

DETAILED DESCRIPTION OF THE INVENTION

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive. Thus, $C_{1-4}$ alkyl refers to alkyl of one to four carbon atoms, inclusive, or methyl, ethyl, propyl, butyl, and isomeric forms such as, for example, straight and branched form thereof.

The terms "$C_{1-4}$ alkyl", and "$C_{1-18}$ alkyl" refer to an alkyl group having one to four, or one to eighteen carbon atoms respectively such as, for example, methyl, ethyl, propyl, butyl, pentyl, hexyl, heptyl, octyl, nonyl, decyl, undecyl, dodecyl, tridecyl, tetradecyl and their isomeric forms thereof.

The terms "$C_{2-18}$ alkenyl" refers to at least one double bond alkenyl group having two to eighteen carbon atoms, for example, ethenyl, propenyl, butenyl, pentenyl, hexenyl, heptenyl, heptenyl, octenyl, octadienyl, octatrienyl, nonenyl, undecenyl, dodecenyl, etc., and their isomeric forms thereof.

The term "$C_{2-18}$ alkynyl" refers to at least one triple bond alkynyl group having two to twelve carbon atoms such as, for example, ethynyl, propynyl, butynyl, pentynyl, hexynyl, heptynyl, octynyl, octadiynyl, octatriynyl, nonynyl, nonediynyl, etc., and their isomeric forms thereof.

The term "$C_{3-7}$ cycloalkyl" refers to monocyclic hydrocarbons having three to seven carbon atoms such as, for example, cyclopropyl, cyclobutyl, cyclopentyl, cyclohexyl, cycloheptyl, cyclooctyl, and their isomeric forms thereof, preferably an cycloalkyl group having three to six carbon atoms.

The term "bicycloalkyl" refers to saturated alicyclic hydrocarbon systems consisting of two rings only, having two or more atoms in common.

The terms "$C_{1-4}$ alkoxy" refers to an alkyl group having one to four carbon atoms attached to an oxygen atom of hydroxyl group such as; for example, methoxy, ethoxy, propyloxy, butyloxy, and their isomeric forms thereof.

The term "aryl" refers to monocarbocyclic or bicarbocyclic aromatic moiety such as; for example phenyl, naphthyl, biphenyl. Each of these moieties may be substituted as appropriate. Aryl is preferably phenyl or phenyl substituted with $C_{1-4}$ alkyl, $C_{1-4}$ alkoxy, halo, —CN, —$SO_2NH_2$, —$SO_2F$—, —$NO_2$, —C(=O)—O—C(=O)— or —$OCH_2O$—.

The term "het" refers to a 5- to 10-membered unsaturated heterocyclic moiety having one to three atoms selected from the group consisting of oxygen, nitrogen, and sulfur such as, for example, furyl, thienyl, pyrrolyl, pyrazolyl, imidazolyl, oxazolyl, isoxazolyl, thiazolyl, isothiazolyl, pyridyl, pyrimidinyl, pyridazinyl, pyrazinyl, pyranyl, indazolyl, benzothiazolyl, benzoimidazolyl, benzofuryl, isobenzofuryl, benzothiazole, benzoisoxazole, benzothienyl, indolyl, isoindolyl, quinolyl, isoquinolyl, quinazolinyl, quinoxalinyl, phthalazinyl or cinnolinyl.

The term "U" refers to 5- to 9-membered unsaturated heterocyclic moiety having one to three atoms selected from the group consisting of oxygen, nitrogen, and sulfur such as, for example, furyl, thienyl, pyrrolyl, pyrazolyl, imidazolyl, oxazolyl, isoxazolyl, thiazolyl, isothiazolyl, pyridyl, pyrimidinyl, pyridazinyl, pyrazinyl, pyranyl, indazolyl, benzothiazolyl, benzoimidazolyl, benzofuryl, isobenzofuryl, benzothiazole, benzoisoxazole, benzothienyl, indolyl, or isoindolyl.

The term "Q" refers to 5- or 6-membered saturated heterocyclic moiety having one to two atoms selected from the group consisting of oxygen, nitrogen, and sulfur, wherein nitrogen atom may be in turn substituted with $C_{1-4}$ alkyl, phenyl, benzyl, or —C(=O)$C_{1-4}$ alkyl. The example of Q is 2-, 3-, or 4-piperidinyl, 1-, or 2-pyrrolidinyl, morpholinyl, thiomorpholinyl, dioxolanyl, imidazolidinyl, oxathiolanyl, oxazolidinyl, tetrahydrofuryl, or 2-oxo-1-pyrrolidinyl.

The term "halo" refers to fluoro, chloro, bromo, or iodo.

The term "pharmaceutically acceptable salts" refers to those salts which possess the biological effectiveness and properties of the parent compound and which are not biologically or otherwise undesirable.

Throughout this application, abbreviations which are well known to one of ordinary skill in the art may be used, such as "Ph" for phenyl, "Me" for methyl, etc.

Examples of preferred compounds of the present invention are:

1. N-(5-{[3-(cyclohexylamino)propyl]amino}-1,3,4-thiadiazol-2-yl)-2-ethoxy-1-naphthamide,
2. N-(5-{[3-(cyclohexylamino)propyl]amino}-1,3,4-thiadiazol-2-yl)-1,3-dioxo-1,3-dihydro-2-benzofuran-5-carboxamide, 3. N-{5-[(3,3-diphenylpropyl)amino]-1,3,4-thiadiazol-2-yl}-1,3-dioxo-1,3-dihydro-2-benzofuran-5-carboxamide,
4. N-{5-[(2,2-diphenylethyl)amino]-1,3,4-thiadiazol-2-yl}-1,3-dioxo-1,3-dihydro-2-benzofuran-5-carboxamide,
5. 1,3-dioxo-N-[5-(undecylamino)-1,3,4-thiadiazol-2-yl]-1,3-dihydro-2-benzofuran-5-carboxamide,
6. N-[5-({[(2R)-6,6-dimethylbicyclo[3.1.1]hept-2-yl]methyl}amino)-1,3,4-thiadiazol-2-yl]-1,3-dioxo-1,3-dihydro-2-benzofuran-5-carboxamide,
7. 1,3-dioxo-N-{5-[(4-phenylbutyl)amino]-1,3,4-thiadiazol-2-yl}-1,3-dihydro-2-benzofuran-5-carboxamide,
8. N-(5-{[2-(1H-indol-3-yl)ethyl]amino}-1,3,4-thiadiazol-2-yl)-1,3-dioxo-1,3-dihydro-2-benzofuran-5-carboxamide,
9. (E)-N-(5-{[3-(cyclohexylamino)propyl]amino}-1,3,4-thiadiazol-2-yl)-9-octadecenamide,
10. 2-ethoxy-N-(5-{[2-(1H-indol-3-yl)ethyl]amino}-1,3,4-thiadiazol-2-yl)-1-naphthamide,
11. 2,6-dichloro-N-(5-{[3-(cyclohexylamino)propyl]amino}-1,3,4-thiadiazol-2-yl)benzamide,
12. N-[5-(cycloheptylamino)-1,3,4-thiadiazol-2-yl]-2-ethoxy-1-naphthamide,
13. N-[5-({[(2R)-6,6-dimethylbicyclo[3.1.1]hept-2-yl]methyl}amino)-1,3,4-thiadiazol-2-yl]-2-ethoxy-1-naphthamide,
14. (E)-N-(5-{[4-(aminosulfonyl)benzyl]aminol-1,3,4-thiadiazol-2-yl)-9-octadecenamide,
15. N-{5-[(2,2-diphenylethyl)amino]-1,3,4-thiadiazol-2-yl}-2-ethoxy-1-naphthamide,
16. (E)-N-(5-{[3-(cyclohexylamino)propyl]amino}-1,3,4-thiadiazol-2-yl)-3-phenyl-2-propenamide,
17. 2,6-dichloro-N-{5-[(3,3-diphenylpropyl)amino]-1,3,4-thiadiazol-2-yl}benzamide,
18. 2,6-dichloro-N-{5-[(2,2-diphenylethyl)amino]-1,3,4-thiadiazol-2-yl}benzamide,
19. (E)-N-{5-[(1,3-benzodioxol-5-ylmethyl)amino]-1,3,4-thiadiazol-2-yl}-9-octadecenamide,
20. N-(5-{[4-(aminosulfonyl)benzyl]amino}-1,3,4-thiadiazol-2-yl)-2,6-dichlorobenzamide,
21. 2,6-dichloro-N-(5-{[2-(1H-indol-3-yl)ethyl]amino}-1,3,4-thiadiazol-2yl)benzamide,
22. 4-cyano-N-{5-[(2,2-diphenylethyl)amino]-1,3,4-thiadiazol-2-yl}benzamide,
23. N-{5-[(1,3-benzodioxol-5-ylmethyl)amino]-1,3,4-thiadiazol-2-yl}-1,3-dioxo-1,3-dihydro-2-benzofuran-5-carboxamide,
24. 4-cyano-N-(5-{[3-(cyclohexylamino)propyl]amino}-1,3,4-thiadiazol-2yl)benzamide,
25. N-(5-{[2-(1H-indol-3-yl)ethyl]amino}-1,3,4-thiadiazol-2-yl)-5-nitro-2-furamide,
26. 2,6-dichloro-N-[5-({[(2R)-6,6-dimethylbicyclo[3.1.1]hept-2-yl]methyl}amino)-1,3,4-thiadiazol-2-yl]benzamide,
27. 4-cyano-N-(5-{[2-(1H-indol-3-yl)ethyl]amino}-1,3,4-thiadiazol-2-yl)benzamide,
28. N-[5-(cycloheptylamino)-1,3,4-thiadiazol-2-yl]-1,3-dioxo-1,3-dihydro-2-benzofuran-5-carboxamide,
29. N-{5-[(1,3-benzodioxol-5-ylmethyl)amino]-1,3,4-thiadiazol-2-yl}-2,6-dichlorobenzamide,
30. N-{5-[(2,2-diphenylethyl)amino]-1,3,4-thiadiazol-2-yl}-2-methoxybenzamide,
31. (E)-N-(5-{[4-(aminosulfonyl)benzyl]amino}-1,3,4-thiadiazol-2-yl)-3-phenyl-2-propenamide,
32. (E)-N-[5-({[(2R)-6,6-dimethylbicyclo[3.1.1]hept-2-yl]methyl}amino)-1,3,4-thiadiazol-2-yl]-9-octadecenamide,
33. (E)-N-(5-{[2-(1H-indol-3-yl)ethyl]amino}-1,3,4-thiadiazol-2-yl)-9-octadecenamide,
34. (E)-N-[5-(cycloheptylamino)-1,3,4-thiadiazol-2-yl]-9-octadecenamide,
35. (E)-N-{5-[(4-fluorobenzyl)amino]-1,3,4-thiadiazol-2-yl}-9-octadecenamide,
36. 2,6-dichloro-N-{5-[(4-phenylbutyl)amino]-1,3,4-thiadiazol-2-yl}benzamide, or
37. N-(5-{[4-(aminosulfonyl)benzyl]amino-1,3,4-thiadiazol-2-yl)-2-ethoxy-1-naphthamide.

Examples of more preferred compounds of the present invention are:
1. N-(5-{[3-(cyclohexylamino)propyl]amino}-1,3,4-thiadiazol-2-yl)-2-ethoxy-1-naphthamide,
2. N-(5-{[3-(cyclohexylamino)propyl]amino}-1,3,4-thiadiazol-2-yl)-1,3-dioxo-1,3-dihydro-2-benzofuran-5-carboxamide,
3. N-{5-[(3,3-diphenylpropyl)amino]-1,3,4-thiadiazol-2-yl}-1,3-dioxo-1,3-dihydro-2-benzofuran-5-carboxamide,
4. N-{5-[(2,2-diphenylethyl)amino]-1,3,4-thiadiazol-2-yl}-1,3-dioxo-1,3-dihydro-2-benzofuran-5-carboxamide,
5. 1,3-dioxo-N-[5-(undecylamino)-1,3,4-thiadiazol-2-yl]-1,3-dihydro-2-benzofuran-5-carboxamide,
6. N-[5-({[(2R)-6,6-dimethylbicyclo[3.1.1]hept-2-yl]methyl}amino)-1,3,4-thiadiazol-2-yl]-1,3-dioxo-1,3-dihydro-2-benzofuran-5-carboxamide,
7. 1,3-dioxo-N-{5-[(4-phenylbutyl)amino]-1,3,4-thiadiazol-2-yl}-1,3-dihydro-2-benzofuran-5-carboxamide,
8. N-(5-{[2-(1H-indol-3-yl)ethyl]amino}-1,3,4-thiadiazol-2-yl)-1,3-dioxo-1,3-dihydro-2-benzofuran-5-carboxamide, or
9. (E)-N-(5-{[3-(cyclohexylamino)propyl]amino}-1,3,4-thiadiazol-2-yl)-9-octadecenamide.

The compounds of the present invention and pharmaceutically acceptable salts thereof are useful as antiviral agents. Thus, these compounds are useful to combat viral infections in animals, including man. Specifically, these compounds have anti-viral activity against the herpes virus, cytomegalovirus (CMV). Many of these compounds are also active against other herpes viruses, such as the varicella zoster virus, the Epstein-Barr virus, the herpes simplex virus, and the human herpes virus type 8 (HHV-8).

Also, while many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The compounds of the present invention are tested in an polymerase assay to show activity described below, which is indicative of a compound's activity and thus of its use as an anti-viral agent.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM $MgCl_2$, 0.36 mg/ml BSA, and 90 nM $^3$H-dTTP. Assays are run with and without CHAPS, (3-[(3-Cholamidopropyl)-dimethylammonio]-1-propanesulfonate) at a final concentration of 2 mM. HCMV is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. $H_2O$ bath and terminated via the addition of 40 μl/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37° C., then equilibrated to room temperature, and counted on a Packard Topcount. Results of the testing of compounds of the present invention in this assay are shown in TABLE 1 below.

These compounds of the present invention are administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975), which is hereby incorporated by reference herein.

The quantity of active component, that is the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The compounds of the present invention are administered parenterally (for example, by intravenous, intraperitoneal or intramuscular injection), topically, orally, or rectally, depending on whether the preparation is used to treat internal or external viral infections.

For internal infections, the compositions are administered orally or parenterally at dose levels, calculated as the free base, of about 0.1 to 300 mg/kg, preferably 1.0 to 30 mg/kg of mammal body weight, and are used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to 10%, more preferably about 0.1 to 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The following Scheme outlines the preparation of the compounds of the present invention.

SCHEME I

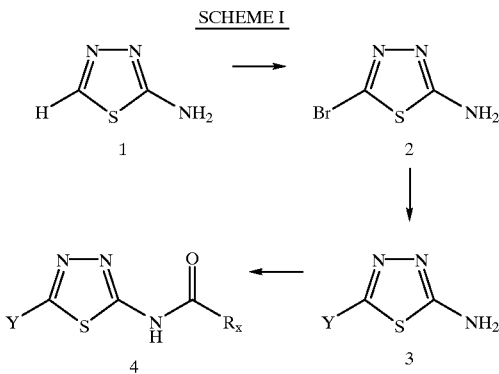

In Scheme I, Y is —$NHR_1$, or

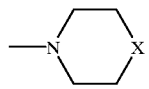

$R_1Rx$ and X are as defined previously. The synthesis of structures 3 and 4, the compounds of the present invention, required two or three steps. 2-Amino-5-bromo-1,3,4-thiadiazole 2 is prepared through bromination of commercially available 2-amino-1,3,4-thiadiazole. Compound 3 is prepared through direct bromide displacement of thiadiazole 2 with an appropriate amine. Compound 3 then react with an appropriate acid chloride to provide compound 4.

It will be apparent to those skilled in the art that the described synthetic procedures are merely representative in nature and that alternative synthetic processes are known to one of ordinary skill in organic chemistry.

The compounds and their preparations of the present invention will be better understood in connection with the following examples, which are intended as an illustration of and not a limitation upon the scope of the invention.

EXAMPLE 1

Preparation of Starting Material 5-bromo-1,3,4-thiadiazol-2ylamine.

To a stirred solution of 2-amino-1,3,4-thiadiazole (40.5 g) in 250 ml of acetic acid is added 22.7 ml of bromine over about 20 minutes. The flask is surrounded by an ice bath during the addition to maintain the reaction temperature near 25° C. Following the addition, the ice bath is removed and the clear red solution stirred at ambient temperature for 18 hours, then added to 1L of cracked ice. Excess bromine is quenched with $NaHSO_3$, and 40 ml of 50% aqueous NaOH is added. The precipitated solid is isolated by filtration and washed well with water, then dissolved in 300 ml of water containing 40 ml concentrated. HCl. The solution is filtered from a small amount of solid, then 87 g of $K_2HPO_4$ in a small quantity of water is added. The resulting slurry is chilled in ice and filtered, and the solid washed well with water. Recrystallization of the product from 400 ml of ethanol provides 26.3 g of the title compound.

$^1$NMR (DMSO-d$_6$) δ 7.51 ppm.

EXAMPLE 2

Preparation of tert-Butyl 4-(5-amino-1,3,4-thiadiazol-2-yl)tetrahydro-1(2H)-pyrazinecarboxylate.

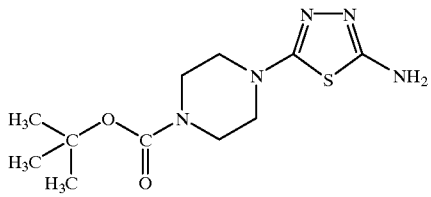

A mixture of 5-bromo-1,3,4-thiadiazol-2-ylamine (9.27 g), Boc-piperazine (11.51 g), and K$_2$HPO$_4$ (13.4 g) in 30 ml of DMF is heated at 100° C. under argon for four hours, then cooled and added to 100 g of ice. The mixture is extracted with ethyl acetate, and the organic phase washed twice with water and dried (MgSO$_4$). Following removal of the solvent under reduced pressure, the residue is flash chromatographed on silica using 4% methanol in dichloromethane to afford 8.32 g of the title compound as a solid. Recrystallization from 240 ml of 1:1 acetonitrile-toluene provides 6.65 g of solid.

$^1$NMR δ 1.47, 3.34, 3.53, 4.8 ppm; IR 3411, 3132, 1698, 1676, 1500, 1427, 1251, 1167 cm$^{-1}$; EI HRMS m/z found: 285.1277; M.p. 215–216° C.

EXAMPLE 3

Preparation of N-(5-Amino-1,3,4-thiadiazol-2-yl)-N-phenethylamine.

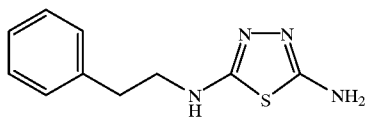

A mixture of 5-bromo-1,3,4-thiadiazol-2-ylamine (360 mg), phenethylamine (0.38 ml), and K$_2$HPO$_4$ (522 mg) in 2 ml of DMF is heated under nitrogen at 100° C. for two hours, then partitioned between water and ethyl acetate. The organic phase is washed with water and brine, dried over MgSO$_4$, and concentrated under reduced pressure. Flash chromatography of the residue on silica using 4–5% methanol in dichloromethane provides 261 mg of the title compound. Recrystallization of 238 mg of this from 10 ml of 1:1 acetonitrile toluene affords 205 mg of crystals.

$^1$H NMR δ 2.92, 3.50, 7.2–7.3 ppm; IR 3186, 1565, 1505 cm$^{-1}$; EI MS m/z 221; M.p. 156–157° C.; Anal. Found: C, 54.51; H, 5.47; N, 25.26; S, 14.30.

EXAMPLE 4

Preparation of 5-Morpholino-1,3,4-thiadiazol-2-ylamine.

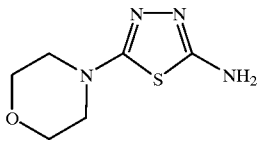

A mixture of 5-bromo-1,3,4-thiadiazol-2-ylamine, K$_2$HPO$_4$ (5.7 g), and 5.3 ml of morpholine in 20 ml of DMF is heated at 80° C. under nitrogen for 18 hours, then diluted with 50 ml of water. The clear solution is placed in a continuous extractor and extracted with a brisk flow of dichloromethane for 18 hours. The solution is dried over MgSO$_4$ and concentrated under reduced pressure, with toluene azeotropes to remove DMF. Recrystallization of the residual solid from 50 ml of acetonitrile and 100 ml of toluene affords 3.92 g of the title compound.

$^1$H NMR δ 3.34, 3.80 ppm; IR 1528, 1499, 1448, 1245, 1112, 1036, 906 cm$^{-1}$; EI MS m/z 186; Anal. Found: C, 38.67; H, 5.48; N, 30.17; S, 17.18.

EXAMPLE 5

Preparation of tert-Butyl N-{2-[(5-amino-1,3,4-thiadiazol-2-yl)amino]ethyl}carbamate.

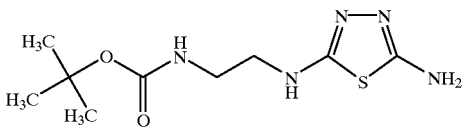

A mixture of 5-bromo-1,3,4-thiadiazol-2-ylamine (5.40 g), K$_2$HPO$_4$ (7.84 g), and Boc-ethylenediamine (9.6 g) in 20 ml of DMF is stirred at ambient temperature for 18 hours. The solid paste obtained is recrystallized from 100 ml of acetonitrile and 100 ml of water to provide 6.18 g (79%) of the title compound.

$^1$H NMR (MeOH-d$_4$) δ 1.40, 3.2–3.3 ppm; IR 2989, 1676, 1577, 1512, 1366 cm$^{-1}$; EI MS m/z 260; M.p. 219–220° C.

EXAMPLE 6

Preparation of N-[5-(Cycloheptylamino)-1,3,4-thiadiazol-2-yl]-2-ethoxy-1-naphthamide.-ethoxy-1-naphthoyl).

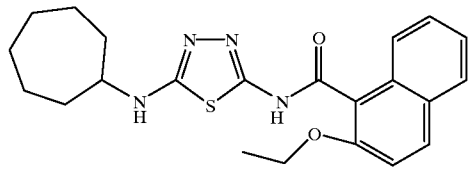

A mixture of 5-bromo-1,3,4-thiadiazol-2-ylamine (720 mg), K$_2$HPO$_4$ (780 mg), and cycloheptylamine (0.51 mg) in 5 ml of DMF is stirred at 60° C. for 4 hours, then diluted with pyridine and centrifuged to remove solids. To one-half of this solution, cooled to 0° C., is added a solution of 469 mg of 2-ethoxy-1-naphthoyl chloride in 5 ml of chloroform. The solution is stirred at room temperature overnight, then concentrated under reduced pressure. Addition of water and ethyl acetate to the residue provides a solid, which is filtered, washed with ethyl acetate and water, and dried under vacuum to afford 200 mg of the title compound as a white solid.

$^1$H NMR (CDCl$_3$) δ 1.50, 1.4–1.8, 2.1, 3.6, 4.26, 7.3–7.6, 7.8, 8.0 ppm; HRMS (m+H) 411.1875.

EXAMPLE 7

Preparation of N-[5-(Cycloheptylamino)-1,3,4-thiadiazol-2-yl]-2-methoxybenzamide.

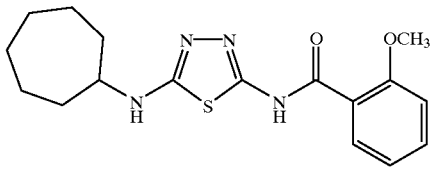

A mixture of 5-bromo-1,3,4-thiadiazol-2-ylamine (720 mg), K$_2$HPO$_4$ (780 mg), and cycloheptylamine (0.51 mg) in 5 ml of DMF is stirred at 60° C. for 4 hours, then diluted with pyridine and centrifuged to remove solids. To one-half of this solution, cooled to 0° C., is added 0.30 ml of o-anisoyl chloride. The solution is stirred at room temperature overnight, then concentrated under reduced pressure and diluted with 100 ml of water. The precipitated solid is filtered, washed with water, and dried under vacuum to afford 641 mg of the title compound.

$^1$H NMR (CDCl$_3$) δ 1.4–1.7, 2.1, 3.6, 4.09, 7.0–7.2, 7.6, 8.25 ppm; HRMS m/z 346.1469.

EXAMPLE 8

Preparation of N-{5-[(2,2-Diphenylethyl)amino]-1,3,4-thiadiazol-2-yl}-2-ethoxy-1-naphthamide.

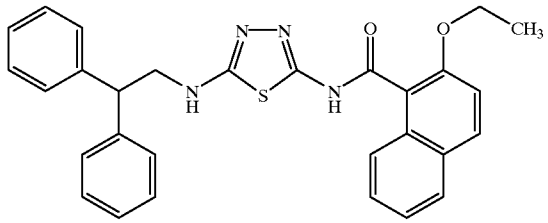

A mixture 5-bromo-1,3,4-thiadiazol-2-ylamine (720 mg), K$_2$HPO$_4$ (780 mg), and 2,2-diphenylethylamine (789 mg) in 5 ml of DMF is stirred at 60° C. for 4 hours, then diluted with pyridine and centrifuged to remove solids. To one-half of this solution, cooled to 0° C., is added a solution of 2-ethoxy-1-naphthoyl chloride (469 mg) in 5 ml of chloroform. The solution is stirred at room temperature overnight, then concentrated under reduced pressure and diluted with 100 ml of water. The resultant solid is filtered, washed with water, and dried under vacuum to provide 947 mg of the title compound.

$^1$H NMR (CDCl$_3$) δ 1.43, 4.02, 4.15, 4.26, 4.44, 7.2–7.6, 7.8–8.0 ppm; HRMS (m+H) 495.1846.

EXAMPLE 9

Preparation of 2-Ethoxy-N-(5-{[2-(1H-indol-3-yl)ethyl]amino}-1,3,4-thiadiazol-2-yl)-1-naphthamide.

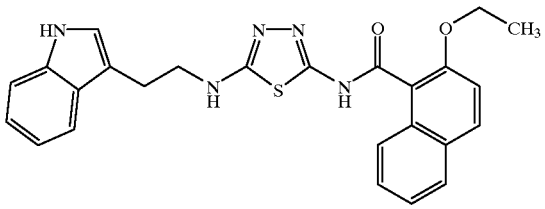

A mixture of 5-bromo-1,3,4-thiadiazol-2-ylamine (720 mg), K$_2$HPO$_4$ (780 mg), and tryptamine (641 mg) in 5 ml of DMF is stirred at 60° C. for 12 hours, then diluted with pyridine and centrifuged to remove solids. To one-half of this solution, cooled to 0° C., is added a solution of 469 mg of 2-ethoxy-1-naphthoyl chloride in 5 ml of chloroform. The solution is stirred at room temperature overnight, then concentrated under reduced pressure and diluted with 100 ml of water. The resultant solid is filtered, washed with water, and dried under vacuum to provide 866 mg of white solid. Column chromatography of 249 mg of this on silica, using 1.5–4% methanol in dichloromethane, provides 191 mg of the title compound.

$^1$H NMR (CDCl$_3$) δ 1.43, 3.16, 3.70, 4.26, 7.0–7.2, 7.3–7.4, 7.5, 7.6, 7.8, 8.0 ppm; HRMS (m+H) 458.1655.

EXAMPLE 10

Preparation of N-[5-({[(2R)-6,6-Dimethylbicyclo[3.1.1]hept-2-yl]methyl}amino)-1,3,4-thiadiazol-2-yl]-2-ethoxy-1-naphthamide.

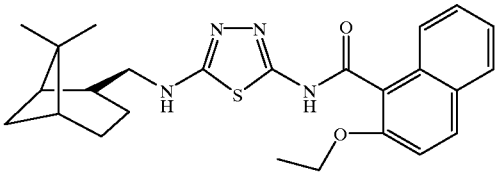

A mixture of 5-bromo-1,3,4-thiadiazol-2-ylamine (720 mg), K$_2$HPO$_4$ (780 mg), and myrtanylamine (0.67 mg) in 5 ml of DMF is stirred at 60° C. for 12 hours, then diluted with pyridine and centrifuged to remove solids. To one-half of this solution, cooled to 0° C., is added a solution of 2-ethoxy-1-naphthoyl chloride (469 mg) in 5 ml of chloroform. The solution is stirred at room temperature overnight, then concentrated under reduced pressure and diluted with 100 ml of water. The resultant solid is filtered, washed with water, and dried under vacuum to provide 846 mg of solid. Column chromatography of 249 mg of this on silica, using 2–4% methanol in dichloromethane, provides 220 mg of the title compound.

$^1$H NMR (CDCl$_3$) δ 1.07, 1.23, 1.44, 1.8–2.1, 2.4, 3.3, 4.27, 7.2–7.6, 7.8, 8.0 ppm; HRMS (m+H) 451.2163.

EXAMPLE 11

The Following 1,3,4-Thiadiazoles of the Present Invention Are Prepared by General Procedure Described Below.

To each 48 solutions of 5-bromo-1,3,4-thiadiazol-2-ylamine (234 mg, 1.3 mmol) in 1.5 ml of DMF is added K₂HPO₄ (272 mg) and 1.3 mmol of the following amines respectively: phenethylamine, 2-furylmethylamine, 1-(3-aminopropyl)-2-pyrrolidinone, 2-pyridinylmethylamine, N-(2-aminoethyl)-N-phenylamine, 2-(1H-indol-3-yl)ethylamine, cycloheptylamine, cyclohexylmethylamine, (1S,2R,5S)-6,6-dimethylbicyclo[3.1.1]hept-2-yl]methylamine, 2-(1-pyrrolidinyl)ethylamine, tetrahydro-2-furanylmethylamine, 4-pyridinylmethylamine, 1,3-benzodioxol-5-ylmethylamine, 2-morpholinoethylamine, 1-naphthylmethylamine, 4-fluorobenzylamine, 3-pyridinylmethylamine, 2-piperidinoethylamine, 2-ethylhexylamine, 4-(2-aminoethyl)benzenesulfonamide, N-(3-aminopropyl)-N-cyclohexylamine, 3,4-dichlorobenzylamine, 3,4-dimethoxybenzylamine, 4-phenylbutylamine, 2,2-diphenylethylamine, undecylamine, 3,3-diphenylpropylamine, 2-(2-thienyl)ethylamine, 4-(aminomethyl)benzenesulfonamide, 3-(4-methylpiperazino)propylamine, 3-aminopropanenitrile, 2-(phenylsulfanyl)ethylamine, 2-thienylmethylamine, N-(2-aminoethyl)acetamide, 3-(1H-imidazol-1-yl)propylamine, tert-butyl 3-aminopropanoate, cyclopropylamine, cyclopropylmethylamine, 2-(1H-imidazol-4-yl)ethylamine, 2-(ethylsulfanyl)ethylamine, cyclobutylamine, 2-(1-methyl-2-pyrrolidinyl)ethylamine, 2,3-dihydro-1H-inden-1-ylamine, neopentylamine, 1,2,3,4-tetrahydro-1-naphthalenamine, ethyl 4-aminotetrahydro-1(2H)-pyridinecarboxylate, 1-benzyl-4-piperidinylamine, and N-(2-aminoethyl)-N,N-dimethylamine.

The resultant 48 mixtures are heated at 60° C. for 3 hours to provide a DMF solutions of the corresponding substituted aminothiadiazole intermediates. The solutions of intermediate aminothiadiazoles are diluted with pyridine to a volume of 10.0 ml, and solids are removed by centrifugation. The supernatants are aliquoted into wells of 96-well plates (0.40 ml per well) respectively, and to each well is added 0.26 ml of a 0.2 M chloroform solution of the following acid chlorides respectively: 2,4-difluorobenzoyl chloride, 2-methoxybenzoyl chloride, 4-bromobenzoyl chloride, 4-methylbenzoyl chloride, 5-chloropentanoyl chloride, 4-cyanobenzoyl chloride, 3-nitrobenzoyl chloride, 3,5-difluorobenzoyl chloride, (E)-3-(2-chlorophenyl)-2-propenoyl chloride, 2-ethoxy-1-naphthoyl chloride, (Z)-9-octadecenoyl chloride, 2,6-dichlorobenzoyl chloride, 3,4-dichlorobenzoyl chloride, 4-(trifluoromethyl)benzoyl chloride, (E)-3-phenyl-2-propenoyl chloride, 4-iodobenzoyl chloride, 1,3-dioxo-1,3-dihydro-2-benzofuran-5-carbonyl chloride, 4-(fluorosulfonyl)benzoyl chloride, 2,4,6-triisopropylbenzoyl chloride, 5-nitro-2-furoyl chloride, and 1-benzothiophene-2-carbonyl chloride.

The plates are shaken at intervals to effect mixing of reactants, and the acylation is allowed to proceed at room temperature overnight. Removal of the solvents in a stream of air or under vacuum then affords the compounds listed in TABLE 1.

All the amines and acid chlorides used above are either commercially available or can be easily prepared by one having ordinary skill in the organic chemistry art utilizing well known procedures.

In TABLE 1, "MS" refers to mass spectral data, "% inhib" refers to percentage of inhibition at 25 µM concentration in CMV polymerase assay.

TABLE 1

| | | MS | % Inhib |
|---|---|---|---|
| 1 | (E)-N-(5-{[3-(cyclohexylamino)propyl]amino}-1,3,4-thiadiazol-2-yl)-9-octadecenamide | 520 | 100.2 |
| 2 | N-(5-{[3-(cyclohexylamino)propyl]amino}-1,3,4-thiadiazol-2-yl)-1,3-dioxo-1,3-dihydro-2-benzofuran-5-carboxamide | — | 100.1 |
| 3 | N-{5-[(cyclohexylmethyl)amino]-1,3,4-thiadiazol-2-yl}-1,3-dioxo-1,3-dihydro-2-benzofuran-5-carboxamide | 419 | 100.0 |
| 4 | 1,3-dioxo-N-[5-(undecylamino)-1,3,4-thiadiazol-2-yl]-1,3-dihydro-2-benzofuran-5-carboxamide | 443 | 100.0 |
| 5 | (E)-N-(5-{[2-(1-methyl-2-pyrrolidinyl)ethyl]amino}-1,3,4-thiadiazol-2-yl)-9-octadecenamide | 492 | 99.9 |
| 6 | N-{5-[(2-anilinoethyl)amino]-1,3,4-thiadiazol-2-yl}-1,3-dioxo-1,3-dihydro-2-benzofuran-5-carboxamide, | 410 | 99.9 |
| 7 | N-{5-[(4-fluorobenzyl)amino]-1,3,4-thiadiazol-2-yl}-1,3-dioxo-1,3-dihydro-2-benzofuran-5-carboxamide | 399 | 99.8 |
| 8 | N-{5-[(1-naphthylmethyl)amino]-1,3,4-thiadiazol-2-yl}-1,3-dioxo-1,3-dihydro-2-benzofuran-5-carboxamide | 431 | 99.8 |
| 9 | 1,3-dioxo-N-(5-{[2-(2-thienyl)ethyl]amino}-1,3,4-thiadiazol-2-yl)-1,3-dihydro-2-benzofuran-5-carboxamide | 401 | 99.8 |
| 10 | N-(5-{[2-(1H-indol-3-yl)ethyl]amino}-1,3,4-thiadiazol-2-yl)-1,3-dioxo-1,3-dihydro-2-benzofuran-5-carboxamide | 434 | 99.7 |
| 11 | 1,3-dioxo-N-{5-[(4-phenylbutyl)amino]-1,3,4-thiadiazol-2-yl}-1,3-dihydro-2-benzofuran-5-carboxamide | 421 | 99.6 |
| 12 | N-{5-[(3,4-dichlorobenzyl)amino]-1,3,4-thiadiazol-2-yl}-1,3-dioxo-1,3-dihydro-2-benzofuran-5-carboxamide | 449 | 99.5 |
| 13 | N-{5-[(3,3-diphenylpropyl)amino]-1,3,4-thiadiazol-2-yl}-1,3-dioxo-1,3-dihydro-2-benzofuran-5-carboxamide | 483 | 99.3 |
| 14 | (E)-N-(5-{[3-(4-methylpiperazino)propyl]amino}-1,3,4-thiadiazol-2-yl)-9-octadecenamide | 521 | 99.0 |
| 15 | N-(5-{[4-(aminosulfonyl)phenethyl]amino}-1,3,4-thiadiazol-2-yl)-1,3-dioxo-1,3-dihydro-2-benzofuran-5-carboxamide | 474 | 98.8 |
| 16 | N-{5-[(3,4-dimethoxybenzyl)amino]-1,3,4-thiadiazol-2-yl}-1,3-dioxo-1,3-dihydro-2-benzofuran-5-carboxamide | 441 | 98.7 |
| 17 | N-{5-[(2,2-diphenylethyl)amino]-1,3,4-thiadiazol-2-yl}-1,3-dioxo-1,3-dihydro-2-benzofuran-5-carboxamide | 471 | 98.6 |
| 18 | (E)-N-(5-{[4-(aminosulfonyl)benzyl]amino}-1,3,4-thiadiazol-2-yl)-9-octadecenamide | — | 98.3 |

TABLE 1-continued

|    |                                                                                                                     | MS  | % Inhib |
|----|---------------------------------------------------------------------------------------------------------------------|-----|---------|
| 19 | (E)-N-(5-{[2-(1-pyrrolidinyl)ethyl]amino}-1,3,4-thiadiazol-2-yl)-9-octadecenamide                                    | 478 | 97.7    |
| 20 | N-{5-[(1,3-benzodioxol-5-ylmethyl)amino]-1,3,4-thiadiazol-2-yl}-1,3-dioxo-1,3-dihydro-2-benzofuran-5-carboxamide     | 425 | 97.7    |
| 21 | 1,3-dioxo-N-[5-(1,2,3,4-tetrahydro-1-naphthalenylamino)-1,3,4-thiadiazol-2-yl]-1,3-dihydro-2-benzofuran-5-carboxamide | 421 | 97.4    |
| 22 | N-[5-({[(2R)-6,6-dimethylbicyclo[3.1.1]hept-2-yl]methyl}-amino)-1,3,4-thiadiazol-2-yl]-2-methoxybenzamide             | 387 | 97.2    |
| 23 | (E)-N-(5-{[2-(dimethylamino)ethyl]amino}-1,3,4-thiadiazol-2-yl)-9-octadecenamide                                     | 452 | 97.0    |
| 24 | 1,3-dioxo-N-[5-(phenethylamino)-1,3,4-thiadiazol-2-yl]-1,3-dihydro-2-benzofuran-5-carboxamide                        | 395 | 95.6    |
| 25 | N-[5-({[(2R)-6,6-dimethylbicyclo[3.1.1]hept-2-yl]methyl}-amino)-1,3,4-thiadiazol-2-yl]-1,3-dioxo-1,3-dihydro-2-benzofuran-5-carboxamide | 425 | 93.9    |
| 26 | N-(5-{[4-(aminosulfonyl)benzyl]amino}-1,3,4-thiadiazol-2-yl)-2-ethoxy-1-naphthamide                                  | 484 | 93.1    |
| 27 | N-(5-{[3-(cyclohexylamino)propyl]amino}-1,3,4-thiadiazol-2-yl)-2-ethoxy-1-naphthamide                                | 454 | 92.9    |
| 28 | (E)-N-[5-(cyclopropylamino)-1,3,4-thiadiazol-2-yl]-9-octadecenamide                                                  | 421 | 92.6    |
| 29 | N-[5-cycloheptylamino)-1,3,4-thiadiazol-2-yl]-1,3-dioxo-1,3-dihydro-2-benzofuran-5-carboxamide                       | 387 | 92.4    |
| 30 | N-(5-{[4-(aminosulfonyl)benzyl]amino}-1,3,4-thiadiazol-2-yl)-2,6-dichlorobenzamide                                   | 458 | 91.8    |
| 31 | (E)-N-[5-(cycloheptylamino)-1,3,4-thiadiazol-2-yl]-9-octadecenamide                                                  | 477 | 91.8    |
| 32 | (E)-N-(5-{[4-(aminosulfonyl)benzyl]amino}-1,3,4-thiadiazol-2-yl)-3-phenyl-2-propenamide                              | 416 | 90.6    |
| 33 | 1,3-dioxo-N-(5-{[2-(phenylsulfanyl)ethyl]amino}-1,3,4-thiadiazol-2-yl)-1,3-dihydro-2-benzofuran-5-carboxamide        | 425 | 90.1    |
| 34 | (E)-3-(2-chlorophenyl)-N-{5-[(cyclopropylmethyl)amino]-1,3,4-thiadiazol-2-yl}-2-propenamide                          | 335 | 89.9    |
| 35 | N-(5-{[4-(aminosulfonyl)benzyl]amino}-1,3,4-thiadiazol-2-yl)-2,4,6-triisopropylbenzamide                             | 516 | 89.7    |
| 36 | N-(5-{[3-(cyclohexylamino)propyl]amino}-1,3,4-thiadiazol-2-yl)-2,4,6-triisopropylbenzamide                           | 486 | 87.6    |
| 37 | 2,6-dichloro-N-(5-{[3-(cyclohexylamino)propyl]amino}-1,3,4-thiadiazol-2-yl)benzamide                                 | 428 | 87.4    |
| 38 | (E)-N-{5-[(2,2-diphenylethyl)amino]-1,3,4-thiadiazol-2-yl}-9-octadecenamide                                          | 561 | 87.3    |
| 39 | 1,3-dioxo-N-{5-[(2-thienylmethyl)amino]-1,3,4-thiadiazol-2-yl}-1,3-dihydro-2-benzofuran-5-carboxamide                | 387 | 87.1    |
| 40 | N-[5-(2,3-dihydro-1H-inden-1-ylamino)-1,3,4-thiadiazol-2-yl]-1,3-dioxo-1,3-dihydro-2-benzofuran-5-carboxamide        | 407 | 86.3    |
| 41 | (E)-N-(5-{[2-(2-thienyl)ethyl]amino}-1,3,4-thiadiazol-2-yl)-9-octadecenamide                                         | 491 | 85.7    |
| 42 | (E)-N-{5-[(2-thienylmethyl)amino]-1,3,4-thiadiazol-2-yl}-9-octadecenamide                                            | 477 | 84.6    |
| 43 | N-{5-[(1,3-benzodioxol-5-ylmethyl)amino]-1,3,4-thiadiazol-2-yl}-2-ethoxy-1-naphthamide                               | 449 | 83.9    |
| 44 | N-{5-[(1-naphthylmethyl)amino]-1,3,4-thiadiazol-2-yl}-5-nitro-2-furamide                                             | 396 | 83.3    |
| 45 | N-{5-[(1-benzyl-4-piperidinyl)amino]-1,3,4-thiadiazol-2-yl}-2-ethoxy-1-naphthamide                                   | 488 | 83.1    |
| 46 | 4-cyano-N-{5-[(3,3-diphenylpropyl)amino]-1,3,4-thiadiazol-2-yl}benzamide                                             | 440 | 82.3    |
| 47 | N-(5-{[2-(1H-indol-3-yl)ethyl]amino}-1,3,4-thiadiazol-2-yl)-5-nitro-2-furamide                                       | 399 | 81.6    |
| 48 | (E)-N-{5-[(4-fluorobenzyl)amino]-1,3,4-thiadiazol-2-yl}-9-octadecenamide                                             | 489 | 81.5    |
| 49 | 4-({[5-(undecylamino)-1,3,4-thiadiazol-2-yl]amino}-carbonyl)benzenesulfonyl fluoride                                 | —   | 80.3    |
| 50 | (E)-N-(5-{[4-(aminosulfonyl)phenethyl]amino}-1,3,4-thiadiazol-2-yl)-3-phenyl-2-propenamide                           | 430 | 79.8    |
| 51 | (E)-N-[5-(undecylamino)-1,3,4-thiadiazol-2-yl]-9-octadecenamide                                                      | 535 | 79.5    |
| 52 | N-{5-[(4-phenylbutyl)amino]-1,3,4-thiadiazol-2-yl}-1-benzothiophen-2-carboxamide                                     | —   | 78.7    |
| 53 | (E)-N-{5-[(1,3-benzodioxol-5-ylmethyl)amino]-1,3,4-thiadiazol-2-yl}-9-octadecenamide                                 | 515 | 77.9    |
| 54 | 1,3-dioxo-N-{5-[(4-pyridinylmethyl)amino]-1,3,4-thiadiazol-2-yl}-1,3-dihydro-2-benzofuran-5-carboxamide              | 382 | 77.7    |
| 55 | N-{5-[(2,2-diphenylethyl)amino]-1,3,4-thiadiazol-2-yl}-2-ethoxy-1-naphthamide                                        | 495 | 77.6    |

TABLE 1-continued

| | | MS | % Inhib |
|---|---|---|---|
| 56 | 2,6-dichloro-N-{5-[(2,2-diphenylethyl)amino]-1,3,4-thiadiazol-2-yl}benzamide | 469 | 77.4 |
| 57 | N-(5-{[4-(aminosulfonyl)benzyl]amino}-1,3,4-thiadiazol-2-yl)-4-iodobenzamide | 516 | 76.3 |
| 58 | (E)-N-(5-{[2-(phenylsulfanyl)ethyl]amino}-1,3,4-thiadiazol-2-yl)-9-octadecenamide | 517 | 75.8 |
| 59 | 4-iodo-N-{5-[(4-phenylbutyl)amino]-1,3,4-thiadiazol-2-yl}benzamide | 479 | 74.6 |
| 60 | 5-nitro-N-[5-(undecylamino)-1,3,4-thiadiazol-2-yl]-2-furamide | — | 74.5 |
| 61 | N-{5-[(3,3-diphenylpropyl)amino]-1,3,4-thiadiazol-2-yl}-2-ethoxy-1-naphthamide | 509 | 74.2 |
| 62 | N-(5-{[3-(cyclohexylamino)propyl]amino}-1,3,4-thiadiazol-2-yl)-1-benzothiophene-2-carboxamide | 416 | 74.0 |
| 63 | 2,6-dichloro-N-{5-[(3,3-diphenylpropyl)amino]1,3,4-thiadiazol-2-yl}benzamide | 483 | 73.8 |
| 64 | (E)-N-{5-[(3,3-diphenylpropyl)amino]-1,3,4-thiadiazol-2-yl}-9-octadecenamide | 575 | 73.6 |
| 65 | 4-cyano-N-[5-(undecylamino)-1,3,4-thiadiazol-2-yl]benzamide | 400 | 72.2 |
| 66 | 2-ethoxy-N-{5-[(3-pyridinylmethyl)amino]-1,3,4-thiadiazol-2-yl}-1-naphthamide | 406 | 71.9 |
| 67 | (E)-3-(2-chlorophenyl)-N-{5-[(4-fluorobenzyl)amino]-1,3,4-thiadiazol-2-yl}-2-propenamide | 389 | 71.7 |
| 68 | N-(5-{[4-(aminosulfonyl)phenthyl]amino}-1,3,4-thiadiazol-2-yl)-4-iodobenzamide | 530 | 71.1 |
| 69 | N-{5-[(2-anilinoethyl)amino]-1,3,4-thiadiazol-2-yl}-2-ethoxy-1-naphthamide | 434 | 70.6 |
| 70 | 2-ethoxy-N-{5-[(2-pyridinylmethyl)amino]-1,3,4-thiadiazol-2-yl}-1-naphthamide | 406 | 70.4 |
| 71 | 2-ethoxy-N-{5-[(4-fluorobenzyl)amino]-1,3,4-thiadiazol-2-yl}-1-naphthamide | 423 | 69.8 |
| 72 | (E)-N-{5-[(3-pyridinylmethyl)amino]-1,3,4-thiadiazol-2-yl}-9-octadecenamide | 470 | 69.3 |
| 73 | 2,6-dichloro-N-{5-[(3,4-dichlorobenzyl)amino]-1,3,4-thiadiazol-2-yl}benzamide | 449 | 69.1 |
| 74 | 4-cyano-N-{5-[(4-fluorobenzyl)amino]-1,3,4-thiadiazol-2-yl}benzamide | 354 | 69.0 |
| 75 | (E)-3-(2-chlorophenyl)-N-(5-{[3-(cyclohexylamino)-propyl]amino}-1,3,4-thiadiazol-2-yl)-2-propenamide | 420 | 68.8 |
| 76 | 2,6-dichloro-N-[5-(1,2,3,4-tetrahydro-1-naphthalenyl-amino)-1,3,4-thiadiazol-2-yl]benzamide | 419 | 68.5 |
| 77 | (E)-3-phenyl-N-(5-{[2-(2-thienyl)ethyl]amino}-1,3,4-thiadiazol-2-yl)-2-propenamide | 357 | 68.3 |
| 78 | 2-ethoxy-N-{5-[(2-thienylmethyl)amino]-1,3,4-thiadiazol-2-yl}-1-naphthamide | 411 | 68.2 |
| 79 | tert-butyl-3-({5-[(E)-9-octadecenoylamino]-1,3,4-thiadiazol-2-yl}amino)propanoate | — | 68.0 |
| 80 | 3-nitro-N-[5-(undecylamino)-1,3,4-thiadiazol-2-yl]-benzamide | — | 67.9 |
| 81 | (E)-3-phenyl-N-{5-[(4-phenylbutyl)amino]-1,3,4-thiadiazol-2-yl}-2-propenamide | 379 | 67.9 |
| 82 | 4-cyano-N-(5-{[2-(1H-indol-3-yl)ethyl]amino}-1,3,4-thiadiazol-2-yl)benzamide | 389 | 67.7 |
| 83 | 4-cyano-N-{5-[(2,2-diphenylethyl)amino]-1,3,4-thiadiazol-2-yl}benzamide | 426 | 67.7 |
| 84 | 2,6-dichloro-N-{5-[(4-pyridinylmethyl)amino]-1,3,4-thiadiazol-2-yl}benzamide | 380 | 67.6 |
| 85 | N-{5-[(1-benzyl-4-piperidinyl)amino]-1,3,4-thiadiazol-2-yl}-1,3-dioxo-1,3-dihydro-2-benzofuran-5-carboxamide | 464 | 67.3 |
| 86 | ethyl 4-[(5-{[(2-ethoxy-1-naphthyl)carbonyl]amino}-1,3,4-thiadiazol-2-yl)amino]tetrahydro-1(2H)-pyridinecarboxylate | 470 | 67.0 |
| 87 | N-(5-{[3-(1H-imidazol-1-yl)propyl]amino}-1,3,4-thiadiazol-2-yl)-2,4,6-triisopropylbenzamide | 455 | 67.0 |
| 88 | (E)-N-(5-{[4-(aminosulfonyl)benzyl]amino}-1,3,4-thiadiazol-2-yl)-3-(2-chlorophenyl)-2-propenamide | 450 | 66.5 |
| 89 | 2-ethoxy-N-(5-{[2-(1H-imidazol-4-yl)ethyl]amino}-1,3,4-thiadiazol-2-yl)-1-naphthamide | 409 | 66.3 |
| 90 | 4-{[(5-{[2-(1H-indol-3-yl)ethyl]amino}-1,3,4-thiadiazol-2-yl)amino]carbonyl}benzenesulfonyl fluoride | 446 | 66.1 |
| 91 | ethyl 4-({5-[(E)-9-octadecenoylamino]-1,3,4-thiadiazol-2-yl}amino)tetrahydro-1(2H)-pyridinecarboxylate | 272 | 66.1 |
| 92 | 2,6-dichloro-N-(5-{[2-(2-thienyl)ethyl]amino}-1,3,4-thiadiazol-2-yl)benzamide | 399 | 66.1 |

TABLE 1-continued

|  |  | MS | % Inhib |
|---|---|---|---|
| 93 | 2-ethoxy-N-[5-(1,2,3,4-tetrahydro-1-naphthaienylamino)-1,3,4-thiadiazol-2-yl]-1-naphthamide | 445 | 66.0 |
| 94 | (E)-3-phenyl-N-{5-[(4-pyridinylmethyl)amino]-1,3,4-thiadiazol-2-yl}-2-propenamide | 338 | 65.9 |
| 95 | N-[5-(2,3-dihydro-1H-inden-1-ylamino)-1,3,4-thiadiazol-2-yl]-2-ethoxy-1-naphthamide | 431 | 65.9 |
| 96 | N-{5-[(1,3-benzodioxol-5-ylethyl)amino]-1,3,4-thiadiazol-2-yl}-2,6-dichlorobenzamide | 423 | 65.9 |
| 97 | 2-ethoxy-N-(5-{[2-(2-thienyl)ethyl]amino}-1,3,4-thiadiazol-2-yl)-1-naphthamide | 425 | 65.8 |
| 98 | (E)-3-(2-chlorophenyl)-N-(5-{[2-(1H-imidazol-4-yl)ethyl]amino}-1,3,4-thiadiazol-2-yl)-2-propenamide | 375 | 65.7 |
| 99 | 2,6-dichloro-N-(5-{[3-(1H-imidazol-1-yl)propyl]amino}-1,3,4-thiadiazol-2-yl)benzamide | 397 | 65.6 |
| 100 | (E)-N-{5-[(3,4-dimethoxybenzyl)amino]-1,3,4-thiadiazol-2-yl}-9-octadecenamide | — | 65.1 |
| 101 | 2,6-dichloro-N-{5-[(1-naphthylmethyl)amino]-1,3,4-thiadiazol-2-yl}benzamide | 429 | 65.0 |
| 102 | 4-cyano-N-(5-{[2-(2-thienyl)ethyl]amino}-1,3,4-thiadiazol-2-yl)benzamide | 356 | 64.9 |
| 103 | 4-cyano-N-[5-(cycloheptylamino)-1,3,4-thiadiazol-2-yl]benzamide | 342 | 64.9 |
| 104 | N-[5-(cycloheptylamino)-1,3,4-thiadiazol-2-yl]-5-nitro-2-furamide | 352 | 64.7 |
| 105 | (E)-N-[5-(phenethylamino)-1,3,4-thiadiazol-2-yl]-9-octadecenamide, | 485 | 64.6 |
| 106 | 5-chloro-N-[5-(undecylamino)-1,3,4-thiadiazol-2-yl]pentanamide, | 389 | 64.2 |
| 107 | (E)-N-[5-(1,2,3,4-tetrahydro-1-naphthalenylamino)-1,3,4-thiadiazol-2-yl]-9-octadecenamide | 511 | 63.8 |
| 108 | (E)-N-{5-[(4-phenylbutyl)amino]-1,3,4-thiadiazol-2-yl}-9-octadecenamide | 513 | 63.5 |
| 109 | 2,4,6-triisopropyl-N-(5-{[2-(1-methyl-2-pyrrolidinyl)ethyl]amino]-1,3,4-thiadiazol-2-yl)benzamide | 458 | 63.4 |
| 110 | (E)-N-{5-[(1-benzyl-4-piperidinyl)amino]-1,3,4-thiadiazol-2-yl}-3-(2-chlorophenyl)-2-propenamide | 454 | 62.9 |
| 111 | 4-[({5-[(2,2-diphenylethyl)amino]-1,3,4-thiadiazol-2-yl}amino)carbonyl]benzenesulfonyl fluoride | 483 | 62.6 |
| 112 | N-(5-{[3-(cyclohexylamino)propyl]amino}-1,3,4-thiadiazol-2-yl)-4-(trifluoromethyl)benzamide | 428 | 62.5 |
| 113 | (E)-N-{5-[(cyclopropylmethyl)amino]-1,3,4-thiadiazol-2-yl}-9-octadecenamide | 435 | 62.2 |
| 114 | (E)-3-phenyl-N-(5-{[2-(phenylsulfanyl)ethyl]amino}-1,3,4-thiadiazol-2-yl)-2-propenamide | 383 | 62.1 |
| 115 | 2,6-dichloro-N-[5-(2,3-dihydro-1H-inden-1-ylamino)-1,3,4-thiadiazol-2-yl]benzamide | 405 | 62.0 |
| 116 | N-{5-[(2-ethylhexyl)amino]-1,3,4-thiadiazol-2-yl}-1,3-dioxo-1,3-dihydro-2-benzofuran-5-carboxamide | 401 | 61.9 |
| 117 | (E)-N-{5-[(1,3-benzodioxol-5-ylmethyl)amino]-1,3,4-thiadiazol-2-yl}-3-(2-chlorophenyl)-2-propenamide | 415 | 61.5 |
| 118 | 2,6-dichloro-N-{5-[(2-thienylmetyl)amino]-1,3,4-thiadiazol-2-yl}benzamide | 385 | 61.2 |
| 119 | (E)-N-{5-[(1-naphthylmethyl)amino]-1,3,4-thiadiazol-2-yl}-9-octadecenamide | 521 | 60.6 |
| 120 | tert-butyl 3-[(5-{[(E)-3-phenyl-2-propenoyl]amino}-1,3,4-thiadiazol-2-yl)amino]propanoate | 375 | 60.0 |
| 121 | 2,4-difluoro-N-[5-(undecylamino)-1,3,4-thiadiazol-2-yl]benzamide | 411 | 60.0 |
| 122 | N-{5-[(3,4-dimethoxybenzyl)amino]-1,3,4-thiadiazol-2-yl}-2-ethoxy-1-naphthamide | 465 | 59.5 |
| 123 | (E)-N-(5-{[2-(acetylamino)ethyl]amino}-1,3,4-thiadiazol-2-yl)-9-octadecenamide | 466 | 59.2 |
| 124 | (E)-N-(5-{[3-(cyclohexylamino)propyl]amino}-1,3,4-thiadiazol-2-yl)-3-phenyl-2-propenamide | 386 | 59.2 |
| 125 | (E)-N-(5-{[4-(aminosulfonyl)phenethyl]amino}-1,3,4-thiadizol-2-yl)-3-(2-chlorophenyl)-2-propenamide | 464 | 58.9 |
| 126 | N-(5-{[3-(cyclohexylamino)propyl]amino}-1,3,4-thiadiazol-2-yl)-5-nitro-2-furamide | 395 | 58.9 |
| 127 | 4-cyano-N-(5-{[3-(cyclohexylamino)propyl]amino-1,3,4-thiadiazol-2-yl)benzamide | 385 | 58.5 |
| 128 | N-(5-{[4-(aminosulfonyl)phenethyl]amino}1,3,4-thiadiazol-2-yl)-2,4,6-triisopropylbenzamide | 530 | 58.3 |
| 129 | (E)-N-(5-{[2-(ethylsulfanyl)ethyl]amino}1,3,4-thiadiazol-2-yl)-9-octadecenamide | 469 | 58.3 |
| 130 | (E)-N-(5-{[3-(2-oxo-1-pyrrolidinyl)propyl]amino}-1,3,4-thiadiazol-2-yl)-3-phenyl-2-propenamide | 372 | 58.2 |

TABLE 1-continued

| | | MS | % Inhib |
|---|---|---|---|
| 131 | 5-nitro-N-{5-[(4-phenylbutyl)amino]-1,3,4-thiadiazol-2-yl}-2-furamide | 388 | 58.0 |
| 132 | ethyl 4-({5-[(2,6-dichlorobenzoyl)amino]-1,3,4-thiadiazol-2-yl}amino)tetrahydro-1(2H)-pyridinecarboxylate | 444 | 57.0 |
| 133 | (E)-N-(5-{[3-(1H-imidazol-1-yl)propyl]amino}-1,3,4-thiadiazol-2-yl)-3-phenyl-2-propenamide | 355 | 57.0 |
| 134 | N-{5-[(3,4-dimethoxybenzyl)amino]-1,3,4-thiadiazol-2-yl}-4-iodobenzamide | 497 | 56.9 |
| 135 | 3-nitro-N-(5-{[3-(2-oxo-1-pyrrolidinyl)propyl]amino}-1,3,4-thiadiazol-2-yl)benzamide | 391 | 56.6 |
| 136 | 2-ethoxy-N-{5-[(1-naphthylmethyl)amino]-1,3,4-thiadiazol-2-yl}-1-naphthamide | 455 | 56.5 |
| 137 | N-(5-{[3-(cyclohexylamino)propyl]amino}-1,3,4-thiadiazol-2-yl)-3-nitrobenzamide | 405 | 56.4 |
| 138 | N-{5-[(4-phenylbutyl)amino]-1,3,4-thiadiazol-2-yl}-4-(trifluoromethyl)benzamide | 421 | 56.2 |
| 139 | (E)-3-phenyl-N-{5-[(2-pyridinylmethyl)amino]-1,3,4-thiadiazol-2-yl}-2-propenamide | 338 | 56.2 |
| 140 | 4-cyano-N-{5-[(3,4-dichlorobenzyl)amino]-1,3,4-thiadiazol-2-yl}benzamide | 404 | 56.2 |
| 141 | 2-ethoxy-N-(5-{[2-(1H-indol-3-yl)ethyl]amino}-1,3,4-thiadiazol-2-yl)-1-naphthamide | 458 | 55.7 |
| 142 | N-(5-{[4-(aminosulfonyl)phenethyl]amino}-1,3,4-thiadiazol-2-yl)-3,4-dichlorobenzamide | 472 | 55.4 |
| 143 | 4-cyano-N-{5-[(4-phenylbutyl)amino]-1,3,4-thiadiazol-2-yl}benzamide | 378 | 55.4 |
| 144 | 2,6-dichloro-N-{5-[(4-fluorobenzyl)amino]-1,3,4-thiadiazol-2-yl}benzamide | 397 | 55.2 |
| 145 | 2-ethoxy-N-[5-(undecylamino)-1,3,4-thiadiazol-2-yl]-1-naphthamide | 469 | 54.9 |
| 146 | 2,6-dichloro-N-{5-[(2-cyanoethyl)amino]-1,3,4-thiadiazol-2-yl}benzamide | 342 | 54.8 |
| 147 | 4-iodo-N-[5-(undecylamino)-1,3,4-thiadiazol-2-yl]benzamide | 501 | 54.7 |
| 148 | N-(5-{[2-(ethylsulfanyl)ethyl]amino}-1,3,4-thiadiazol-2-yl)-4-iodobenzamide | 435 | 54.6 |
| 149 | (E)-N-(5-{[2-(1H-indol-3-yl)ethyl]amino}-1,3,4-thiadiazol-2-yl)-9-octadecenamide | 524 | 54.5 |
| 150 | N-(5-{[3-(2-oxo-1-pyrrolidinyl)propyl]amino}-1,3,4-thiadiazol-2-yl)-1-benzothiophene-2-carboxamide | 402 | 54.5 |
| 151 | N-{5-[(1-benzyl-4-piperidinyl)amino]-1,3,4-thiadiazol-2-yl}-2,6-dichlorobenzamide | 462 | 54.0 |
| 152 | N-(5-{[4-(aminosulfonyl)phenethyl]amino}-1,3,4-thiadiazol-2-yl)-4-bromobenzamide | 484 | 53.9 |
| 153 | (E)-N-(5-{[2-(1H-indol-3-yl)ethyl]amino}-1,3,4-thiadiazol-2-yl)-3-phenyl-2-propenamide | 390 | 53.7 |
| 154 | (E)-3-(2-chlorophenyl)-N-{5-[(2,2-diphenylethyl)amino]-1,3,4-thiadiazol-2-yl}-2-propenamide | — | 53.6 |
| 155 | 4-cyano-N-{5-[(1-naphthylmethyl)amino]-1,3,4-thiadiazol-2-yl}benzamide | 386 | 53.3 |
| 156 | 2,6-dichloro-N-{5-[(3-pyridinylmethyl)amino]-1,3,4-thiadiazol-2-yl}benzamide | 380 | 53.2 |
| 157 | N-[5-(cycloheptylamino)-1,3,4-thiadiazol-2-yl]-2-ethoxy-1-naphthamide | 411 | 53.0 |
| 158 | 4-cyano-N-(5-{[3-(2-oxo-1-pyrrolidinyl)propyl]amino}-1,3,4-thiadiazol-2-yl)benzamide | 371 | 52.9 |
| 159 | 4-bromo-N-(5-{[3-(cyclohexylamino)propyl]amino}-1,3,4-thiadiazol-2-yl)benzamide | 440 | 52.8 |
| 160 | N-(5-{[3-(cyclohexylamino)propyl]amino}-1,3,4-thiadiazol-2-yl)-2,4-difluorobenzamide | 396 | 52.6 |
| 161 | (E)-3-(2-chlorophenyl)-N-{5-[(2-pyridinylmethyl)amino]-1,3,4-thiadiazol-2-yl}-2-propenamide | 372 | 51.9 |
| 162 | N-(5-{[3-(cyclohexylamino)propyl]amino}-1,3,4-thiadiazol-2-yl)-4-methylbenzamide | 374 | 51.8 |
| 163 | 4-bromo-N-(5-{[2-(phenylsulfanyl)ethyl]amino}-1,3,4-thiadiazol-2-yl)benzamide | 437 | 51.5 |
| 164 | (E)-3-(2-chlorophenyl)-N-{5-[(2-thienylmethyl)amino]-1,3,4-thiadiazol-2-yl}-2-propenamide | 377 | 51.4 |
| 165 | N-{5-[(1,3-benzodioxol-5-ylmethyl)amino]-1,3,4-thiadiazol-2-yl}-5-chloropentanamide | 369 | 51.3 |
| 166 | (E)-N-[5-({[(2R)-6,6-dimethylbicyclo[3.1.1]hept-2-yl]methyl}amino)-1,3,4-thiadiazol-2-yl]-9-octadecenamide | 517 | 51.1 |
| 167 | 4-methyl-N-[5-(undecylamino)-1,3,4-thiadiazol-2-yl]benzamide | 389 | 50.8 |
| 168 | 3,4-dichloro-N-{5-[(4-phenylbutyl)amino]-1,3,4-thiadiazol-2-yl}benzamide | 421 | 50.8 |

TABLE 1-continued

| | | MS | % Inhib |
|---|---|---|---|
| 169 | 2,4,6-triisopropyl-N-(5-{[2-(1-pyrrolidinyl)ethyl]amino}-1,3,4-thiadiazol-2-yl)benzamide | 444 | 50.7 |
| 170 | 4-bromo-N-{5-[(4-phenylbutyl)amino]-1,3,4-thiadiazol-2-yl}benzamide | 433 | 50.5 |
| 171 | (E)-N-{5-[(2-pyridinylmethyl)amino]-1,3,4-thiadiazol-2-yl}-9-octadecenamide | 472 | 49.9 |
| 172 | 3,4-dichloro-N-(5-{[3-(cyclohexylamino)propyl]amino}-1,3,4-thiadiazol-2-yl)benzamide | 428 | 49.7 |
| 173 | 2,4,6-triisopropyl-N-{5-[(1-naphthylmethyl)amino]-1,3,4-thiadiazol-2-yl}benzamide | 487 | 49.5 |
| 174 | 2,6-dichloro-N-{5-[(2-furylmethyl)amino]-1,3,4-thiadiazol-2-yl}benzamide | 369 | 49.5 |
| 175 | 3,5-difluoro-N-[5-(undecylamino)-1,3,4-thiadiazol-2-yl]benzamide | 411 | 49.4 |
| 176 | N-{5-[(2,2-diphenylethyl)amino]-1,3,4-thiadiazol-2-yl}-2,4,6-triisopropylbenzamide | 527 | 49.4 |
| 177 | N-{5-[(cyclopropylmethyl)amino]-1,3,4-thiadiazol-2-yl}-2-ethoxy-1-naphthamide | 369 | 49.0 |
| 178 | (E)-N-{5-[(1,3-benzodioxol-5-ylmethyl)amino]-1,3,4-thiadiazol-2-yl}-3-phenyl-2-propenamide | 381 | 49.0 |
| 179 | (E)-N-{5-[(2-anilinoethyl)amino]-1,3,4-thiadiazol-2-yl}-9-octadecenamide | 500 | 48.5 |
| 180 | N-{5-[(1,3-benzodioxol-5-ylmethyl)amino]-1,3,4-thiadiazol-2-yl}-1-benzothiophene-2-carboxamide | — | 48.4 |
| 181 | N-{5-[(1,3-benzodioxol-5-ylmethyl)amino]1,3,4-thiadiazol-2-yl}-4-methylbenzamide | 369 | 48.3 |
| 182 | N-{5-[(2,2-diphenylethyl)amino]-1,3,4-thiadiazol-2-yl}-2,4-difluorobenzamide | 437 | 48.2 |
| 183 | 5-chloro-N-{5-[(3,3-diphenylpropyl)amino]-1,3,4-thiadiazol-2-yl}pentanamide | 429 | 48.1 |
| 184 | 1,3-dioxo-N-(5-{[3-(2-oxo-1-pyrrolidinyl)propyl]amino}-1,3,4-thiadiazol-2-yl)-1,3-dihydro-2-benzofuran-5-carboxamide | 434 | 47.8 |
| 185 | (E)-3-(2-chlorophenyl)-N-(5-{[2-(2-thienyl)ethyl]amino}-1,3,4-thiadiazol-2-yl)-2-propenamide | 391 | 47.6 |
| 186 | 5-chloro-N-{5-[(2,2-diphenylethyl)amino]-1,3,4-thiadiazol-2-yl}pentanamide | 415 | 47.4 |
| 187 | N-{5-[(2,2-diphenylethyl)amino]-1,3,4-thiadiazol-2-yl}-1-benzothiophene-2-carboxamide | — | 47.2 |
| 188 | N-{5-[(2,2-diphenylethyl)amino]-1,3,4-thiadiazol-2-yl}-3,5-difluorobenzamide | 437 | 47.2 |
| 189 | 4-{[(5-{[3-(cyclohexylamino)propyl]amino}-1,3,4-thiadiazol-2-yl)amino]carbonyl}benzenesulfonyl fluoride | 442 | 47.1 |
| 190 | N-{5-[(1-naphthylmethyl)amino]-1,3,4-thiadiazol-2-yl}-3-nitrobenzamide | 406 | 47.1 |
| 191 | 3,4-dichloro-N-(5-{[3-(2-oxo-1-pyrrolidinyl)propyl]-amino}-1,3,4-thiadiazol-2-yl)benzamide | 414 | 47.1 |
| 192 | 5-nitro-N-[5-(1,2,3,4-tetrahydro-1-naphthalenylamino)-1,3,4-thiadiazol-2-yl]-2-furamide | 386 | 47.0 |
| 193 | (E)-3-(2-chlorophenyl)-N-(5-{[2-(ethylsulfanyl)ethyl]amino}-1,3,4-thiadiazol-2-yl)-2-propenamide | 369 | 46.9 |
| 194 | 4-bromo-N-[5-(undecylamino)-1,3,4-thiadiazol-2-yl]benzamide | 455 | 46.8 |
| 195 | 4-[({5-[(1-naphthylmethyl)amino]-1,3,4-thiadiazol-2-yl}amino)carbonyl]benzenesulfonyl fluoride | 443 | 46.7 |
| 196 | (E)-3-(2-chlorophenyl)-N-[5-(cycloheptylamino) 1,3,4-thiadiazol-2-yl]-2-propenamide | 377 | 46.2 |
| 197 | 2,4-difluoro-N-{5-[(4-phenylbutyl)amino]-1,3,4-thiadiazol-2-yl}benzamide | 389 | 46.2 |
| 198 | 4-iodo-N-(5-{[2-(phenylsulfanyl)ethyl]amino}-1,3,4-thiadiazol-2-yl)benzamide | — | 46.0 |
| 199 | (E)-N-[5-(cyclobutylamino)-1,3,4-thiadiazol-2-yl]-9-octadecenamide | 435 | 46.0 |
| 200 | 5-chloro-N-{5-[(1-naphthylmethyl)amino]-1,3,4-thiadiazol-2-yl}pentanamide | 375 | 45.3 |
| 201 | N-[5-(cycloheptylamino)-1,3,4-thiadiazol-2-yl]-3-nitrobenzamide | 362 | 45.3 |
| 202 | 3,4-dichloro-N-(5-{[3-(1H-imidazol-1-yl)propyl]amino}-1,3,4-thiadiazol-2-yl)benzamide | 397 | 45.0 |
| 203 | 4-iodo-N-(5-{[3-(2-oxo-1-pyrrolidinyl)propyl]amino}-1,3,4-thiadiazol-2-yl)benzamide | 472 | 45.0 |
| 204 | 4-[({5-[(2-anilinoethyl)amino]-1,3,4-thiadiazol-2-yl}amino)carbonyl]benzenesulfonyl fluoride | 422 | 45.0 |
| 205 | 2,4-difluoro-N-(5-{[2-(phenylsulfanyl)ethyl]amino}-1,3,4-thiadiazol-2-yl)benzamide | 393 | 44.9 |
| 206 | 2-ethoxy-N-(5-{[2-(phenylsulfanyl)ethyl]amino}-1,3,4-thiadiazol-2-yl)-1-naphthamide | 451 | 44.9 |

TABLE 1-continued

| | | MS | % Inhib |
|---|---|---|---|
| 207 | N-{5-[(3,4-dichlorobenzyl)amino]-1,3,4-thiadiazol-2-yl}-2-ethoxy-1-naphthamide | 473 | 44.7 |
| 208 | (E)-3-(2-chlorophenyl)-N-(5-{[3-(2-oxo-1-pyrrolidinyl)-propyl]amino}-1,3,4-thiadiazol-2-yl)-2-propenamide | 406 | 44.7 |
| 209 | N-[5-({[(2R)-6,6-dimethylbicyclo[3.1.1]hept-2-yl]methyl}-amino)-1,3,4-thiadiazol-2-yl]-5-nitro-2-furamide | 392 | 44.7 |
| 210 | (E)-3-(2-chlorophenyl)-N-[5-(phenethylamino)-1,3,4-thiadiazol-2-yl]-2-propenamide | 385 | 44.6 |
| 211 | (E)-N-(5-{[2-(ethylsulfanyl)ethyl]amino}-1,3,4-thiadiazol-2-yl)-3-phenyl-2-propenamide | 335 | 44.3 |
| 212 | N-(5-{[3-(cyclohexylamino)propyl]amino}-1,3,4-thiadiazol-2-yl)-4-iodobenzamide | 486 | 44.2 |
| 213 | 2-ethoxy-N-{5-[(2-furylmethyl)amino]-1,3,4-thiadiazol-2-yl}-1-naphthamide | 395 | 44.2 |
| 214 | N-{5-[(1-naphthylmethyl)amino]-1,3,4-thiadiazol-2-yl}-1-benzothiophene-2-carboxamide | — | 44.1 |
| 215 | (E)-N-(5-{[2-(1H-imidazol-4-yl)ethyl]amino}-1,3,4-thiadiazol-2-yl)-3-phenyl-2-propenamide | 341 | 44.1 |
| 216 | (E)-3-(2-chlorophenyl)-N-[5-(undecylamino)-1,3,4-thiadiazol-2-yl]-2-propenamide | — | 43.9 |
| 217 | 4-[({5-[(3,3-diphenylpropyl)amino]-1,3,4-thiadiazol-2-yl}amino)carbonyl]benzenesulfonyl fluoride | 497 | 43.9 |
| 218 | N-{5-[(1-benzyl-4-piperidinyl)amino]-1,3,4-thiadiazol-2-yl}-1-benzothiophene-2-carboxamide | 450 | 43.6 |
| 219 | N-(5-{[2-(1H-indol-3-yl)ethyl]amino}-1,3,4-thiadiazol-2-yl)-2,4,6-triisopropylbenzamide | 490 | 43.6 |
| 220 | (E)-N-{5-[(2-morpholinoethyl)amino]-1,3,4-thiadiazol-2-yl}-3-phenyl-2-propenamide | 360 | 43.6 |
| 221 | (E)-3-(2-chlorophenyl)-N-(5-{[3-(1H-imidazol-1-yl)propyl]amino}-1,3,4-thiadiazol-2-yl)-2-propenamide | 389 | 43.5 |
| 222 | N-{5-[(4-pyridinylmethyl)amino]-1,3,4-thiadiazol-2-yl}-1-benzothiophene-2-carboxamide | 368 | 43.2 |
| 223 | N-(5-{[4-(aminosulfonyl)benzyl]amino}-1,3,4-thiadiazol-2-yl)-1-benzothiophene-2-carboxamide | 446 | 43.1 |
| 224 | N-{5-[(2,2-diphenylethyl)amino]-1,3,4-thiadiazol-2-yl}-2-methoxybenzamide | 431 | 43.0 |
| 225 | 2,6-dichloro-N-{5-[(4-phenylbutyl)amino]-1,3,4-thiadiazol-2-yl}benzamide | 421 | 42.9 |
| 226 | N-{5-[(3,3-diphenylpropyl)amino]-1,3,4-thiadiazol-2-yl}-3-nitrobenzamide | 460 | 42.9 |
| 227 | N-[5-(cyclopropylamino)-1,3,4-thiadiazol-2-yl]-2-ethoxy-1-naphthamide | 355 | 42.8 |
| 228 | 3,5-difluoro-N-(5-{[3-(2-oxo-1-pyrrolidinyl)propyl]amino}-1,3,4-thiadiazol-2-yl)benzamide | 382 | 42.8 |
| 229 | | 271 | 42.5 |
| 230 | N-(5-{[4-(aminosulfonyl)phenethyl]amino}-1,3,4-thiadiazol-2-yl)-4-methylbenzamide | 418 | 42.3 |
| 231 | 2-ethoxy-N-{5-[(4-phenylbutyl)amino]-1,3,4-thiadiazol-2-yl}-1-naphthamide | 447 | 42.3 |
| 232 | 2,4,6-triisopropyl-N-{5-[(2-piperidinoethyl)amino]-1,3,4-thiadiazol-2-yl}benzamide | 458 | 42.2 |
| 233 | 2-ethoxy-N-[5-(neopentylamino)-1,3,4-thiadiazol-2-yl]-1-naphthamide | 385 | 42.1 |
| 234 | N-(5-{[2-(2-thienyl)ethyl]amino}-1,3,4-thiadiazol-2-yl)-1-benzothiophene-2-carboxamide | 387 | 42.0 |
| 235 | | 257 | 41.8 |
| 236 | N-{5-[(2-anilinoethyl)amino]-1,3,4-thiadiazol-2-yl}-1-benzothiophene-2-carboxamide | 396 | 41.6 |
| 237 | N-{5-[(2-thienylmethyl)amino]-1,3,4-thiadiazol-2-yl}-1-benzothiophene-2-carboxamide | 373 | 41.5 |
| 238 | (E)-N-{5-[(2-furylmethyl)amino]-1,3,4-thiadiazol-2-yl}-9-octadecenamide | 461 | 41.5 |
| 239 | 4-(trifluoromethyl)-N-[5-(undecylamino)-1,3,4-thiadiazol-2-yl]benzamide | 443 | 41.4 |
| 240 | (E)-3-(2-chlorophenyl)-N-{5-[(3,3-diphenylpropyl)amino]-1,3,4-thiadiazol-2-yl}-2-propenamide | — | 41.3 |
| 241 | 2,6-dichloro-N-{5-[(2-pyridinylmethyl)amino]-1,3,4-thiadiazol-2-yl}benzamide | 380 | 41.3 |
| 242 | 2-ethoxy-N-(5-{[3-(1H-imidazol-1-yl)propyl]amino}-1,3,4-thiadiazol-2-yl)-1-naphthamide | 423 | 41.3 |
| 243 | N-{5-[(3,3-diphenylpropyl)amino]-1,3,4-thiadiazol-2-yl}-2,4-difluorobenzamide | 451 | 41.1 |
| 244 | 4-cyano-N-{5-[(3,4-dimethoxybenzyl)amino]-1,3,4-thiadiazol-2-yl}benzamide | 396 | 41.0 |
| 245 | 4-[({5-[(4-phenylbutyl)amino]-1,3,4-thiadiazol-2-yl}amino)carbonyl]benzenesulfonyl fluoride | 435 | 41.0 |

TABLE 1-continued

| | | MS | % Inhib |
|---|---|---|---|
| 246 | (E)-N-{5-[(tetrahydro-2-furanylmethyl)amino]-1,3,4-thiadiazol-2-yl}-9-octadecenamide | 465 | 40.9 |
| 247 | 3,4-dichloro-N-{5-[(2-furylmethyl)amino]-1,3,4-thiadiazol-2-yl}benzamide | 369 | 40.9 |
| 248 | N-{5-[(2-anilinoethyl)amino]-1,3,4-thiadiazol-2-yl}-2,4,6-triisopropylbenzamide | 466 | 40.8 |
| 249 | (E)-N-{5-[(2-cyanoethyl)amino]-1,3,4-thiadiazol-2-yl}-9-octadecenamide | 432 | 40.6 |
| 250 | N-[5-(cycloheptylamino)-1,3,4-thiadiazol-2-yl]-2,4,6-triisopropylbenzamide | 443 | 40.5 |
| 251 | (E)-3-(2-chlorophenyl)-N-{5-[(2-furylmethyl)amino]-1,3,4-thiadiazol-2-yl}-2-propenamide | 361 | 40.3 |
| 252 | N-(5-{[2-(1H-indol-3-yl)ethyl]amino}-1,3,4-thiadiazol-2-yl)-4-iodobenzamide | 490 | 40.2 |
| 253 | (E)-N-{5-[(1-benzyl-4-piperidinyl)amino]-1,3,4-thiadiazol-2-yl}-9-octadecenamide | 554 | 40.1 |
| 254 | 5-chloro-N-(5-{[2-(phenylsulfanyl)ethyl]amino}-1,3,4-thiadiazol-2-yl)pentanamide | 371 | 40.0 |
| 255 | 2,6-dichloro-N-(5-{[2-(1H-indol-3-yl)ethyl]amino}-1,3,4-thiadiazol-2-yl)benzamide | 432 | 39.9 |
| 256 | N-[5-(cycloheptylamino)-1,3,4-thiadiazol-2-yl]-1-benzothiophene-2-carboxamide | 373 | 39.8 |
| 257 | N-[5-(undecylamino)-1,3,4-thiadiazol-2-yl]-1-benzothiophene-2-carboxamide | — | 39.8 |
| 258 | N-(5-{[2-(acetylamino)ethyl]amino}-1,3,4-thiadiazol-2-yl)-1,3-dioxo-1,3-dihydro-2-benzofuran-5-carboxamide | 376 | 39.7 |
| 259 | N-(5-{[4-(aminosulfonyl)phenethyl]amino}-1,3,4-thiadiazol-2-yl)-2,6-dichlorobenzamide | 472 | 39.6 |
| 260 | 2,4,6-triisopropyl-N-{5-[(4-phenylbutyl)amino]-1,3,4-thiadiazol-2-yl}benzamide | 479 | 39.6 |
| 261 | N-[5-({[(2R)-6,6-dimethylbicyclo[3.1.1]hept-2-yl]methyl}amino)-1,3,4-thiadiazol-2-yl]-2-ethoxy-1-naphthamide | 451 | 39.5 |
| 262 | (E)-N-[5-(phenethylamino)-1,3,4-thiadiazol-2-yl]-3-phenyl-2-propenamide | 351 | 39.5 |
| 263 | 3,4-chloro-N-{5-[(4-pyridinylmethyl)amino]-1,3,4-thiadiazol-2-yl}benzamide | 380 | 39.4 |
| 264 | N-{5-[(2-anilinoethyl)amino]-1,3,4-thiadiazol-2-yl}-5-nitro-2-furamide | 375 | 39.2 |
| 265 | N-{5-[(1-benzyl-4-piperidinyl)amino]-1,3,4-thiadiazol-2-yl}-2,4,6-triisopropylbenzamide | 520 | 39.1 |
| 266 | 2,4,6-triisopropyl-N-{5-[(4-pyridinylmethyl)amino]-1,3,4-thiadiazol-2-yl}benzamide | 438 | 38.8 |
| 267 | N-(5-{[4-(aminosulfonyl)phenethyl]amino}-1,3,4-thiadiazol-2-yl)-1-benzothiophene-2-carboxamide | 460 | 38.7 |
| 268 | (E)-3-(2-chlorophenyl)-N-(5-{[2-(1H-indol-3-yl)ethyl]amino}-1,3,4-thiadiazol-2-yl)-2-propenamide | — | 38.7 |
| 269 | N-(5-{[2-(1H-indol-3-yl)ethyl]amino}-1,3,4-thiadiazol-2-yl)-1-benzothiophene-2-carboxamide | — | 38.5 |
| 270 | 2-ethoxy-N-[5-(phenethylamino)-1,3,4-thiadiazol-2-yl]-1-naphthamide | 419 | 38.4 |
| 271 | N-(5-{[2-(1H-indol-3-yl)ethyl]amino}-1,3,4-thiadiazol-2-yl)-3-nitrobenzamide | 409 | 38.4 |
| 272 | 4-bromo-N-(5-{[3-(1H-imidazol-1-yl)propyl]amino}-1,3,4-thiadiazol-2-yl)benzamide | 409 | 38.2 |
| 273 | N-{5-[(1,3-benzodioxol-5-ylmethyl)amino]-1,3,4-thiadiazol-2-yl}-4-bromobenzamide | 435 | 38.1 |
| 274 | (E)-N-[5-(cycloheptylamino)-1,3,4-thiadiazol-2-yl]-3-phenyl-2-propenamide | 343 | 38.1 |
| 275 | N-(5-{[3-(cyclohexylamino)propyl]amino}-1,3,4-thiadiazol-2-yl)-3,5-difluorobenzamide | 396 | 37.9 |
| 276 | (E)-3-(2-chlorophenyl)-N-[5-(cyclobutylamino)-1,3,4-thiadiazol-2-yl]-2-propenamide | 335 | 37.9 |
| 277 | N-{5-[(3,3-diphenylpropyl)amino]-1,3,4-thiadiazol-2-yl}-1-benzothiophene-2-carboxamide | — | 37.9 |
| 278 | 4-({[5-(cycloheptylamino)-1,3,4-thiadiazol-2-yl]amino}carbonyl)benzenesulfonyl fluoride | 399 | 37.5 |
| 279 | (E)-N-[5-(2,3-dihydro-1H-inden-1-ylamino)-1,3,4-thiadiazol-2-yl]-9-octadecenamide | 497 | 37.4 |
| 280 | 2,6-dichloro-N-{5-[(3,4-dimethoxybenzyl)amino]-1,3,4-thiadiazol-2-yl}benzamide | 439 | 37.3 |
| 281 | N-{5-[(3,3-diphenylpropyl)amino]-1,3,4-thiadiazol-2-yl}-3,5-difluorobenzamide | 451 | 37.3 |
| 282 | 5-nitro-N-[5-(phenethylamino)-1,3,4-thiadiazol-2-yl]-2-furamide | 360 | 37.1 |
| 283 | 2,6-dichloro-N-{5-[(2-ethylhexyl)amino]-1,3,4-thiadiazol-2-yl}benzamide | 401 | 37.0 |

TABLE 1-continued

|   |   | MS | % Inhib |
|---|---|---|---|
| 284 | N-(5-{[2-(1H-indol-3-yl)ethyl]amino}-1,3,4-thiadiazol-2-yl)-4-(trifluoromethyl)benzamide | 432 | 36.7 |
| 285 | (E)-N-{5-[(cyclohexylmethyl)amino]-1,3,4-thiadiazol-2-yl}-9-octadecenamide | 477 | 36.7 |
| 286 | (E)-N-{5-[(2-ethylhexyl)amino]-1,3,4-thiadiazol-2-yl}-9-octadecenamide | 493 | 36.3 |
| 287 | N-[5-(cyclopropylamino)-1,3,4-thiadiazol-2-yl]-1-benzothiophene-2-carboxamide | 317 | 36.2 |
| 288 | N-[5-(cycloheptylamino)-1,3,4-thiadiazol-2-yl]-4-iodobenzamide | 443 | 36.2 |
| 289 | 4-iodo-N-{5-[(4-pyridinylmethyl)amino]-1,3,4-thiadiazol-2-yl}benzamide | 438 | 36.0 |
| 290 | (E)-N-{5-[(1-benzyl-4-piperidinyl)amino]-1,3,4-thiadiazol-2-yl}-3-phenyl-2-propenamide | 420 | 35.9 |
| 291 | N-{5-[(2-anilinoethyl)amino]-1,3,4-thiadiazol-2-yl}-3-nitrobenzamide | 385 | 35.7 |
| 292 | 2,6-dichloro-N-(5-{[2-(ethylsulfanyl)ethyl]amino}-1,3,4-thiadiazol-2-yl)benzamide | 377 | 35.6 |
| 293 | tert-butyl 3-[(5-{[(2-ethoxy-1-naphthyl)carbonyl]amino}-1,3,4-thiadiazol-2-yl)amino]propanoate | 443 | 35.5 |
| 294 | (E)-N-{5-[(2-anilinoethyl)amino]-1,3,4-thiadiazol-2-yl}-3-(2-chlorophenyl)-2-propenamide | 400 | 35.4 |
| 295 | 3,4-dichloro-N-(5-{[2-(1H-indol-3-yl)ethyl]amino}-1,3,4-thiadiazol-2-yl)benzamide | — | 35.4 |
| 296 | 5-nitro-N-(5-{[3-(2-oxo-1-pyrrolidinyl)propyl]amino}-1,3,4-thiadiazol-2-yl)-2-furamide | 381 | 35.1 |
| 297 | N-{5-[(3,3-diphenylpropyl)amino]-1,3,4-thiadiazol-2-yl}-4-iodobenzamide | — | 35.0 |
| 298 | N-{5-[(3,3-diphenylpropyl)amino]-1,3,4-thiadiazol-2-yl}-5-nitro-2-furamide | 450 | 35.0 |
| 299 | N-{5-[(3,3-diphenylpropyl)amino]-1,3,4-thiadiazol-2-yl}-2,4,6-triisopropylbenzamide | 541 | 34.9 |
| 300 | N-[5-(cycloheptylamino)-1,3,4-thiadiazol-2-yl]-3,5-difluorobenzamide | 353 | 34.9 |
| 301 | N-{5-[(3-pyridinylmethyl)amino]-1,3,4-thiadiazol-2-yl}-1-benzothiophene-2-carboxamide | 368 | 34.8 |
| 302 | N-{5-[(4-fluorobenzyl)amino]-1,3,4-thiadiazol-2-yl}-3-nitrobenzamide | 374 | 34.8 |
| 303 | N-(5-{[2-(1H-indol-3-yl)ethyl]amino}-1,3,4-thiadiazol-2-yl)-2-methoxybenzamide | 394 | 34.7 |
| 304 | N-{5-[(cyclohexylmethyl)amino]-1,3,4-thiadiazol-2-yl}-2-methoxybenzamide | 347 | 34.6 |
| 305 | N-{5-[(1,3-benzodioxol-5-ylmethyl)amino]-1,3,4-thiadiazol-2-yl}-2,4-difluorobenzamide | 391 | 34.5 |
| 306 | N-{5-[(2,2-diphenylethyl)amino]-1,3,4-thiadiazol-2-yl}-5-nitro-2-furamide | 436 | 34.4 |
| 307 | 4-cyano-N-[5-({[(2R)-6,6-dimethylbicyclo[3.1.1]hept-2-yl]methyl}amino)-1,3,4-thiadiazol-2-yl]benzamide | 382 | 34.2 |
| 308 | 2,4-dichloro-N-[5-(phenethylamino)-1,3,4-thiadiazol-2-yl]benzamide | 393 | 34.2 |
| 309 | 4-bromo-N-(5-{[2-(ethylsulfanyl)ethyl]amino}-1,3,4-thiadiazol-2-yl)benzamide | 389 | 34.0 |
| 310 | N-[5-(cycloheptylamino)-1,3,4-thiadiazol-2-yl]-2-methoxybenzamide | 347 | 34.0 |
| 311 | N-(5-{[4-(aminosulfonyl)benzyl]amino}-1,3,4-thiadiazol-2-yl)-3,4-dichlorobenzamide | 458 | 33.9 |
| 312 | 5-chloro-N-[5-({[(2R)-6,6-dimethylbicyclo[3.1.1]hept-2-yl]methyl}amino)-1,3,4-thiadiazol-2-yl]pentanamide | 371 | 33.9 |
| 313 | (E)-N-{5-[(3,4-dichlorobenzyl)amino]-1,3,4-thiadiazol-2-yl}-9-octadecenamide | 539 | 33.9 |
| 314 | N-[5-(cyclobutylamino)-1,3,4-thiadiazol-2-yl]-2-ethoxy-1-naphthamide | 369 | 33.8 |
| 315 | 5-chloro-N-{5-[(cyclohexylmethyl)amino]-1,3,4-thiadiazol-2-yl}pentanamide | 331 | 33.8 |
| 316 | 5-chloro-N-[5-(cycloheptylamino)-1,3,4-thiadiazol-2-yl]pentanamide | 331 | 33.6 |
| 317 | N-(5-{[2-(1H-imidazol-4-yl)ethyl]amino}-1,3,4-thiadiazol-2-yl)-2,4,6-triisopropylbenzamide | 411 | 33.6 |
| 318 | 2-ethoxy-N-(5-{[2-(ethylsulfanyl)ethyl]amino}-1,3,4-thiadiazol-2-yl)-1-naphthamide | 403 | 33.6 |
| 319 | (E)-3-(2-chlorophenyl)-N-[5-(neopentylamino)-1,3,4-thiadiazol-2-yl]-2-propenamide | 351 | 33.5 |
| 320 | (E)-3-(2-chlorophenyl)-N-[5-({[(2R)-6,6-dimethylbicyclo[3.1.1]hept-2-yl]methyl}amino)-1,3,4-thiadiazol-2-yl]-2-propenamide | — | 33.5 |
| 321 | 5-chloro-N-{5-[(4-fluorobenzyl)amino]-1,3,4-thiadiazol-2-yl}pentanamide | 343 | 33.2 |

TABLE 1-continued

| | | MS | % Inhib |
|---|---|---|---|
| 322 | (E)-3-(2-chlorophenyl)-N-(5-{[2-(phenylsulfanyl)ethyl]amino}-1,3,4-thiadiazol-2-yl)-2-propenamide | — | 33.2 |
| 323 | N-[5-(cycloheptylamino)-1,3,4-thiadiazol-2-yl]-4-methylbenzamide | 331 | 33.0 |
| 324 | N-(5-{[3-(1H-imidazol-1-yl)propyl]amino}-1,3,4-thiadiazol-2-yl)-4-iodobenzamide | 455 | 32.9 |
| 325 | 5-chloro-N-(5-{[3-(2-oxo-1-pyrrolidinyl)propyl]amino}-1,3,4-thiadiazol-2-yl)pentanamide | 360 | 32.8 |
| 326 | (E)-N-{5-[(4-fluorobenzyl)amino]-1,3,4-thiadiazol-2-yl}-3-phenyl-2-propenamide | 355 | 32.7 |
| 327 | 2-methoxy-N-[5-(phenethylamino)-1,3,4-thiadiazol-2-yl]benzamide | 355 | 32.5 |
| 328 | N-(5-{[4-(aminosulfonyl)phenethyl]amino}-1,3,4-thiadiazol-2-yl)-2-ethoxy-1-naphthamide | 498 | 32.4 |
| 329 | (E)-N-{5-[(1-naphthylmethyl)amino]-1,3,4-thiadiazol-2-yl}-3-phenyl-2-propenamide | 387 | 32.4 |
| 330 | N-(5-{[2-(1H-imidazol-4-yl)ethyl]amino}-1,3,4-thiadiazol-2-yl-1-benzothiophene-2-carboxamide | 371 | 32.2 |
| 331 | (E)-N-{5-[(3,3-diphenylpropyl)amino]-1,3,4-thiadiazol-2-yl}-3-phenyl-2-propenamide | — | 32.1 |
| 332 | N-(5-{[2-(acetylamino)ethyl]amino}-1,3,4-thiadiazol-2-yl)-2,4,6-triisopropylbenzamide | 432 | 32.0 |
| 333 | (E)-N-{5-[(3,4-dichlorobenzyl)amino]-1,3,4-thiadiazol-2-yl}-3-phenyl-2-propenamide | 405 | 31.9 |
| 334 | 2-methoxy-N-{5-[(1-naphthylmethyl)amino]-1,3,4-thiadiazol-2-yl}benzamide | 391 | 31.8 |
| 335 | N-(5-{[4-(aminosulfonyl)phenethyl]amino}-1,3,4-thiadiazol-2-yl)-4-cyanobenzamide | 429 | 31.7 |
| 336 | (E)-N-(5-{[4-(aminosulfonyl)phenethyl]amino}-1,3,4-thiadiazol-2-yl)-9-octadecenamide | — | 31.6 |
| 337 | 3-nitro-N-(5-{[2-(2-thienyl)ethyl]amino}-1,3,4-thiadiazol-2-yl)benzamide | 376 | 31.6 |
| 338 | tert-butyl 3-({5-[(2,6-dichlorobenzoyl)amino]-1,3,4-thiadiazol-2-yl}amino)propanoate | 417 | 31.6 |
| 339 | N-{5-[(2-anilinoethyl)amino]-1,3,4-thiadiazol-2-yl}-4-iodobenzamide | 466 | 31.5 |
| 340 | tert-butyl 3-[(5-{[(1,3-dioxo-1,3-dihydro-2-benzofuran-5-yl)carbonyl]amino}-1,3,4-thiadiazol-2-yl)amino]propanoate | 419 | 31.5 |
| 341 | N-{5-[(2-furylmethyl)amino]-1,3,4-thiadiazol-2-yl}-4-iodobenzamide | 427 | 31.3 |
| 342 | (E)-3-phenyl-N-[5-(undecylamino)-1,3,4-thiadiazol-2-yl]-2-propenamide | 401 | 31.2 |
| 343 | N-[5-(1,2,3,4-tetrahydro-1-naphthalenylamino)-1,3,4-thiadiazol-2-yl]-1-benzothiophene-2-carboxamide | 407 | 31.2 |
| 344 | ethyl 4-[(5-(1,2,3,4-tetrahydro-1-naphthalenylamino)-1,3,4-1,3,4-thiadiazol-2-yl)amino]tetrahydro-1(2H)-pyridinecarboxylate | 436 | 31.1 |
| 345 | 4-cyano-N-[5-(phenethylamino)-1,3,4-thiadiazol-2-yl]benzamide | 350 | 30.9 |
| 346 | 5-chloro-N-(5-{[2-(1H-indol-3-yl)ethyl]amino}-1,3,4-thiadiazol-2-yl)pentanamide | 378 | 30.7 |
| 347 | 3-nitro-N-[5-(1,2,3,4-tetrahydro-1-naphthalenylamino)-1,3,4-thiadiazol-2-yl]benzamide | 396 | 30.6 |
| 348 | N-{5-[(4-fluorobenzyl)amino]-1,3,4-thiadiazol-2-yl}-2-methoxybenzamide | 359 | 30.4 |
| 349 | N-{5-[(2-furylmethyl)amino]-1,3,4-thiadiazol-2-yl}-1-benzothiophene-2-carboxamide | 357 | 30.3 |
| 350 | N-{5-[(3,4-dichlorobenzyl)amino]-1,3,4-thiadiazol-2-yl}-5-nitro-2-furamide | 414 | 30.3 |
| 351 | 4-bromo-N-(5-{[2-(1H-indol-3-yl)ethyl]amino}-1,3,4-thiadiazol-2-yl)benzamide | 444 | 30.3 |
| 352 | (E)-3-(2-chlorophenyl)-N-[5-[(4-pyridinylmethyl)amino]-1,3,4-thiadiazol-2-yl]-2-propenamide | 372 | 30.2 |
| 353 | (E)-3-(2-chlorophenyl)-N-[5-(cyclopropylamino)-1,3,4-thiadiazol-2-yl]-2-propenamide | 321 | 30.2 |
| 354 | 5-chloro-N-[5-(phenethylamino)-1,3,4-thiadiazol-2-yl]pentanamide | 339 | 29.9 |
| 355 | N-[5-(2,3-dihydro-1H-inden-1-ylamino)-1,3,4-thiadiazol-2-yl]-3-nitrobenzamide | 382 | 29.8 |
| 356 | 4-methyl-N-{5-[(4-phenylbutyl)amino]-1,3,4-thiadiazol-2-yl}benzamide | 367 | 29.6 |
| 357 | (E)-3-(2-chlorophenyl)-N-{5-[(4-phenylbutyl)amino]-1,3,4-thiadiazol-2-yl}-2-propenamide | — | 29.4 |
| 358 | N-{5-[(1,3-benzodioxol-5-ylmethyl)amino]-1,3,4-thiadiazol-2-yl}-2,4,6-triisopropylbenzamide | 481 | 29.3 |
| 359 | 4-methyl-N-[5-(phenethylamino)-1,3,4-thiadiazol-2-yl]benzamide | 339 | 29.1 |

TABLE 1-continued

|   |   | MS | % Inhib |
|---|---|---|---|
| 360 | (E)-N-{5-[(cyclohexylmethyl)amino]-1,3,4-thiadiazol-2-yl}-3-phenyl-2-propenamide | 343 | 29.0 |
| 361 | N-{5-[(4-fluorobenzyl)amino]-1,3,4-thiadiazol-2-yl}-1-benzothiophene-2-carboxamide | 385 | 28.8 |
| 362 | 3,5-difluoro-N-{5-[(1-naphthylmethyl)amino]-1,3,4-thiadiazol-2-yl}benzamide | 397 | 28.8 |
| 363 | 2,4-difluoro-N-{5-[(1-naphthylmethyl)amino]-1,3,4-thiadiazol-2-yl}benzamide | 397 | 28.8 |
| 364 | 4-cyano-N-{5-[(cyclohexylmethyl)amino]-1,3,4-thiadiazol-2-yl}benzamide | 342 | 28.7 |
| 365 | 4-cyano-N-{5-[(2-thienylmethyl)amino]-1,3,4-thiadiazol-2-yl}benzamide | 342 | 28.7 |
| 366 | N-(5-{[4-(aminosulfonyl)phenethyl]amino}-1,3,4-thiadiazol-2-yl)-2-methoxybenzamide | 434 | 28.6 |
| 367 | N-{5-[(1-benzyl-4-piperidinyl)amino]-1,3,4-thiadiazol-2-yl}-4-iodobenzamide | 520 | 28.6 |
| 368 | ethyl 4-({5-[(1-benzothiophen-2-ylcarbonyl)amino]-1,3,4-thiadiazol-2-yl}amino)tetrahydro-1(2H)-pyridinecarboxylate | 432 | 28.5 |
| 369 | 2,6-dichloro-N-[5-(cycloheptylamino)-1,3,4-thiadiazol-2-yl]benzamide | 385 | 28.3 |
| 370 | 2,6-dichloro-N-(5-{[2-(1-pyrrolidinyl)ethyl]amino}-1,3,4-thiadiazol-2-yl)benzamide | 386 | 28.3 |
| 371 | 4-{[(5-{[3-(2-oxo-1-pyrrolidinyl)propyl]amino}-1,3,4-thiadiazol-2-yl)amino]carbonyl}benzenesulfonyl fluoride | 428 | 28.1 |
| 372 | N-{5-[(1,3-benzodioxol-5-ylmethyl)amino]-1,3,4-thiadiazol-2-yl}-3,5-difluorobenzamide | 391 | 28.1 |
| 373 | 3,5-difluoro-N-{5-[(4-phenylbutyl)amino]-1,3,4-thiadiazol-2-yl}benzamide | 389 | 28.1 |
| 374 | (E)-3-(2-chlorophenyl)-N-[5-(1,2,3,4-tetrahydro-1-naphthalenylamino)-1,3,4-thiadiazol-2-yl]-2-propenamide | 411 | 28.1 |
| 375 | 3,4-dichloro-N-[5-(undecylamino)-1,3,4-thiadiazol-2-yl]benzamide | 443 | 27.9 |
| 376 | N-{5-[(3,3-diphenylpropyl)amino]-1,3,4-thiadiazol-2-yl}-4-(trifluoromethyl)benzamide | 483 | 27.9 |
| 377 | 2,6-dichloro-N-[5-(phenethylamino)-1,3,4-thiadiazol-2-yl]benzamide | 393 | 27.8 |
| 378 | (E)-N-(5-{[3-(1H-imidazol-1-yl)propyl]amino}-1,3,4-thiadiazol-2-yl)-9-octadecenamide | 489 | 27.8 |
| 379 | (E)-N-{5-[(2-anilinoethyl)amino]-1,3,4-thiadiazol-2-yl}-3-phenyl-2-propenamide | 366 | 27.5 |
| 380 | N-{5-[(cyclohexylmethyl)amino]-1,3,4-thiadiazol-2-yl}-5-nitro-2-furamide | 352 | 27.5 |
| 381 | 2,4,6-triisopropyl-N-(5-{[3-(2-oxo-1-pyrrolidinyl)propyl]amino}-1,3,4-thiadiazol-2-yl)benzamide | 472 | 27.4 |
| 382 | 5-chloro-N-{5-[(4-phenylbutyl)amino]-1,3,4-thiadiazol-2-yl}pentanamide | 367 | 27.3 |
| 383 | N-{5-[(3,3-diphenylpropyl)amino]-1,3,4-thiadiazol-2-yl}-2-methoxybenzamide | 445 | 27.3 |
| 384 | 3,4-dichloro-N-{5-[(cyclohexylmethyl)amino]-1,3,4-thiadiazol-2-yl}benzamide | 385 | 27.2 |
| 385 | 4-bromo-N-{5-[(2,2-diphenylethyl)amino]-1,3,4-thiadiazol-2-yl}benzamide | — | 27.2 |
| 386 | 4-bromo-N-{5-[(3,3-diphenylpropyl)amino]-1,3,4-thiadiazol-2-yl}benzamide | — | 26.9 |
| 387 | N-(5-{[3-(cyclohexylamino)propyl]amino}-1,3,4-thiadiazol-2-yl)-2-methoxybenzamide | 390 | 26.8 |
| 388 | tert-butyl 3-({5-[(2,4,6-triisopropylbenzoyl)amino]-1,3,4-thiadiazol-2-yl}amino)propanoate | 475 | 26.6 |
| 389 | N-[5-({[(2R)-6,6-dimethylbicyclo[3.1.1]hept-2-yl]methyl}amino)-1,3,4-thiadiazol-2-yl]-3,5-difluorobenzamide | 393 | 26.5 |
| 390 | N-(5-{[4-(aminosulfonyl)phenethyl]amino}-1,3,4-thiadiazol-2-yl)-5-chloropentanamide | 418 | 26.3 |
| 391 | (E)-N-(5-{[2-(1H-imidazol-4-yl)ethyl]amino}-1,3,4-thiadiazol-2-yl)-9-octadecenamide | 475 | 26.2 |
| 392 | 2,6-dichloro-N-[5-(neopentylamino)-1,3,4-thiadiazol-2-yl]benzamide | 359 | 26.2 |
| 393 | N-{5-[(2-anilinoethyl)amino]-1,3,4-thiadiazol-2-yl}-4-methylbenzamide | 354 | 26.1 |
| 394 | N-{5-[(2-anilinoethyl)amino]-1,3,4-thiadiazol-2-yl}-2-methoxybenzamide | 370 | 26.0 |
| 395 | 4-methyl-N-(5-{[3-(2-oxo-1-pyrrolidinyl)propyl]amino}-1,3,4-thiadiazol-2-yl)benzamide | 360 | 25.9 |
| 396 | 2,4,6-triisopropyl-N-(5-{[2-(2-thienyl)ethyl]amino}-1,3,4-thiadiazol-2-yl)benzamide | 457 | 25.9 |
| 397 | (E)-3-(2-chlorophenyl)-N-(5-{[2-(1-pyrrolidinyl)ethyl]amino}-1,3,4-thiadiazol-2-yl)-2-propenamide | 378 | 25.9 |

TABLE 1-continued

| | | MS | % Inhib |
|---|---|---|---|
| 398 | N-(5-{[4-(aminosulfonyl)benzyl]amino}-1,3,4-thiadiazol-2-yl)-4-(trifluoromethyl)benzamide | 458 | 25.9 |
| 399 | 2,4,6-triisopropyl-N-{5-[(3-pyridinylmethyl)amino]-1,3,4-thiadiazol-2-yl}benzamide | 438 | 25.8 |
| 400 | (E)-N-(5-{[2-(acetylamino)ethyl]amino}-1,3,4-thiadiazol-2-yl)-3-phenyl-2-propenamide | 332 | 25.8 |
| 401 | N-{5-[(4-fluorobenzyl)amino]-1,3,4-thiadiazol-2-yl}-2,4,6-triisopropylbenzamide | 455 | 25.5 |
| 402 | 4-iodo-N-{5-[(1-naphthylmethyl)amino]-1,3,4-thiadiazol-2-yl}benzamide | — | 25.5 |
| 403 | N-[5-({[(2R)-6,6-dimethylbicyclo[3.1.1]hept-2-yl]methyl}-amino)-1,3,4-thiadiazol-2-yl]-1-benzothiophene-2-carboxamide | — | 25.3 |
| 404 | N-[5-(2,3-dihydro-1H-inden-1-ylamino)-1,3,4-thiadiazol-2-yl]-5-nitro-2-furamide | 372 | 25.2 |
| 405 | N-{5-[(tetrahydro-2-furanylmethyl)amino]-1,3,4-thiadiazol-2-yl}-1-benzothiophene-2-carboxamide | 361 | 25.0 |
| 406 | N-(5-{[2-(ethylsulfanyl)ethyl]amino}-1,3,4-thiadiazol-2-yl)-4-(trifluoromethyl)benzamide | 377 | 25.0 |
| 407 | tert-butyl 3-[(5-{[4-(trifluoromethyl)benzoyl]amino}-1,3,4-thiadiazol-2-yl)amino]propanoate | 417 | 25.0 |
| 408 | N-{5-[(2-anilinoethyl)amino]-1,3,4-thiadiazol-2-yl}-3,4-dichlorobenzamide | 408 | 24.9 |
| 409 | N-{5-[(cyclohexylmethyl)amino]-1,3,4-thiadiazol-2-yl}-2,4,6-triisopropylbenzamide | 443 | 24.9 |
| 410 | 2,6-dichloro-N-[5-(undecylamino)-1,3,4-thiadiazol-2-yl]benzamide | 443 | 24.9 |
| 411 | 3-nitro-N-[5-(phenethylamino)-1,3,4-thiadiazol-2-yl]benzamide | 370 | 24.8 |
| 412 | N-(5-{[2-(acetylamino)ethyl]amino}-1,3,4-thiadiazol-2-yl)-1-benzothiophene-2-carboxamide | 362 | 24.7 |
| 413 | 3-nitro-N-{5-[(4-phenylbutyl)amino]-1,3,4-thiadiazol-2-yl}benzamide | 398 | 24.7 |
| 414 | N-{5-[(1,3-benzodioxol-5-ylmethyl)amino]-1,3,4-thiadiazol-2-yl}-2-methoxybenzamide | 385 | 24.7 |
| 415 | 4-iodo-N-[5-(phenethylamino)-1,3,4-thiadiazol-2-yl]benzamide | 451 | 24.6 |
| 416 | N-{5-[(3,4-dichlorobenzyl)amino]-1,3,4-thiadiazol-2-yl}-2,4-difluorobenzamide | 415 | 24.5 |
| 417 | 3,4-dichloro-N-{5-[(3-pyridinylmethyl)amino]-1,3,4-thiadiazol-2-yl}benzamide | 380 | 24.4 |
| 418 | 3,4-dichloro-N-[5-(cycloheptylamino)-1,3,4-thiadiazol-2-yl]benzamide | 385 | 24.4 |
| 419 | 4-bromo-N-(5-{[3-(2-oxo-1-pyrrolidinyl)propyl]amino}-1,3,4-thiadiazol-2-yl)benzamide | 426 | 24.3 |
| 420 | tert-butyl 3-({5-[(3,4-dichlorobenzoyl)amino]-1,3,4-thiadiazol-2-yl}amino)propanoate | 417 | 24.1 |
| 421 | (E)-3-phenyl-N-{5-[(3-pyridinylmethyl)amino]-1,3,4-thiadiazol-2-yl}-2-propenamide | 338 | 24.0 |
| 422 | (E)-3-(2-chlorophenyl)-N-(5-{[3-(4-methylpiperazino)-propyl]amino}-1,3,4-thiadiazol-2-yl)-2-propenamide | 421 | 24.0 |
| 423 | 2,4-difluoro-N-{5-[(4-fluorobenzyl)amino]-1,3,4-thiadiazol-2-yl}benzamide | 365 | 23.8 |
| 424 | 2,4,6-triisopropyl-N-{5-[(2-thienylmethyl)amino]-1,3,4-thiadiazol-2-yl}benzamide | 443 | 23.6 |
| 425 | 4-iodo-N-{5-[(2-thienylmethyl)amino]-1,3,4-thiadiazol-2-yl}benzamide | 443 | 23.5 |
| 426 | tert-butyl 3-[(5-{[(E)-3-(2-chlorophenyl)-2-propenoyl]-amino}-1,3,4-thiadiazol-2-yl)amino]propanoate | 409 | 23.5 |
| 427 | 2,4-difluoro-N-(5-{[3-(2-oxo-1-pyrrolidinyl)propyl]-amino}-1,3,4-thiadiazol-2-yl)benzamide | 382 | 23.4 |
| 428 | 2-methoxy-N-[5-(1,2,3,4-tetrahydro-1-naphthalenylamino)-1,3,4-thiadiazol-2-yl]benzamide | 381 | 23.3 |
| 429 | 2-methoxy-N-{5-[(4-phenylbutyl)amino]-1,3,4-thiadiazol-2-yl}benzamide | 383 | 23.2 |
| 430 | 4-iodo-N-(5-{[2-(2-thienyl)ethyl]amino}-1,3,4-thiadiazol-2-yl)benzamide | 457 | 23.1 |
| 431 | N-{5-[(cyclohexylmethyl)amino]-1,3,4-thiadiazol-2-yl}-2-ethoxy-1-naphthamide | 411 | 23.1 |
| 432 | (E)-3-phenyl-N-(5-{[2-(1-pyrrolidinyl)ethyl]amino}-1,3,4-thiadiazol-2-yl)-2-propenamide | 344 | 23.0 |
| 433 | N-{5-[(cyclohexylmethyl)amino]-1,3,4-thiadiazol-2-yl}-2,4-difluorobenzamide | 353 | 22.9 |
| 434 | N-{5-[(2-anilioethyl)amino]-1,3,4-thiadiazol-2-yl}-4-bromobenzamide | 420 | 22.8 |
| 435 | N-{5-[(2-cyanoethyl)amino]-1,3,4-thiadiazol-2-yl}-2,4,6-triisopropylbenzamide | 400 | 22.8 |
| 436 | N-{5-[(3,4-dimethoxybenzyl)amino]-1,3,4-thiadiazol-2-yl}-3-nitrobenzamide | 416 | 22.8 |

TABLE 1-continued

| | | MS | % Inhib |
|---|---|---|---|
| 437 | 3,5-difluoro-N-[5-(phenethylamino)-1,3,4-thiadiazol-2-yl]benzamide | 361 | 22.7 |
| 438 | N-{5-[(2-anilinoethyl)amino]-1,3,4-thiadiazol-2-yl}-2,6-dichlorobenzamide | 408 | 22.6 |
| 439 | (E)-3-(2-chlorophenyl)-N-{5-[(cyclohexylmethyl)amino]-1,3,4-thiadiazol-2-yl}-2-propenamide | 377 | 22.5 |
| 440 | N-[5-({[(2R)-6,6-dimethylbicyclo[3.1.1]hept-2-yl]methyl}amino)-1,3,4-thiadiazol-2-yl]-2,4,6-triisopropylbenzamide | 483 | 22.5 |
| 441 | 2,4,6-triisopropyl-N-[5-(undecylamino)-1,3,4-thiadiazol-2-yl]benzamide | 501 | 22.5 |
| 442 | N-{5-[(2-furylmethyl)amino]-1,3,4-thiadiazol-2-yl}-2,4,6-triisopropylbenzamide | 427 | 22.3 |
| 443 | (E)-3-(2-chlorophenyl)-N-{5-[(1-naphthylmethyl)amino]-1,3,4-thiadiazol-2-yl}-2propenamide | — | 22.1 |
| 444 | N-(5-{[2-(dimethylamino)ethyl]amino}-1,3,4-thiadiazol-2-yl)-2,4,6-triisopropylbenzamide | 418 | 21.9 |
| 445 | 2,4-difluoro-N-(5-{[2-(2-thienyl)ethyl]amino}-1,3,4-thiadiazol-2-yl)benzamide | 367 | 21.9 |
| 446 | N-(5-{[4-(aminosulfonyl)phenethyl]amino}-1,3,4-thiadiazol-2-yl)-4-(trifluoromethyl)benzamide | 472 | 21.8 |
| 447 | 3,4-dichloro-N-(5-{[2-(ethylsulfanyl)ethyl]amino}-1,3,4-thiadiazol-2-yl)benzamide | 377 | 21.6 |
| 448 | 2,6-dichloro-N-(5-{[2-(1H-imidazol-4-yl)ethyl]amino}-1,3,4-thiadiazol-2-yl)benzamide | 383 | 21.6 |
| 449 | N-{5-[(cyclohexylmethyl)amino]-1,3,4-thiadiazol-2-yl}-4-methylbenzamide | 331 | 21.5 |
| 450 | 2-ethoxy-N-{5-[(tetrahydro-2-furanylmethyl)amino]-1,3,4-thiadiazol-2-yl}-1-naphthamide | 399 | 21.4 |
| 451 | 3,5-difluoro-N-{5-[(4-fluorobenzyl)amino]-1,3,4-thiadiazol-2-yl}benzamide | 365 | 21.4 |
| 452 | N-{5-[(3,4-dichlorobenzyl)amino]-1,3,4-thiadiazol-2-yl}-2-methoxybenzamide | 409 | 21.3 |
| 453 | N-{5-[(2-morpholinoethyl)amino]-1,3,4-thiadiazol-2-yl}-1-benzothiophene-2-carboxamide | 390 | 21.2 |
| 454 | N-(5-{[2-(1H-imidazol-4-yl)ethyl]amino}-1,3,4-thiadiazol-2-yl)-4-iodobenzamide | 441 | 21.2 |
| 455 | N-{5-[(1-benzyl-4-piperidinyl)amino]-1,3,4-thiadiazol-2-yl}-4-bromobenzamide | 472 | 20.8 |
| 456 | N-{5-[(1-benzyl-4-piperidinyl)amino]-1,3,4-thiadiazol-2-yl}-5-nitro-2-furamide | 429 | 20.8 |
| 457 | 4-methyl-N-{5-[(1-naphthylmethyl)amino]-1,3,4-thiadiazol-2-yl}benzamide | 375 | 20.7 |
| 458 | 3,5-difluoro-N-(5-{[2-(1H-indol-3-yl)ethyl]amino}-1,3,4-thiadiazol-2-yl)benzamide | 400 | 20.7 |
| 459 | N-{5-[(1,3-benzodioxol-5-ylmethyl)amino]-1,3,4-thiadiazol-2-yl}-4-iodobenzamide | 481 | 20.7 |
| 460 | 4-[({5-[(1-benzyl-4-piperidinyl)amino]-1,3,4-thiadiazol-2-yl}amino)carbonyl]benzenesulfonyl fluoride | 476 | 20.7 |
| 461 | 3,4-dichloro-N-{5-[(2-ethylhexyl)amino]-1,3,4-thiadiazol-2-yl}benzamide | 401 | 20.6 |
| 462 | N-{5-[(3,4-dichlorobenzyl)amino]-1,3,4-thiadiazol-2-yl}-3-nitrobenzamide | 424 | 20.5 |
| 463 | N-(5-{[2-(acetylamino)ethyl]amino}-1,3,4-thiadiazol-2-yl)-2-ethoxy-1-naphthamide | 400 | 20.3 |
| 464 | 4-cyano-N-{5-[(2-morpholinoethyl)amino]-1,3,4-thiadiazol-2-yl}benzamide | 359 | 20.3 |
| 465 | (E)-N-[5-(cyclopropylamino)-1,3,4-thiadiazol-2-yl]-3-phenyl-2-propenamide | 287 | 20.2 |
| 466 | N-(5-{[2-(ethylsulfanyl)ethyl]amino}-1,3,4-thiadiazol-2-yl)-1-benzothiophene-2-carboxamide | 365 | 20.1 |
| 467 | 4-iodo-N-(5-{[2-)4-methylpiperazino)propyl]amino}-1,3,4-thiadiazol-2-yl)benzamide | 487 | 20.1 |
| 468 | 3,5-difluoro-N-[5-(1,2,3,4-tetrahydro-1-naphthalenylamino)-1,3,4-thiadiazol-2-yl]benzamide | 387 | 20.1 |
| 469 | N-{5-[(2-morpholinoethyl)amino]-1,3,4-thiadiazol-2-yl}-3-nitrobenzamide | 379 | 20.1 |
| 470 | N-{5-[(cyclopropylmethyl)amino]-1,3,4-thiadiazol-2yl}-4-iodobenzamide | 401 | 20.0 |
| 471 | N-{5-[(1,3-benzodioxol-5-ylmethyl)amino]-1,3,4-thiadiazol-2-yl}-4-cyanobenzamide | 380 | 20.0 |
| 472 | 4-({[5-(phenethylamino)-1,3,4-thiadiazol-2-yl]amino}-carbonyl)benzenesulfonyl fluoride | 407 | 20.0 |

We claim:
1. A compound of formula I

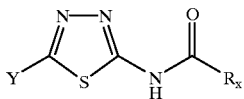

or pharmaceutically acceptable salts thereof wherein:

Y is
  a) —NHR$_1$, or
  b) 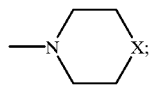

X is
  a) —O—,
  b) —S(=O)$_h$—,
  c) —CH$_2$—, or
  d) —NR$_2$—;

R$_1$ is
  a) C$_{4-12}$ alkyl,
  b) —(CH$_2$)$_i$-C$_{3-7}$ cycloalkyl,
  c) 6,6-dimethylbicyclo[3.1.1]-2-heptyl,
  d) —(CH$_2$)$_j$-M,
  e) —(CH$_2$)$_j$-W,
  f) —(CH$_2$)$_k$ aryl, wherein aryl may be substituted with one to three R$_3$,
  g) —(CH$_2$)$_k$-het, wherein het may be substituted with one to three R$_3$, or
  h) —(CH$_2$)$_k$-Q, wherein Q may be substituted with one to three R$_3$;

R$_2$ is
  a) H,
  b) C$_{1-4}$ alkyl,
  c) —C(=O)C$_{1-4}$ alkyl,
  d) —S(=O)C$_{1-4}$ alkyl,
  e) —CO$_2$C$_{1-4}$ alkyl, or
  f) —CO$_2$CH$_2$phenyl;

R$_3$ is
  a) halo,
  b) C$_{1-4}$ alkyl,
  c) C$_{1-4}$ alkoxy,
  d) benzyl,
  e) —CN,
  f) —SO$_2$F,
  g) —SO$_2$NH$_2$,
  h) —CF$_3$,
  i) —NO$_2$,
  j) —OCH$_2$O—,
  k) —CO$_2$(C$_{1-4}$ alkyl),
  l) —C(=O)C$_{1-4}$ alkyl,
  m) —C(=O)NH$_2$,
  n) —NHCO$_2$(C$_{1-4}$ alkyl), or
  o) —C(=O)—O—C(=O)—;

M is
  a) —CN,
  b) halo,
  c) —CO$_2$C$_{1-4}$ alkyl,
  d) —CH(phenyl)$_2$, e) 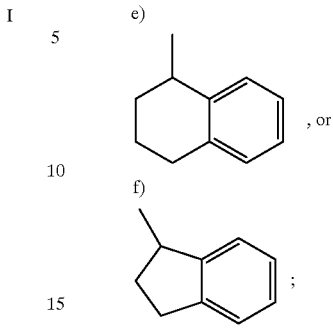 , or f) ;

W is
  a) —OR$_4$,
  b) —SR$_4$,
  c) —NHR$_5$, or
  d) —NR$_6$R$_7$;

R$_4$ is
  a) C$_{1-4}$ alkyl,
  b) C$_{3-7}$ cycloalkyl, or
  c) aryl;

R$_5$ is
  a) C$_{1-4}$ alkyl,
  b) C$_{3-7}$ cycloalkyl,
  c) aryl, or
  d) —C(=O)C$_{1-4}$ alkyl;

R$_6$ and R$_7$ are independently
  a) C$_{1-4}$ alkyl, or
  b) R$_6$ and R$_7$ together with nitrogen form azetidinyl, pyrrolidinyl, piperdinyl, piperazinyl, 4-methyl-1-piperazinyl, hydantoin, 4-morpholinyl, thiomorpholinyl, or 2-oxo-1-pyrrolidinyl;

R$_1$ is
  a) C$_{1-18}$ alkyl,
  b) C$_{2-18}$ alkenyl,
  c) C$_{2-18}$ alkynyl,
  d) C$_{2-6}$ alkyl substituted with one to three halo, C$_{1-3}$ alkoxy, —OH, —SH, or —CO$_2$H,
  e) C$_{2-6}$ alkenyl substituted with aryl, wherein the aryl may be in turn substituted with one to three R$_2$,
  f) —(CH$_2$)$_i$ aryl, wherein aryl may be substituted with one to three R$_3$,
  g) —(CH$_2$)$_i$-Q, wherein Q may be substituted with one to three R$_3$, or
  h) —(CH$_2$)$_i$-U, wherein U may be substituted with one to three R$_3$; aryl is phenyl or naphthyl;

het is
  a) furyl, thienyl, pyrrolyl, pyrazolyl, imidazolyl, oxazolyl, isoxazolyl, thiazolyl, isothiazolyl,
  b) pyridyl, pyrimidinyl, pyridazinyl, pyrazinyl, pyranyl,
  c) indazolyl, benzothiazolyl, benzoimidazolyl, benzofuryl, isobenzofuryl, benzothiazole, benzoisoxazole, benzothienyl, indolyl, isoindolyl, or
  d) quinolyl, isoquinolyl, quinazolinyl, quinoxalinyl, phthalazinyl or cinnolinyl;

U is
  a) furyl, thienyl, pyrrolyl, pyrazolyl, imidazolyl, oxazolyl, isoxazolyl, thiazolyl, isothiazolyl,
  b) pyridyl, pyrimidinyl, pyridazinyl, pyrazinyl, pyranyl, or c) indazolyl, benzothiazolyl, benzoimidazolyl, benzofuryl, isobenzofuryl, benzothiazole, benzoisoxazole, benzothienyl, indolyl, isoindolyl;

Q is
 a) 2-, 3-, or 4-piperidinyl,
 b) 1-, or 2-pyrrolidinyl,
  wherein the nitrogen atom in a) and b) may be substituted with $C_{1-4}$ alkyl, phenyl, benzyl, or —C(=O)$C_{1-4}$ alkyl,
 c) morpholinyl,
 d) thiomorpholinyl,
 e) dioxolanyl,
 f) imidazolidinyl,
 g) oxathiolanyl,
 h) oxazolidinyl,
 i) tetrahydrofuryl, or
 j) 2-oxo-1-pyrrolidinyl.

h is 0, 1, or 2;
i is 0, 1, 2, 3, or 4;
j is 2, 3, or 4;
k is 0, 1, 2, 3, 4, 5, or 6;
and with the following provisos:
 a) where $R_3$ is phenyl or 4-methoxyphenyl, $R_1$ is other than phenyl, 4-methoxyphenyl, or 4-chlorophenyl;
 b) where $R_3$ is —CH$_2$phenyl, $R_1$ is other than phenyl or —CH$_2$phenyl;
 c) where $R_3$ is H, substituted or unsubstituted alkyl or phenyl, $R_1$ is other than unsubstituted alkyl or phenyl.

2. A compound of claim 1 wherein X is
 a) —O—, or
 b) —NR$_2$—;
$R_2$ is
 a) H,
 b) —CO$_2$C$_{1-4}$ alkyl, or
 c) —CO$_2$CH$_2$ phenyl.

3. A compound of claim 1 wherein het is furyl, thienyl, pyrrolyl, imidazolyl, pyrazolyl, isoxazolyl, pyridyl, benzothienyl, or indolyl.

4. A compound of claim 1 wherein Q is 1-methyl-2-pyrrolidinyl, 1-methyl-4-piperidinyl, 1-ethylcarboxylate-4-piperidinyl, 1-benzyl-4-piperidinyl, or tetrahydrofuryl.

5. A compound of claim 1 wherein $R_3$ is
 a) chloro,
 b) fluoro,
 c) methyl,
 d) methoxy,
 e) ethoxy,
 f) —CN,
 g) —SO$_2$NH$_2$,
 h) —NO$_2$,
 i) —OCH$_2$O—, or
 j) —C(=O)—O—C(=O)—.

6. A compound of claim 1 wherein Rx is
 a) $C_{2-18}$ alkenyl,
 b) $C_{2-6}$ alkyl substituted with halo, or —CO$_2$H,
 c) $C_{2-6}$ alkenyl substituted with aryl, wherein the aryl may be in turn substituted with one to three halo,
 d) —(CH$_2$)$_i$ aryl, wherein aryl may be substituted with one to three $R_3$, or
 e) —(CH$_2$)$_i$-U, wherein het may be substituted with one to three $R_3$;

Y is —NHR$_1$; aryl, U, $R_1$ and i are the same as defined in claim 1; and $R_3$ is chloro, fluoro, methyl, methoxy, ethoxy, —CN, —SO$_2$NH$_2$, —NO$_2$, —OCH$_2$O—, or —C(=O)—O—C(=O)—.

7. A compound of claim 1 which is
1) 2-methoxy-N-[5-(phenethylamino)-1,3,4-thiadiazol-2-yl]benzamide,
2) 4-methyl-N-[5-(phenethylamino)-1,3,4-thiadiazol-2-yl]benzamide,
3) 5-chloro-N-[5-(phenethylamino)-1,3,4-thiadiazol-2-yl]pentanamide,
4) 4-cyano-N-[5-(phenethylamino)-1,3,4-thiadiazol-2-yl]benzamide,
5) 3-nitro-N-[5-(phenethylamino)-1,3,4-thiadiazol-2-yl]benzamide,
6) 3,5-difluoro-N-[5-(phenethylamino)-1,3,4-thiadiazol-2-yl]benzamide,
7) (E)-3-(2-chlorophenyl)-N-[5-(phenethylamino)-1,3,4-thiadiazol-2-yl]-2-propenamide,
8) 2-ethoxy-N-[5-(phenethylamino)-1,3,4-thiadiazol-2-yl]-1-naphthamide,
9) (E)-N-[5-(phenethylamino)-1,3,4-thiadiazol-2-yl]-9-octadecenamide,
10) 2,6-dichloro-N-[5-(phenethylamino)-1,3,4-thiadiazol-2-yl]benzamide,
11) 3,4-dichloro-N-[5-(phenethylamino)-1,3,4-thiadiazol-2-yl]benzamide,
12) (E)-N-[5-(phenethylamino)-1,3,4-thiadiazol-2-yl]-3-phenyl-2-propenamide,
13) 4-iodo-N-[5-(phenethylamino)-1,3,4-thiadiazol-2-yl]benzamide,
14) 1,3-dioxo-N-[5-(phenethylamino)-1,3,4-thiadiazol-2-yl]-1,3-dihydro-2-benzofuran-5-carboxamide,
15) 4-({[5-(phenethylamino)-1,3,4-thiadiazol-2-yl]amino}carbonyl)benzenesulfonyl fluoride,
16) 5-nitro-N-[5-(phenethylamino)-1,3,4-thiadiazol-2-yl]-2-furamide,
17) (E)-3-(2-chlorophenyl)-N-{5-[(2-furylmethyl)amino]-1,3,4-thiadiazol-2-yl}-2-propenamide,
18) 2-ethoxy-N-{5-[(2-furylmethyl)amino]-1,3,4-thiadiazol-2-yl}-1-naphthamide,
19) (E)-N-{5-[(2-furylmethyl)amino]-1,3,4-thiadiazol-2-yl}-9-octadecenamide,
20) 2,6-dichloro-N-{5-[(2-furylmethyl)amino]-1,3,4-thiadiazol-2-yl}benzamide,
21) 3,4-dichloro-N-{5-[(2-furylmethyl)amino]-1,3,4-thiadiazol-2-yl}benzamide,
22) N-{5-[(2-furylmethyl)amino]-1,3,4-thiadiazol-2-yl}-4-iodobenzamide,
23) N-{5-[(2-furylmethyl)amino]-1,3,4-thiadiazol-2-yl}-2,4,6-triisopropylbenzamide,
24) N-{5-[(2-furylmethyl)amino]-1,3,4-thiadiazol-2-yl}-1-benzothiophene-2-carboxamide,
25) 2,4-difluoro-N-(5-{[3-(2-oxo-1-pyrrolidinyl)propyl]amino}-1,3,4-thiadiazol-2-yl)benzamide,
26) 4-bromo-N-(5-{[3-(2-oxo-1-pyrrolidinyl)propyl]amino}-1,3,4-thiadiazol-2-yl)benzamide,
27) 4-methyl-N-(5-{[3-(2-oxo-1-pyrrolidinyl)propyl]amino}-1,3,4-thiadiazol-2-yl)benzamide,
28) 5-chloro-N-(5-[3-(2-oxo-1-pyrrolidinyl)propyl]amino}-1,3,4-thiadiazol-2-yl)pentanamide,
29) 4-cyano-N-(5-{[3-(2-oxo-1-pyrrolidinyl)propyl]amino}-1,3,4-thiadiazol-2-yl)benzamide, 30) 3-nitro-N-(5-{[3-(2-oxo-1-pyrrolidinyl)propyl]amino}-1,3,4-thiadiazol-2-yl)benzamide,
31) 3,5-difluoro-N-(5-{[3-(2-oxo-1-pyrrolidinyl)propyl]amino}-1,3,4-thiadiazol-2-yl)benzamide,
32) (E)-3-(2-chlorophenyl)-N-(5-{[3-(2-oxo-1-pyrrolidinyl)propyl]amino}-1,3,4-thiadiazol-2-yl)-2-propenamide,
33) 3,4-dichloro-N-(5-{[3-(2-oxo-1-pyrrolidinyl)propyl]amino}-1,3,4-thiadiazol-2-yl)benzamide,
34) (E)-N-(5-{[3-(2-oxo-1-pyrrolidinyl)propyl]amino}-1,3,4-thiadiazol-2-yl)-3-phenyl-2-propenamide,
35) 4-iodo-N-(5-{[3-(2-oxo-1-pyrrolidinyl)propyl]amino}-1,3,4-thiadiazol-2-yl)benzamide,
36) 1,3-dioxo-N-(5-{[3-(2-oxo-1-pyrrolidinyl)propyl]amino}-1,3,4-thiadiazol-2-yl)-1,3-dihydro-2-benzofuran-5-carboxamide,
37) 4-{[(5-{[3-(2-oxo-1-pyrrolidinyl)propyl]amino}-1,3,4-thiadiazol-2-yl)amino]carbonyl}benzenesulfonyl fluoride,
38) 2,4,6-triisopropyl-N-(5-{[3-(2-oxo-1-pyrrolidinyl)propyl]amino}-1,3,4-thiadiazol-2-yl)benzamide,
39) 5-nitro-N-(5-{[3-(2-oxo-1-pyrrolidinyl)propyl]amino}-1,3,4-thiadiazol-2-yl)-2-furamide,
40) N-(5-[3-(2-oxo-1-pyrrolidinyl)propyl]amino}-1,3,4-thiadiazol-2-yl)-1-benzothiophene-2-carboxamide,
41) (E)-3-(2-chlorophenyl)-N-{5-[(2-pyridinylmethyl)amino]-1,3,4-thiadiazol-2-yl}-2-propenamide,
42) 2-ethoxy-N-{5-[(2-pyridinylmethyl)amino]-1,3,4-thiadiazol-2-yl-1-naphthamide,
43) (E)-N-{5-[(2-pyridinylmethyl)amino]-1,3,4-thiadiazol-2-yl}-9-octadecenamide,
44) 2,6-dichloro-N-{5-[(2-pyridinylmethyl)amino]-1,3,4-thiadiazol-2-yl}benzamide,
45) (E)-3-phenyl-N-{5-[(2-pyridinylmethyl)amino]-1,3,4-thiadiazol-2-yl}-2-propenamide,
46) N-{5-[(2-anilinoethyl)amino]-1,3,4-thiadiazol-2-yl}-2-methoxybenzamide,
47) N-{5-[(2-anilinoethyl)amino]-1,3,4-thiadiazol-2-yl}-4-bromobenzamide,
48) N-{5-[(2-anilinoethyl)amino]-1,3,4-thiadiazol-2-yl}-4-methylbenzamide,
49) N-{5-[(2-anilinoethyl)amino]-1,3,4-thiadiazol-2-yl}-3-nitrobenzamide,
50) (E)-N-{5-[(2-anilinoethyl)amino]-1,3,4-thiadiazol-2-yl}-3-(2-chlorophenyl)-2-propenamide,
51) N-{5-[(2-anilinoethyl)amino]-1,3,4-thiadiazol-2-yl}-2-ethoxy-1-naphthamide,
52) (E)-N-{5-[(2-anilinoethyl)amino]-1,3,4-thiadiazol-2-yl}-9-octadecenamide,
53) N-{5-[(2-anilinoethyl)amino]-1,3,4-thiadiazol-2-yl}-2,6-dichlorobenzamide,
54) N-{5-[(2-anilinoethyl)amino]-1,3,4-thiadiazol-2-yl}-3,4-dichlorobenzamide,
55) (E)-N-{5-[(2-anilinoethyl)amino]-1,3,4-thiadiazol-2-yl}-3-phenyl-2-propenamide,
56) N-{5-[(2-anilinoethyl)amino]-1,3,4-thiadiazol-2-yl}-4-iodobenzamide,
57) N-{5-[(2-anilinoethyl)amino]-1,3,4-thiadiazol-2-yl}-1,3-dioxo-1,3-dihydro-2-benzofuran-5-carboxamide,
58) 4-[({5-[(2-anilinoethyl)amino]-1,3,4-thiadiazol-2-yl}amino)carbonyl]benzenesulfonyl fluoride,
59) N-{5-[(2-anilinoethyl)amino]-1,3,4-thiadiazol-2-yl}-2,4,6-triisopropylbenzamide
60) N-{5-[(2-anilinoethyl)amino]-1,3,4-thiadiazol-2-yl}-5-nitro-2-furamide,
61) N-{5-[(2-anilinoethyl)amino]-1,3,4-thiadiazol-2-yl}-1-benzothiophene-2-carboxamide,
62) N-(5-{[2-(1H-indol-3-yl)ethyl]amino}-1,3,4-thiadiazol-2-yl)-2-methoxybenzamide,
63) 4-bromo-N-(5-{[2-(1H-indol-3-yl)ethyl]amino}-1,3,4-thiadiazol-2-yl)benzamide,
64) 5-chloro-N-(5-{[2-(1H-indol-3-yl)ethyl]amino}-1,3,4-thiadiazol-2-yl)pentanamide,
65) 4-cyano-N-(5-{[2-(1H-indol-3-yl)ethyl]amino}-1,3,4-thiadiazol-2-yl)benzamide,
66) N-(5-{[2-(1H-indol-3-yl)ethyl]amino}-1,3,4-thiadiazol-2-yl)-3-nitrobenzamide,
67) 3,5-difluoro-N-(5-{[2-(1H-indol-3-yl)ethyl]amino}-1,3,4-thiadiazol-2-yl)benzamide,
68) (E)-3-(2-chlorophenyl)-N-(5-{[2-(1H-indol-3-yl)ethyl]amino}-1,3,4-thiadiazol-2-yl)-2-propenamide,
69) 2-ethoxy-N-(5-{[2-(1H-indol-3-yl)ethyl]amino}-1,3,4-thiadiazol-2-yl)-1-naphthamide,
70) (E)-N-(5-[2-(1H-indol-3-yl)ethyl]amino}-1,3,4-thiadiazol-2-yl)-9-octadecenamide,
71) 2,6-dichloro-N-(5-{[2-(1H-indol-3-yl)ethyl]amino}-1,3,4-thiadiazol-2-yl)benzamide,
72) 3,4-dichloro-N-(5-{[2-(1H-indol-3-yl)ethyl]amino}-1,3,4-thiadiazol-2-yl)benzamide,
73) N-(5-{[2-(1H-indol-3-yl)ethyl]amino}-1,3,4-thiadiazol-2-yl)-4(trifluoromethyl)benzamide,
74) (E)-N-(5-{[2-(1H-indol-3-yl)ethyl]amino}-1,3,4-thiadiazol-2-yl)-3-phenyl-2-propenamide,
75) N-(5-{[2-(1H-indol-3-yl)ethyl]amino}-1,3,4-thiadiazol-2-yl)-4-iodobenzamide,
76) N-(5-{[2-(1H-indol-3-yl)ethyl]amino}-1,3,4-thiadiazol-2-yl)-1,3-dioxo-1,3-dihydro-2-benzofuran-5-carboxamide,
77) 4-[(5-{[2-(1H-indol-3-yl)ethyl]amino}-1,3,4-thiadiazol-2-yl)amino]carbonyl}benzenesulfonyl fluoride,
78) N-(5-{[2-(1H-indol-3-yl)ethyl]amino}-1,3,4-thiadiazol-2-yl)-2,4,6-triisopropylbenzamide,
79) N-(5-{[2-(1H-indol-3-yl)ethyl]amino}-1,3,4-thiadiazol-2-yl)-5-nitro-2-furamide,
80) N-(5-{[2-(1H-indol-3-yl)ethyl]amino}-1,3,4-thiadiazol-2-yl)-1-benzothiophene-2-carboxamide,
81) N-[5-(cycloheptylamino)-1,3,4-thiadiazol-2-yl]-2-methoxybenzamide,
82) N-[5-(cycloheptylamino)-1,3,4-thiadiazol-2-yl]-4-methylbenzamide,
83) 5-chloro-N-[5-(cycloheptylamino)-1,3,4-thiadiazol-2-yl]pentanamide,
84) 4-cyano-N-[5-(cycloheptylamino)-1,3,4-thiadiazol-2-yl]benzamide,
85) N-[5-(cycloheptylamino)-1,3,4-thiadiazol-2-yl]-3-nitrobenzamide,
86) N-[5-(cycloheptylamino)-1,3,4-thiadiazol-2-yl]-3,5-difluorobenzamide,
87) (E)-3-(2-chlorophenyl)-N-[5-(cycloheptylamino)-1,3,4-thiadiazol-2-yl]-2-propenamide,
88) N-[5-(cycloheptylamino)-1,3,4-thiadiazol-2-yl]-2-ethoxy-1-naphthamide,
89) (E)-N-[5-(cycloheptylamino)-1,3,4-thiadiazol-2-yl]-9-octadecenamide, 90) 2,6-dichloro-N-[5-(cycloheptylamino)-1,3,4-thiadiazol-2-yl]benzamide,
91) 3,4-dichloro-N-[5-(cycloheptylamino)-1,3,4-thiadiazol-2-yl]benzamide,
92) (E)-N-[5-(cycloheptylamino)-1,3,4-thiadiazol-2-yl]-3-phenyl-2-propenamide,
93) N-[5-(cycloheptylamino)-1,3,4-thiadiazol-2-yl]-4-iodobenzamide,
94) N-[5-(cycloheptylamino)-1,3,4-thiadiazol-2-yl]-1,3-dioxo-1,3-dihydro-2-benzofuran-5-carboxamide,
95) 4-({[5-(cycloheptylamino)-1,3,4-thiadiazol-2-yl]amino}carbonyl)benzenesulfonyl fluoride,
96) N-[5-(cycloheptylamino)-1,3,4-thiadiazol-2-yl]-2,4,6-triisopropylbenzamide, N-[5-(cycloheptylamino)-1,3,4-thiadiazol-2-yl]-5-nitro-2-furamide,
97) N-[5-(cycloheptylamino)-1,3,4-thiadiazol-2-yl]-1-benzothiophene-2-carboxamide,
98) N-{5-[(cyclohexylmethyl)amino]-1,3,4-thiadiazol-2-yl}-2,4-difluorobenzamide,
99) N-{5-[(cyclohexylmethyl)amino]-1,3,4-thiadiazol-2-yl}-2-methoxybenzamide,
100) N-{5-[(cyclohexylmethyl)amino]-1,3,4-thiadiazol-2-yl}-4-methylbenzamide,
101) 5-chloro-N-{5-[(cyclohexylmethyl)amino]-1,3,4-thiadiazol-2-yl}pentanamide,
102) 4-cyano-N-{5-[(cyclohexylmethyl)amino]-1,3,4-thiadiazol-2-yl}benzamide,
103) (E)-3-(2-chlorophenyl)-N-{5-[(cyclohexylmethyl)amino]-1,3,4-thiadiazol-2-yl}-2-propenamide,
104) N-{5-[(cyclohexylmethyl)amino]-1,3,4-thiadiazol-2-yl}-2-ethoxy-1-naphthamide,
105) (E)-N-{5-[(cyclohexylmethyl)amino]-1,3,4-thiadiazol-2-yl}-9-octadecenamide,
106) 3,4-dichloro-N-{5-[(cyclohexylmethyl)amino]-1,3,4-thiadiazol-2-yl}benzamide,
107) (E)-N-{5-[(cyclohexylmethyl)amino]-1,3,4-thiadiazol-2-yl}-3-phenyl-2-propenamide,
108) N-{5-[(cyclohexylmethyl)amino]-1,3,4-thiadiazol-2-yl}-1,3-dioxo-1,3-dihydro-2-benzofuran-5-carboxamide,
109) N-{5-[(cyclohexylmethyl)amino]-1,3,4-thiadiazol-2-yl}-2,4,6-triisopropyl benzamide,
110) N-{5-[(cyclohexylmethyl)amino]-1,3,4-thiadiazol-2-yl}-5-nitro-2-furamide,
111) N-[5-({[(2R)-6,6-dimethylbicyclo[3.1.1]hept-2-yl]methyl}amino)-1,3,4-thiadiazol-2-yl]-2-methoxybenzamide,
112) 5-chloro-N-[5-({[(2R)-6,6-dimethylbicyclo[3.1.1]hept-2-yl]methyl}amino)-1,3,4-thiadiazol-2-yl]pentanamide,
113) 4-cyano-N-[5-({[(2R)-6,6-dimethylbicyclo[3.1.1]hept-2-yl]methyl}amino)-1,3,4-thiadiazol-2-yl]benzamide,
114) N-[5-({[(2R)-6,6-dimethylbicyclo[3.1.1]hept-2-yl]methyl}amino)-1,3,4-thiadiazol-2-yl]-3,5-difluorobenzamide,
115) (E)-3-(2-chlorophenyl)-N-[5-({[(2R)-6,6-dimethylbicyclo[3.1.1]hept-2-yl]methyl}amino)-1,3,4-thiadiazol-2-yl]-2-propenamide,
116) N-[5-({[(2R)-6,6-dimethylbicyclo[3.1.1]hept-2-yl]methyl}amino)-1,3,4-thiadiazol-2-yl]-2-ethoxy-1-naphthamide,
117) (E)-N-[5-({[(2R)-6,6-dimethylbicyclo[3.1.1]hept-2-yl]methyl}amino)-1,3,4-thiadiazol-2-yl]-9-octadecenamide,
118) N-[5-({[(2R)-6,6-dimethylbicyclo[3.1.1]hept-2-yl]methyl}amino)-1,3,4-thiadiazol-2-yl]-1,3-dioxo-1,3-dihydro-2-benzofuran-5-carboxamide,
119) N-[5-({[(2R)-6,6-dimethylbicyclo[3.1.1]hept-2-yl]methyl}amino)-1,3,4-thiadiazol-2-yl]-2,4,6-triisopropylbenzamide,
120) N-[5-({[(2R)-6,6-dimethylbicyclo[3.1.1]hept-2-yl]methyl}amino)-1,3,4-thiadiazol-2-yl]-5-nitro-2-furamide,
121) N-[5-({[(2R)-6,6-dimethylbicyclo[3.1.1]hept-2-yl]methyl}amino)-1,3,4-thiadiazol-2-yl]-1-benzothiophene-2-carboxamide,
122) (E)-3-(2-chlorophenyl)-N-(5-{[2-(1-pyrrolidinyl)ethyl]amino}-1,3,4-thiadiazol-2-yl)-2-propenamide,
123) (E)-N-(5-{[2-(1-pyrrolidinyl)ethyl]amino}-1,3,4-thiadiazol-2-yl)-9-octadecenamide,
124) 2-6-dichloro-N-(5-{[2-(1-pyrrolidinyl)ethyl]amino}-1,3,4-thiadiazol-2-yl)benzamide,
125) (E)-3-phenyl-N-(5-{[2-(1-pyrrolidinyl)ethyl]amino}-1,3,4-thiadiazol-2-yl)-2-propenamide,
126) 2,4,6-triisopropyl-N-(5-{[2-(1-pyrrolidinyl)ethyl]amino}-1,3,4-thiadiazol-2-yl)benzamide,
127) 2-ethoxy-N-{5-[(tetrahydro-2-furanylmethyl)amino]-1,3,4-thiadiazol-2-yl}-1-naphthamide,
128) (E)-N-{5-[(tetrahydro-2-furanylmethyl)amino]-1,3,4-thiadiazol-2-yl}-9-octadecenamide,
129) N-{5-[(tetrahydro-2-furanylmethyl)amino]-1,3,4-thiadiazol-2-yl}-1-benzothiophene-2-carboxamide,
130) (E)-3-(2-chlorophenyl)-N-{5-[(4-pyridinylmethyl)amino]-1,3,4-thiadiazol-2-yl}-2-propenamide,
131) 2,6-dichloro-N-{5-[(4-pyridinylmethyl)amino]-1,3,4-thiadiazol-2-yl}benzamide,
132) 3,4-dichloro-N-{5-[(4-pyridinylmethyl)amino]-1,3,4-thiadiazol-2-yl}benzamide,
133) (E)-3-phenyl-N-{5-[(4-pyridinylmethyl)amino]-1,3,4-thiadiazol-2-yl}-2-propenamide,
134) 4-iodo-N-{5-[(4-pyridinylmethyl)amino]-1,3,4-thiadiazol-2-yl}benzamide,
135) 1,3-dioxo-N-{5-[(4-pyridinylmethyl)amino]-1,3,4-thiadiazol-2-yl}-1,3-dihydro-2-benzofuran-5-carboxamide,
136) 2,4,6-triisopropyl-N-{5-[(4-pyridinylmethyl)amino]-1,3,4-thiadiazol-2-yl}benzamide,
137) N-{5-[(4-pyridinylmethyl)amino]-1,3,4-thiadiazol-2-yl}-1-benzothiophene-2-carboxamide,
138) N-{5-[(1,3-benzodioxol-5-ylmethyl)amino]-1,3,4-thiadiazol-2-yl}-2,4-difluorobenzamide,
139) N-{5-[(1,3-benzodioxol-5-ylmethyl)amino]-1,3,4-thiadiazol-2-yl}-2-methoxybenzamide,
140) N-{5-[(1,3-benzodioxol-5-ylmethyl)amino]-1,3,4-thiadiazol-2-yl}-4-bromobenzamide,
141) N-{5-[(1,3-benzodioxol-5-ylmethyl)amino]-1,3,4-thiadiazol-2-yl}-4-methylbenzamide,
142) N-{5-[(1,3-benzodioxol-5-ylmethyl)amino]-1,3,4-thiadiazol-2-yl}-5-chloropentanamide,
143) N-{5-[(1,3-benzodioxol-5-ylmethyl)amino]-1,3,4-thiadiazol-2-yl}-4-cyanobenzamide,
144) N-{5-[(1,3-benzodioxol-5-ylmethyl)amino]-1,3,4-thiadiazol-2-yl}-3,5-difluorobenzamide, 145) (E)-N-{5-[(1,3-benzodioxol-5-ylmethyl)amino]-1,3,4-thiadiazol-2-yl}-3-(2-chlorophenyl)-2-propenamide,
146) N-{5-[(1,3-benzodioxol-5-ylmethyl)amino]-1,3,4-thiadiazol-2-yl}-2-ethoxy-1-naphthamide,
147) (E)-N-{5-[(1,3-benzodioxol-5-ylmethyl)amino]-1,3,4-thiadiazol-2-yl}-9-octadecenamide,
148) N-{5-[(1,3-benzodioxol-5-ylmethyl)amino]-1,3,4-thiadiazol-2-yl}-2,6-dichlorobenzamide,
149) (E)-N-{5-[(1,3-benzodioxol-5-ylmethyl)amino]-1,3,4-thiadiazol-2-yl}-3-phenyl-2-propenamide,
150) N-{5-[(1,3-benzodioxol-5-ylmethyl)amino]-1,3,4-thiadiazol-2-yl}-4-iodobenzamide,
151) N-{5-[(1,3-benzodioxol-5-ylmethyl)amino]-1,3,4-thiadiazol-2-yl}-1,3-dioxo-1,3-dihydro-2-benzofuran-5-carboxamide,
152) N-{5-[(1,3-benzodioxol-5-ylmethyl)amino]-1,3,4-thiadiazol-2-yl}-2,4,6-triisopropylbenzamide,
153) N-{5-[(1,3-benzodioxol-5-ylmethyl)amino]-1,3,4-thiadiazol-2-yl}-1-benzothiophene-2-carboxamide,
154) 4-cyano-N-{5-[(2-morpholinoethyl)amino]-1,3,4-thiadiazol-2-yl}benzamide,
155) N-{5-[(2-morpholinoethyl)amino]-1,3,4-thiadiazol-2-yl}-3-nitrobenzamide,
156) (E)-N-{5-[(2-morpholinoethyl)amino]-1,3,4-thiadiazol-2-yl}-3-phenyl-2-propenamide,
157) N-{5-[(2-morpholinoethyl)amino]-1,3,4-thiadiazol-2-yl}-1-benzothiophene-2-carboxamide,
158) 2,4-difluoro-N-{5-[(1-naphthylmethyl)amino]-1,3,4-thiadiazol-2-yl}benzamide,
159) 2-methoxy-N-{5-[(1-naphthylmethyl)amino]-1,3,4-thiadiazol-2-yl}benzamide,
160) 4-methyl-N-{5-[(1-naphthylmethyl)amino]-1,3,4-thiadiazol-2-yl}benzamide,
161) 5-chloro-N-{5-[(1-naphthylmethyl)amino]-1,3,4-thiadiazol-2-yl}pentanamide,
162) 4-cyano-N-{5-[(1-naphthylmethyl)amino]-1,3,4-thiadiazol-2-yl}benzamide,
163) N-{5-[(1-naphthylmethyl)amino]-1,3,4-thiadiazol-2-yl}-3-nitrobenzamide,
164) 3,5-difluoro-N-{5-[(1-naphthylmethyl)amino]-1,3,4-thiadiazol-2-yl}benzamide,
165) (E)-3-(2-chlorophenyl)-N-{5-[(1-naphthylmethyl)amino]-1,3,4-thiadiazol-2-yl}-2-propenamide,
166) 2-ethoxy-N-{5-[(1-naphthylmethyl)amino]-1,3,4-thiadiazol-2-yl}-1-naphthamide,
167) (E)-N-{5-[(1-naphthylmethyl)amino]-1,3,4-thiadiazol-2-yl}-9-octadecenamide,
168) 2,6-dichloro-N-{5-[(1-naphthylmethyl)amino]-1,3,4-thiadiazol-2-yl}benzamide,
169) (E)-N-{5-[(1-naphthylmethyl)amino]-1,3,4-thiadiazol-2-yl}-3-phenyl-2-propenamide,
170) 4-iodo-N-{5-[(1-naphthylmethyl)amino]-1,3,4-thiadiazol-2-yl}benzamide,
171) N-{5-[(1-naphthylmethyl)amino]-1,3,4-thiadiazol-2-yl}-1,3-dioxo-1,3-dihydro-2-benzofuran-5-carboxamide,
172) 4-[({5-[(1-naphthylmethyl)amino]-1,3,4-thiadiazol-2-yl}amino)carbonyl]benzenesulfonyl fluoride,
173) 2,4,6-triisopropyl-N-{5-[(1-naphthylmethyl)amino]-1,3,4-thiadiazol-2-yl}benzamide,
174) N-{5-[(1-naphthylmethyl)amino]-1,3,4-thiadiazol-2-yl}-5-nitro-2-furamide,
175) N-{5-[(1-naphthylmethyl)amino]-1,3,4-thiadiazol-2-yl}-1-benzothiophene-2-carboxamide,
176) 2,4-difluoro-N-{5-[(4-fluorobenzyl)amino]-1,3,4-thiadiazol-2-yl}benzamide,
177) N-{5-[(4-fluorobenzyl)amino]-1,3,4-thiadiazol-2-yl}-2-methoxybenzamide,
178) 5-chloro-N-{5-[(4-fluorobenzyl)amino]-1,3,4-thiadiazol-2-yl}pentanamide,
179) 4-cyano-N-{5-[(4-fluorobenzyl)amino]-1,3,4-thiadiazol-2-yl}benzamide,
180) N-{5-[(4-fluorobenzyl)amino]-1,3,4-thiadiazol-2-yl}-3-nitrobenzamide,
181) 3,5-difluoro-N-{5-[(4-fluorobenzyl)amino]-1,3,4-thiadiazol-2-yl}benzamide,
182) (E)-3-(2-chlorophenyl)-N-{5-[(4-fluorobenzyl)amino]-1,3,4-thiadiazol-2-yl}-2-propenamide,
183) 2-ethoxy-N-{5-[(4-fluorobenzyl)amino]-1,3,4-thiadiazol-2-yl}-1-naphthamide,
184) (E)-N-{5-[(4-fluorobenzyl)amino]-1,3,4-thiadiazol-2-yl}-9-octadecenamide,
185) 2,6-dichloro-N-{5-[(4-fluorobenzyl)amino]-1,3,4-thiadiazol-2-yl}benzamide,
186) (E)-N-{5-[(4-fluorobenzyl)amino]-1,3,4-thiadiazol-2-yl}-3-phenyl-2-propenamide,
187) N-{5-[(4-fluorobenzyl)amino]-1,3,4-thiadiazol-2-yl}-1,3-dioxo-1,3-dihydro-2-benzofuran-5-carboxamide,
188) N-{5-[(4-fluorobenzyl)amino]-1,3,4-thiadiazol-2-yl}-2,4,6-triisopropylbenzamide,
189) N-{5-[(4-fluorobenzyl)amino]-1,3,4-thiadiazol-2-yl}-1-benzothiophene-2-carboxamide
190) 2-ethoxy-N-{5-[(3-pyridinylmethyl)amino]-1,3,4-thiadiazol-2-yl}-1-naphthamide,
191) (E)-N-{5-[(3-pyridinylmethyl)amino]-1,3,4-thiadiazol-2-yl}-9-octadecenamide,
192) 2,6-dichloro-N-{5-[(3-pyridinylmethyl)amino]-1,3,4-thiadiazol-2-yl}benzamide,
193) 3,4-dichloro-N-{5-[(3-pyridinylmethyl)amino]-1,3,4-thiadiazol-2-yl}benzamide,
194) (E)-3-phenyl-N-{5-[(3-pyridinylmethyl)amino]-1,3,4-thiadiazol-2-yl}-2-propenamide,
195) 2,4,6-triisopropyl-N-{5-[(3-pyridinylmethyl)amino]-1,3,4-thiadiazol-2-yl}benzamide,
196) N-{5-[(3-pyridinylmethyl)amino]-1,3,4-thiadiazol-2-yl}-1-benzothiophene-2-carboxamide,
197) 2,4,6-triisopropyl-N-{5-[(2-piperidinoethyl)amino]-1,3,4-thiadiazol-2-yl}benzamide,
198) (E)-N-{5-[(2-ethylhexyl)amino]-1,3,4-thiadiazol-2-yl}-9-octadecenamide,
199) 2,6-dichloro-N-{5-[(2-ethylhexyl)amino]-1,3,4-thiadiazol-2-yl}benzamide,
200) 3,4-dichloro-N-{5-[(2-ethylhexyl)amino]-1,3,4-thiadiazol-2-yl}benzamide,
201) N-{5-[(2-ethylhexyl)amino]-1,3,4-thiadiazol-2-yl}-1,3-dioxo-1,3-dihydro-2-benzofuran-5-carboxamide,
202) N-(5-{[4-(aminosulfonyl)phenethyl]amino}-1,3,4-thiadiazol-2-yl)-2-methoxybenzamide,
203) N-(5-{[4-(aminosulfonyl)phenethyl]amino}-1,3,4-thiadiazol-2-yl)-4-bromobenzamide,
204) N-(5-{[4-(aminosulfonyl)phenethyl]amino}-1,3,4-thiadiazol-2-yl)-4-methylbenzamide,
205) N-(5-{[4-(aminosulfonyl)phenethyl]amino}-1,3,4-thiadiazol-2-yl)-5-chloropentanamide, 206) N-(5-{[4-(aminosulfonyl)phenethyl]amino}-1,3,4-thiadiazol-2-yl)-4-cyanobenzamide,
207) (E)-N-(5-{[4-(aminosulfonyl)phenethyl]amino}-1,3,4-thiadiazol-2-yl)-3-(2-chlorophenyl)-2-propenamide,
208) N-(5-{[4-(aminosulfonyl)phenethyl]amino}1,3,4-thiadiazol-2-yl)-2-ethoxy-1-naphthamide,
209) (E)-N-(5-{[4-(aminosulfonyl)phenethyl]amino}-1,3,4-thiadiazol-2-yl)-9-octadecenamide,
210) N-(5-{[4-(aminosulfonyl)phenethyl]amino}-1,3,4-thiadiazol-2-yl)-2,6-dichlorobenzamide,
211) N-(5-{[4-(aminosulfonyl)phenethyl]amino}-1,3,4-thiadiazol-2-yl)-3,4-dichlorobenzamide,
212) N-(5-{[4-(aminosulfonyl)phenethyl]amino}-1,3,4-thiadiazol-2-yl)-4-(trifluoromethyl)benzamide,
213) (E)-N-(5-{[4-(aminosulfonyl)phenethyl]amino}-1,3,4-thiadiazol-2-yl)-3-phenyl-2-propenamide,
214) N-(5-{[4-(aminosulfonyl)phenethyl]amino}-1,3,4-thiadiazol-2-yl)-4-iodobenzamide,
215) N-(5-{[4-(aminosulfonyl)phenethyl]amino}-1,3,4-thiadiazol-2-yl)-1,3-dioxo-1,3-dihydro-2-benzofuran-5-carboxamide,
216) N-(5-{[4-(aminosulfonyl)phenethyl]amino}-1,3,4-thiadiazol-2-yl)-2,4,6-triisopropylbenzamide,
217) N-(5-{[4-(aminosulfonyl)phenethyl]amino}-1,3,4-thiadiazol-2-yl)-1-benzothiophene-2-carboxamide,
218) N-(5-{[3-(cyclohexylamino)propyl]amino}-1,3,4-thiadiazol-2-yl)-2,4-difluorobenzamide,
219) N-(5-{[3-(cyclohexylamino)propyl]amino}-1,3,4-thiadiazol-2-yl)-2-methoxybenzamide,
220) 4-bromo-N-(5-{[3-(cyclohexylamino)propyl]amino}-1,3,4-thiadiazol-2-yl)benzamide,
221) N-(5-{[3-(cyclohexylamino)propyl]amino}-1,3,4-thiadiazol-2-yl)-4-methylbenzamide,
222) 4-cyano-N-(5-{[3-(cyclohexylamino)propyl]amino}-1,3,4-thiadiazol-2-yl)benzamide,
223) N-(5-{[3-(cyclohexylamino)propyl]amino}-1,3,4-thiadiazol-2-yl)-3-nitrobenzamide,
224) N-(5-{[3-(cyclohexylamino)propyl]amino}-1,3,4-thiadiazol-2-yl)-3,5-difluorobenzamide,
225) (E)-3-(2-chlorophenyl)-N-(5-{[3-(cyclohexylamino)propyl]amino}-1,3,4-thiadiazol-2-yl)-2-propenamide,
226) N-(5-{[3-(cyclohexylamino)propyl]amino}-1,3,4-thiadiazol-2-yl)-2-ethoxy-1-naphthamide,
227) (E)-N-(5-{[3-(cyclohexylamino)propyl]amino}-1,3,4-thiadiazol-2-yl)-9-octadecenamide,
228) 2,6-dichloro-N-(5-{[3-(cyclohexylamino)propyl]amino}-1,3,4-thiadiazol-2-yl)benzamide,
229) 3,4-dichloro-N-(5-{[3-(cyclohexylamino)propyl]amino}-1,3,4-thiadiazol-2-yl)benzamide,
230) N-(5-{[3-(cyclohexylamino)propyl]amino}-1,3,4-thiadiazol-2-yl)-4-(trifluoromethyl)benzamide,
231) (E)-N-(5-{[3-(cyclohexylamino)propyl]amino}-1,3,4-thiadiazol-2-yl)-3-phenyl-2-propenamide,
232) N-(5-{[3-(cyclohexylamino)propyl]amino}-1,3,4-thiadiazol-2-yl)-4-iodobenzamide,
233) N-(5-{[3-(cyclohexylamino)propyl]amino}-1,3,4-thiadiazol-2-yl)-1,3-dioxo-1,3-dihydro-2-benzofuran-5-carboxamide,
234) 4-{[(5-{[3-(cyclohexylamino)propyl]amino}-1,3,4-thiadiazol-2-yl)amino]carbonyl}benzenesulfonyl fluoride,
235) N-(5-{[3-(cyclohexylamino)propyl]amino}-1,3,4-thiadiazol-2-yl)-2,4,6-triisopropylbenzamide,
236) N-(5-{[3-(cyclohexylamino)propyl]amino}-1,3,4-thiadiazol-2-yl)-5-nitro-2-furamide,
237) N-(5-{[3-(cyclohexylamino)propyl]amino}-1,3,4-thiadiazol-2-yl)-1-benzothiophene-2-carboxamide,
238) N-{5-[(3,4-dichlorobenzyl)amino]-1,3,4-thiadiazol-2-yl}-2,4-difluorobenzamide,
239) N-{5-[(3,4-dichlorobenzyl)amino]-1,3,4-thiadiazol-2-yl}-2-methoxybenzamide,
240) 4-cyano-N-{5-[(3,4-dichlorobenzyl)amino]-1,3,4-thiadiazol-2-yl}benzamide,
241) N-{5-[(3,4-dichlorobenzyl)amino]-1,3,4-thiadiazol-2-yl}-3-nitrobenzamide,
242) N-{5-[(3,4-dichlorobenzyl)amino]-1,3,4-thiadiazol-2-yl}-2-ethoxy-1-naphthamide,
243) (E)-N-{5-[(3,4-dichlorobenzyl)amino]-1,3,4-thiadiazol-2-yl}-9-octadecenamide,
244) 2,6-dichloro-N-{5-[(3,4-dichlorobenzyl)amino]-1,3,4-thiadiazol-2-yl}benzamide,
245) (E)-N-{5-[(3,4-dichlorobenzyl)amino]-1,3,4-thiadiazol-2-yl}-3-phenyl-2-propenamide,
246) N-{5-[(3,4-dichlorobenzyl)amino]-1,3,4-thiadiazol-2-yl}-1,3-dioxo-1,3-dihydro-2-benzofuran-5-carboxamide,
247) N-{5-[(3,4-dichlorobenzyl)amino]-1,3,4-thiadiazol-2-yl}-5-nitro-2-furamide,
248) 4-cyano-N-{5-[(3,4-dimethoxybenzyl)amino]-1,3,4-thiadiazol-2-yl}benzamide,
249) N-{5-[(3,4-dimethoxybenzyl)amino]-1,3,4-thiadiazol-2-yl}-3-nitrobenzamide,
250) N-{5-[(3,4-dimethoxybenzyl)amino]-1,3,4-thiadiazol-2-yl}-2-ethoxy-1-naphthamide,
251) (E)-N-{5-[(3,4-dimethoxybenzyl)amino]-1,3,4-thiadiazol-2-yl}-9-octadecenamide,
252) 2,6-dichloro-N-{5-[(3,4-dimethoxybenzyl)amino]-1,3,4-thiadiazol-2-yl}benzamide,
253) N-{5-[(3,4-dimethoxybenzyl)amino]-1,3,4-thiadiazol-2-yl}-4-iodobenzamide,
254) N-{5-[(3,4-dimethoxybenzyl)amino]-1,3,4-thiadiazol-2-yl}-1,3-dioxo-1,3-dihydro-2-benzofuran-5-carboxamide,
255) 2,4-difluoro-N-{5-[(4-phenylbutyl)amino]-1,3,4-thiadiazol-2-yl}benzamide,
256) 2-methoxy-N-{5-[(4-phenylbutyl)amino]-1,3,4-thiadiazol-2-yl}benzamide,
257) 4-bromo-N-{5-[(4-phenylbutyl)amino]-1,3,4-thiadiazol-2-yl}benzamide,
258) 4-methyl-N-{5-[(4-phenylbutyl)amino]-1,3,4-thiadiazol-2-yl}benzamide,
259) 5-chloro-N-{5-[(4-phenylbutyl)amino]-1,3,4-thiadiazol-2-yl}pentanamide,
260) 4-cyano-N-{5-[(4-phenylbutyl)amino]-1,3,4-thiadiazol-2-yl}benzamide,
261) 3-nitro-N-{5-[(4-phenylbutyl)amino]-1,3,4-thiadiazol-2-yl}benzamide,
262) 3,5-difluoro-N-{5-[(4-phenylbutyl)amino]-1,3,4-thiadiazol-2-yl}benzamide,
263) (E)-3-(2-chlorophenyl)-N-{5-[(4-phenylbutyl)amino]-1,3,4-thiadiazol-2-yl}-2-propenamide,
264) 2-ethoxy-N-{5-[(4-phenylbutyl)amino]-1,3,4-thiadiazol-2-yl}-1-naphthamide, 265) (E)-N-{5-[(4-phenylbutyl)amino]-1,3,4-thiadiazol-2-yl}-9-octadecenamide,
266) 2,6-dichloro-N-{5-[(4-phenylbutyl)amino]-1,3,4-thiadiazol-2-yl}benzamide,
267) 3,4-dichloro-N-{5-[(4-phenylbutyl)amino]-1,3,4-thiadiazol-2-yl}benzamide,
268) N-{5-[(4-phenylbutyl)amino]-1,3,4-thiadiazol-2-yl}-4-(trifluoromethyl) benzamide,
269) (E)-3-phenyl-N-{5-[(4-phenylbutyl)amino]-1,3,4-thiadiazol-2-yl}-2-propenamide,
270) 4-iodo-N-{5-[(4-phenylbutyl)amino]-1,3,4-thiadiazol-2-yl}benzamide,
271) 1,3-dioxo-N-{5-[(4-phenylbutyl)amino]-1,3,4-thiadiazol-2-yl}-1,3-dihydro-2-benzofuran-5-carboxamide,
272) 4-[({5-[(4-phenylbutyl)amino]-1,3,4-thiadiazol-2-yl}amino)carbonyl]benzenesulfonyl fluoride,
273) 2,4,6-triisopropyl-N-{5-[(4-phenylbutyl)amino]-1,3,4-thiadiazol-2-yl}benzamide,
274) 5-nitro-N-{5-[(4-phenylbutyl)amino]-1,3,4-thiadiazol-2-yl}-2-furamide,
275) N-{5-[(4-phenylbutyl)amino]-1,3,4-thiadiazol-2-yl}-1-benzothiophene-2-carboxamide,
276) N-{5-[(2,2-diphenylethyl)amino]-1,3,4-thiadiazol-2-yl}-2,4-difluorobenzamide,
277) N-{5-[(2,2-diphenylethyl)amino]-1,3,4-thiadiazol-2-yl}-2-methoxybenzamide,
278) 4-bromo-N-{5-[(2,2-diphenylethyl)amino]-1,3,4-thiadiazol-2-yl}benzamide,
279) 5-chloro-N-{5-[(2,2-diphenylethyl)amino]-1,3,4-thiadiazol-2-yl}pentanamide,
280) 4-cyano-N-{5-[(2,2-diphenylethyl)amino]-1,3,4-thiadiazol-2-yl}benzamide,
281) N-{5-[(2,2-diphenylethyl)amino]-1,3,4-thiadiazol-2-yl}-3,5-difluorobenzamide,
282) (E)-3-(2-chlorophenyl)-N-{5-[(2,2-diphenylethyl)amino]-1,3,4-thiadiazol-2-yl}-2-propenamide,
283) N-{5-[(2,2-diphenylethyl)amino]-1,3,4-thiadiazol-2-yl}-2-ethoxy-1-naphthamide,
284) (E)-N-{5-[(2,2-diphenylethyl)amino]-1,3,4-thiadiazol-2-yl}-9-octadecenamide,
285) 2,6-dichloro-N-{5-[(2,2-diphenylethyl)amino]-1,3,4-thiadiazol-2-yl}benzamide,
286) N-{5-[(2,2-diphenylethyl)amino]-1,3,4-thiadiazol-2-yl}-1,3-dioxo-1,3-dihydro-2-benzofuran-5-carboxamide,
287) 4-[({5-[(2,2-diphenylethyl)amino]-1,3,4-thiadiazol-2-yl}amino)carbonyl]benzenesulfonyl fluoride,
288) N-{5-[(2,2-diphenylethyl)amino]-1,3,4-thiadiazol-2-yl}-2,4,6-triisopropyl benzamide,
289) N-{5-[(2,2-diphenylethyl)amino]-1,3,4-thiadiazol-2-yl}-5-nitro-2-furamide,
290) N-{5-[(2,2-diphenylethyl)amino]-1,3,4-thiadiazol-2-yl}-1-benzothiophene-2-carboxamide,
291) 2,4-difluoro-N-[5-(undecylamino)-1,3,4-thiadiazol-2-yl]benzamide,
292) 4-bromo-N-[5-(undecylamino)-1,3,4-thiadiazol-2-yl]benzamide,
293) 4-methyl-N-[5-(undecylamino)-1,3,4-thiadiazol-2-yl]benzamide,
294) 5-chloro-N-[5-(undecylamino)-1,3,4-thiadiazol-2-yl]pentanamide,
295) 4-cyano-N-[5-(undecylamino)-1,3,4-thiadiazol-2-yl]benzamide,
296) 3-nitro-N-[5-(undecylamino)-1,3,4-thiadiazol-2-yl]benzamide,
297) 3,5-difluoro-N-[5-(undecylamino)-1,3,4-thiadiazol-2-yl]benzamide,
298) (E)-3-(2-chlorophenyl)-N-[5-(undecylamino)-1,3,4-thiadiazol-2-yl]-2-propenamide,
299) 2-ethoxy-N-[5-(undecylamino)-1,3,4-thiadiazol-2-yl]-1-naphthamide,
300) (E)-N-[5-(undecylamino)-1,3,4-thiadiazol-2-yl]-9-octadecenamide,
301) 2,6-dichloro-N-[5-(undecylamino)-1,3,4-thiadiazol-2-yl]benzamide,
302) 3,4-dichloro-N-[5-(undecylamino)-1,3,4-thiadiazol-2-yl]benzamide,
303) 4-(trifluoromethyl)-N-[5-(undecylamino)-1,3,4-thiadiazol-2-yl]benzamide,
304) (E)-3-phenyl-N-[5-(undecylamino)-1,3,4-thiadiazol-2-yl]-2-propenamide,
305) 4-iodo-N-[5-(undecylamino)-1,3,4-thiadiazol-2-yl]benzamide,
306) 1,3-dioxo-N-[5-(undecylamino)-1,3,4-thiadiazol-2-yl]-1,3-dihydro-2-benzofuran-5-carboxamide,
307) 4-({[5-(undecylamino)-1,3,4-thiadiazol-2-yl]amino}carbonyl)benzenesulfonyl fluoride,
308) 2,4,6-triisopropyl-N-[5-(undecylamino)-1,3,4-thiadiazol-2-yl]benzamide,
309) 5-nitro-N-[5-(undecylamino)-1,3,4-thiadiazol-2-yl]-2-furamide,
310) N-[5-(undecylamino)-1,3,4-thiadiazol-2-yl]-1-benzothiophene-2-carboxamide,
311) N-{5-[(3,3-diphenylpropyl)amino]-1,3,4-thiadiazol-2-yl}-2,4-difluorobenzamide,
312) N-{5-[(3,3-diphenylpropyl)amino]-1,3,4-thiadiazol-2-yl}-2-methoxybenzamide,
313) 4-bromo-N-{5-[(3,3-diphenylpropyl)amino]-1,3,4-thiadiazol-2-yl benzamide,
314) 5-chloro-N-{5-[(3,3-diphenylpropyl)amino]-1,3,4-thiadiazol-2-yl}pentanamide,
315) 4-cyano-N-{5-[(3,3-diphenylpropyl)amino]-1,3,4-thiadiazol-2-yl}benzamide,
316) N-{5-[(3,3-diphenylpropyl)amino]-1,3,4-thiadiazol-2-yl}-3-nitrobenzamide,
317) N-{5-[(3,3-diphenylpropyl)amino]-1,3,4-thiadiazol-2-yl}-3,5-difluorobenzamide,
318) (E)-3-(2-chlorophenyl)-N-{5-[(3,3-diphenylpropyl)amino]-1,3,4-thiadiazol-2-yl}-2-propenamide,
319) N-{5-[(3,3-diphenylpropyl)amino]-1,3,4-thiadiazol-2-yl}-2-ethoxy-1-naphthamide,
320) (E)-N-{5-[(3,3-diphenylpropyl)amino]-1,3,4-thiadiazol-2-yl}-9-octadecenamide,
321) 2,6-dichloro-N-{5-[(3,3-diphenylpropyl)amino]-1,3,4-thiadiazol-2-yl}benzamide,
322) N-{5-[(3,3-diphenylpropyl)amino]-1,3,4-thiadiazol-2-yl}-4-(trifluoromethyl) benzamide,
323) (E)-N-{5-[(3,3-diphenylpropyl)amino]-1,3,4-thiadiazol-2-yl}-3-phenyl-2-propenamide,
324) N-{5-[(3,3-diphenylpropyl)amino]-1,3,4-thiadiazol-2-yl}-4-iodobenzamide,
325) N-{5-[(3,3-diphenylpropyl)amino]-1,3,4-thiadiazol-2-yl}-1,3-dioxo-1,3-dihydro-2-benzofuran-5-carboxamide, 326) 4-[({5-[(3,3-diphenylpropyl)amino]-1,3,4-thiadiazol-2-yl}amino)carbonyl]benzenesulfonyl fluoride,
327) N-{5-[(3,3-diphenylpropyl)amino]-1,3,4-thiadiazol-2-yl}-2,4,6-triisopropylbenzamide,
328) N-{5-[(3,3-diphenylpropyl)amino]-1,3,4-thiadiazol-2-yl}-5-nitro-2-furamide,
329) N-{5-[(3,3-diphenylpropyl)amino]-1,3,4-thiadiazol-2-yl}-1-benzothiophene-2-carboxamide,
330) 2,4-difluoro-N-(5-{[2-(2-thienyl)ethyl]amino}-1,3,4-thiadiazol-2-yl)benzamide,
331) 4-cyano-N-(5-{[2-(2-thienyl)ethyl]amino}-1,3,4-thiadiazol-2-yl)benzamide,
332) 3-nitro-N-(5-{[2-(2-thienyl)ethyl]amino}-1,3,4-thiadiazol-2-yl)benzamide,
333) (E)-3-(2-chlorophenyl)-N-(5-{[2-(2-thienyl)ethyl]amino}-1,3,4-thiadiazol-2-yl)-2-propenamide,
334) 2-ethoxy-N-(5-{[2-(2-thienyl)ethyl]amino}-1,3,4-thiadiazol-2-yl)-1-naphthamide,
335) (E)-N-(5-{[2-(2-thienyl)ethyl]amino}-1,3,4-thiadiazol-2-yl)-9-octadecenamide,
336) 2,6-dichloro-N-(5-{[2-(2-thienyl)ethyl]amino}-1,3,4-thiadiazol-2-yl)benzamide,
337) (E)-3-phenyl-N-(5-{[2-(2-thienyl)ethyl]amino}-1,3,4-thiadiazol-2-yl)-2-propenamide,
338) 4-iodo-N-(5-{[2-(2-thienyl)ethyl]amino}-1,3,4-thiadiazol-2-yl)benzamide,
339) 1,3-dioxo-N-(5-{[2-(2-thienyl)ethyl]amino}-1,3,4-thiadiazol-2-yl)-1,3-dihydro-2-benzofuran-5-carboxamide,
340) 2,4,6-triisopropyl-N-(5-{[2-(2-thienyl)ethyl]amino}-1,3,4-thiadiazol-2-yl)benzamide,
341) N-(5-{[2-(2-thienyl)ethyl]amino-1,3,4-thiadiazol-2-yl)-1-benzothiophene-2-carboxamide,
342) (E)-N-(5-{[4-(aminosulfonyl)benzyl]amino}-1,3,4-thiadiazol-2-yl)-3-(2-chlorophenyl)-2-propenamide,
343) N-(5-[4-(aminosulfonyl)benzyl]amino}-1,3,4-thiadiazol-2-yl)-2-ethoxy-1-naphthamide,
344) (E)-N-(5-{[4-(aminosulfonyl)benzyl]amino}-1,3,4-thiadiazol-2-yl)-9-octadecenamide,
345) N-(5-{[4-(aminosulfonyl)benzyl]amino}-1,3,4-thiadiazol-2-yl)-2,6-dichlorobenzamide,
346) N-(5-{[4-(aminosulfonyl)benzyl]amino}-1,3,4-thiadiazol-2-yl)-3,4-dichlorobenzamide,
347) N-(5-{[4-(aminosulfonyl)benzyl]amino}-1,3,4-thiadiazol-2-yl)-4-(trifluoromethyl)benzamide,
348) (E)-N-(5-{[4-(aminosulfonyl)benzyl]amino}-1,3,4-thiadiazol-2-yl)-3-phenyl-2-propenamide,
349) N-(5-{[4-(aminosulfonyl)benzyl]amino}-1,3,4-thiadiazol-2-yl)-4-iodobenzamide,
350) N-(5-{[4-(aminosulfonyl)benzyl]amino}-1,3,4-thiadiazol-2-yl)-2,4,6-triisopropylbenzamide,
351) N-(5-{[4-(aminosulfonyl)benzyl]amino}-1,3,4-thiadiazol-2-yl)-1-benzothiophene-2-carboxamide,
352) (E)-3-(2-chlorophenyl)-N-(5-{[3-(4-methylpiperazino)propyl]amino}-1,3,4-thiadiazol-2-yl)-2-propenamide,
353) (E)-N-(5-{[3-(4-methylpiperazino)propyl]amino}-1,3,4-thiadiazol-2-yl)-9-octadecenamide,
354) 4-iodo-N-(5-{[3-(4-methylpiperazino)propyl]amino}-1,3,4-thiadiazol-2-yl)benzamide,
355) (E)-N-{5-[(2-cyanoethyl)amino]-1,3,4-thiadiazol-2-yl}-9-octadecenamide,
356) 2,6-dichloro-N-{5-[(2-cyanoethyl)amino]-1,3,4-thiadiazol-2-yl}benzamide,
357) N-{5-[(2-cyanoethyl)amino]-1,3,4-thiadiazol-2-yl}-2,4,6-triisopropylbenzamide,
358) 2,4-difluoro-N-(5-{[2-(phenylsulfanyl)ethyl]amino}-1,3,4-thiadiazol-2-yl)benzamide,
359) 4-bromo-N-(5-{[2-(phenylsulfanyl)ethyl]amino}-1,3,4-thiadiazol-2-yl)benzamide,
360) 5-chloro-N-(5-{[2-(phenylsulfanyl)ethyl]amino}-1,3,4-thiadiazol-2-yl)pentanamide,
361) (E)-3-(2-chlorophenyl)-N-(5-{[2-(phenylsulfanyl)ethyl]amino}-1,3,4-thiadiazol-2-yl)-2-propenamide,
362) 2-ethoxy-N-(5-{[2-(phenylsulfanyl)ethyl]amino}-1,3,4-thiadiazol-2-yl)-1-naphthamide,
363) (E)-N-(5-{[2-(phenylsulfanyl)ethyl]amino}-1,3,4-thiadiazol-2-yl)-9-octadecenamide,
364) (E)-3-phenyl-N-(5-{[2-(phenylsulfanyl)ethyl]amino}-1,3,4-thiadiazol-2-yl)-2-propenamide,
365) 4-iodo-N-(5-{[2-(phenylsulfanyl)ethyl]amino}-1,3,4-thiadiazol-2-yl)benzamide,
366) 1,3-dioxo-N-(5-{[2-(phenylsulfanyl)ethyl]amino}-1,3,4-thiadiazol-2-yl)-1,3-dihydro-2-benzofuran-5-carboxamide,
367) 4-cyano-N-{5-[(2-thienylmethyl)amino]-1,3,4-thiadiazol-2-yl}benzamide,
368) (E)-3-(2-chlorophenyl)-N-{5-[(2-thienylmethyl)amino]-1,3,4-thiadiazol-2-yl}-2-propenamide,
369) 2-ethoxy-N-{5-[(2-thienylmethyl)amino]-1,3,4-thiadiazol-2-yl}-1-naphthamide,
370) (E)-N-{5-[(2-thienylmethyl)amino]-1,3,4-thiadiazol-2-yl}-9-octadecenamide,
371) 2,6-dichloro-N-{5-[(2-thienylmethyl)amino]-1,3,4-thiadiazol-2-yl}benzamide,
372) 4-iodo-N-{5-[(2-thienylmethyl)amino]-1,3,4-thiadiazol-2-yl}benzamide,
373) 1,3-dioxo-N-{5-[(2-thienylmethyl)amino]-1,3,4-thiadiazol-2-yl}-1,3-dihydro-2-benzofuran-5-carboxamide,
374) 2,4,6-triisopropyl-N-{5-[(2-thienylmethyl)amino]-1,3,4-thiadiazol-2-yl}benzamide,
375) N-{5-[(2-thienylmethyl)amino]-1,3,4-thiadiazol-2-yl}-1-benzothiophene-2-carboxamide,
376) N-(5-{[2-(acetylamino)ethyl]amino}-1,3,4-thiadiazol-2-yl)-2-ethoxy-1-naphthamide,
377) (E)-N-(5-{[2-(acetylamino)ethyl]amino}-1,3,4-thiadiazol-2-yl)-9-octadecenamide,
378) (E)-N-(5-{[2-(acetylamino)ethyl]amino}-1,3,4-thiadiazol-2-yl)-3-phenyl-2-propenamide,
379) N-(5-{[2-(acetylamino)ethyl]amino}-1,3,4-thiadiazol-2-yl)-1,3-dioxo-1,3-dihydro-2-benzofuran-5-carboxamide,
380) N-(5-{[2-(acetylamino)ethyl]amino}-1,3,4-thiadiazol-2-yl)-2,4,6-triisopropylbenzamide,
381) N-(5-{[2-(acetylamino)ethyl]amino}-1,3,4-thiadiazol-2-yl)-1-benzothiophene-2-carboxamide,
382) 4-bromo-N-(5-{[3-(1H-imidazol-1-yl)propyl]amino}-1,3,4-thiadiazol-2-yl)benzamide,
383) (E)-3-(2-chlorophenyl)-N-(5-{[3-(1H-imidazol-1-yl)propyl]amino}-1,3,4-thiadiazol-2-yl)-2-propenamide,
384) 2-ethoxy-N-(5-{[3-(1H-imidazol-1-yl)propyl]amino}-1,3,4-thiadiazol-2-yl)-1-naphthamide, 385) (E)-N-(5-{[3-(1H-imidazol-1-yl)propyl]amino}-1,3,4-thiadiazol-2-yl)-9-octadecenamide, 386) 2,6-dichloro-N-(5-{[3-(1H-imidazol-1-yl)propyl]amino}-1,3,4-thiadiazol-2-yl)benzamide, 387) 3,4-dichloro-N-(5-{[3-(1H-imidazol-1-yl)propyl]amino}-1,3,4-thiadiazol-2-yl)benzamide, 388) (E)-N-(5-{[3-(1H-imidazol-1-yl)propyl]amino}-1,3,4-thiadiazol-2-yl)-3-phenyl-2-propenamide, 389) N-(5-{[3-(1H-imidazol-1-yl)propyl]amino}-1,3,4-thiadiazol-2-yl)-4-iodobenzamide, 390) N-(5-{[3-(1H-imidazol-1-yl)propyl]amino}-1,3,4-thiadiazol-2-yl)-2,4,6-triisopropylbenzamide, 391) tert-butyl 3-[(5-{[(E)-3-(2-chlorophenyl)-2-propenoyl]amino}-1,3,4-thiadiazol-2-yl)amino]propanoate, 392) tert-butyl 3-[(5-{[(2-ethoxy-1-naphthyl)carbonyl]amino}-1,3,4-thiadiazol-2-yl)amino]propanoate, 393) tert-butyl 3-({5-[(E)-9-octadecenoylamino]-1,3,4-thiadiazol-2-yl}amino)propanoate, 394) tert-butyl 3-({5-[(2,6-dichlorobenzoyl)amino]-1,3,4-thiadiazol-2-yl}amino)propanoate, 395) tert-butyl 3-({5-[(3,4-dichlorobenzoyl)amino]-1,3,4-thiadiazol-2-yl}amino)propanoate, 396) tert-butyl 3-[(5-{[4-(trifluoromethyl)benzoyl]amino}-1,3,4-thiadiazol-2-yl)amino]propanoate, 397) tert-butyl 3-[(5-1-[(E)-3-phenyl-2-propenoyl]amino}-1,3,4-thiadiazol-2-yl)amino]propanoate, 398) tert-butyl 3-[(5-{[(1,3-dioxo-1,3-dihydro-2-benzofuran-5-yl)carbonyl]amino}-1,3,4-thiadiazol-2-yl)amino]propanoate, 399) tert-butyl 3-({5-[(2,4,6-triisopropylbenzoyl)amino]-1,3,4-thiadiazol-2-yl}amino)propanoate, 400) (E)-3-(2-chlorophenyl)-N-[5-(cyclopropylamino)-1,3,4-thiadiazol-2-yl]-2-propenamide, 401) N-[5-(cyclopropylamino)-1,3,4-thiadiazol-2-yl]-2-ethoxy-1-naphthamide, 402) (E)-N-[5-(cyclopropylamino)-1,3,4-thiadiazol-2-yl]-9-octadecenamide, 403) (E)-N-[5-(cyclopropylamino)-1,3,4-thiadiazol-2-yl]-3-phenyl-2-propenamide, 404) N-[5-(cyclopropylamino)-1,3,4-thiadiazol-2-yl]-1-benzothiophene-2-carboxamide, 405) (E)-3-(2-chlorophenyl)-N-{5-[(cyclopropylmethyl)amino]-1,3,4-thiadiazol-2-yl}-2-propenamide, 406) N-{5-[(cyclopropylmethyl)amino]-1,3,4-thiadiazol-2-yl}-2-ethoxy-1-naphthamide, 407) (E)-N-{5-[(cyclopropylmethyl)amino]-1,3,4-thiadiazol-2-yl}-9-octadecenamide, 408) N-{5-[(cyclopropylmethyl)amino]-1,3,4-thiadiazol-2-yl}-4-iodobenzamide, 409) (E)-3-(2-chlorophenyl)-N-(5-{[2-(1H-imidazol-4-yl)ethyl]amino}-1,3,4-thiadiazol-2-yl)-2-propenamide, 410) 2-ethoxy-N-(5-{[2-(1H-imidazol-4-yl)ethyl]amino}-1,3,4-thiadiazol-2-yl)-1-naphthamide, 411) (E)-N-(5-{[2-(1H-imidazol-4-yl)ethyl]amino}-1,3,4-thiadiazol-2-yl)-9-octadecenamide, 412) 2,6-dichloro-N-(5-{[2-(1H-imidazol-4-yl)ethyl]amino}-1,3,4-thiadiazol-2-yl)benzamide, 413) (E)-N-(5-{[2-(1H-imidazol-4-yl)ethyl]amino}-1,3,4-thiadiazol-2-yl)-3-phenyl-2-propenamide, 414) N-(5-{[2-(1H-imidazol-4-yl)ethyl]amino}-1,3,4-thiadiazol-2-yl)-4-iodobenzamide, 415) N-(5-{[2-(1H-imidazol-4-yl)ethyl]amino}-1,3,4-thiadiazol-2-yl)-2,4,6-triisopropylbenzamide, 415) N-(5-{[2-(1H-imidazol-4-yl)ethyl]amino}-1,3,4-thiadiazol-2-yl)-1-benzothiophene-2-carboxamide, 416) 4-bromo-N-(5-{[2-(ethylsulfanyl)ethyl]amino}-1,3,4-thiadiazol-2-yl)benzamide, 417) (E)-3-(2-chlorophenyl)-N-(5-{[2-(ethylsulfanyl)ethyl]amino}-1,3,4-thiadiazol-2-yl)-2-propenamide, 418) 2-ethoxy-N-(5-{[2-(ethylsulfanyl)ethyl]amino}-1,3,4-thiadiazol-2-yl)-1-naphthamide, 419) (E)-N-(5-{[2-(ethylsulfanyl)ethyl]amino}-1,3,4-thiadiazol-2-yl)-9-octadecenamide, 420) 2,6-dichloro-N-(5-{[2-(ethylsulfanyl)ethyl]amino}-1,3,4-thiadiazol-2-yl)benzamide, 421) 3,4-dichloro-N-(5-{[2-(ethylsulfanyl)ethyl]amino}-1,3,4-thiadiazol-2-yl)benzamide, 422) N-(5-{[2-(ethylsulfanyl)ethyl]amino}-1,3,4-thiadiazol-2-yl)-4(trifluoromethyl)benzamide, 423) (E)-N-(5-{[2-(ethylsulfanyl)ethyl]amino}-1,3,4-thiadiazol-2-yl)-3-phenyl-2-propenamide, 424) N-(5-{[2-(ethylsulfanyl)ethyl]amino}-1,3,4-thiadiazol-2-yl)-4-iodobenzamide, 425) N-(5-{[2-(ethylsulfanyl)ethyl]amino}-1,3,4-thiadiazol-2-yl)-1-benzothiophene-2-carboxamide, 426) (E)-3-(2-chlorophenyl)-N-[5-(cyclobutylamino)-1,3,4-thiadiazol-2-yl]-2-propenamide, 427) N-[5-(cyclobutylamino)-1,3,4-thiadiazol-2-yl]-2-ethoxy-1-naphthamide, 428) (E)-N-[5-(cyclobutylamino)-1,3,4-thiadiazol-2-yl]-9-octadecenamide, 429) (E)-N-(5-{[2-(1-methyl-2-pyrrolidinyl)ethyl]amino}-1,3,4-thiadiazol-2-yl)-9-octadecenamide, 430) 2,4,6-triisopropyl-N-(5-{[2-(1-methyl-2-pyrrolidinyl)ethyl]amino}-1,3,4-thiadiazol-2-yl)benzamide, 431) N-[5-(2,3-dihydro-1H-inden-1-ylamino)-1,3,4-thiadiazol-2-yl]-3-nitrobenzamide, 432) N-[5-(2,3-dihydro-1H-inden-1-ylamino)-1,3,4-thiadiazol-2-yl]-2-ethoxy-1-naphthamide, 433) (E)-N-[5-(2,3-dihydro-1H-inden-1-ylamino)-1,3,4-thiadiazol-2-yl]-9-octadecenamide, 434) 2,6-dichloro-N-[5-(2,3-dihydro-1H-inden-1-ylamino)-1,3,4-thiadiazol-2-yl]benzamide, 435) N-[5-(2,3-dihydro-1H-inden-1-ylamino)-1,3,4-thiadiazol-2-yl]-1,3-dioxo-1,3-dihydro-2-benzofuran-5-carboxamide, 436) N-[5-(2,3-dihydro-1H-inden-1-ylamino)-1,3,4-thiadiazol-2-yl]-5-nitro-2-furamide, 437) (E)-3-(2-chlorophenyl)-N-[5-(neopentylamino)-1,3,4-thiadiazol-2-yl]-2-propenamide, 438) 2-ethoxy-N-[5-(neopentylamino)-1,3,4-thiadiazol-2-yl]-1-naphthamide, 439) 2,6-dichloro-N-[5-(neopentylamino)-1,3,4-thiadiazol-2-yl]benzamide, 440) 2-methoxy-N-[5-(1,2,3,4-tetrahydro-1-naphthalenylamino)-1,3,4-thiadiazol-2-yl]benzamide, 441) 3-nitro-N-[5-(1,2,3,4-tetrahydro-1-naphthalenylamino)-1,3,4-thiadiazol-2-yl]benzamide, 442) 3,5-difluoro-N-[5-(1,2,3,4-tetrahydro-1-naphthalenylamino)-1,3,4-thiadiazol-2-yl]benzamide, 443) (E)-3-(2-chlorophenyl)-N-[5-(1,2,3,4-tetrahydro-1-naphthalenylamino)-1,3,4-thiadiazol-2-yl]-2-propenamide, 444) 2-ethoxy-N-[5-(1,2,3,4-tetrahydro-1-naphthalenylamino)-1,3,4-thiadiazol-2-yl]-1-naphthamide,
445) (E)-N-[5-(1,2,3,4-tetrahydro-1-naphthalenylamino)-1,3,4-thiadiazol-2-yl]-9-octadecenamide,
446) 2,6-dichloro-N-[5-(1,2,3,4-tetrahydro-1-naphthalenylamino)-1,3,4-thiadiazol-2-yl]benzamide,
447) 1,3-dioxo-N-[5-(1,2,3,4-tetrahydro-1-naphthalenylamino)-1,3,4-thiadiazol-2-yl]-1,3-dihydro-2-benzofuran-5-carboxamide,
448) 5-nitro-N-[5-(1,2,3,4-tetrahydro-1-naphthalenylamino)-1,3,4-thiadiazol-2-yl]-2-furamide,
449) N-[5-(1,2,3,4-tetrahydro-1-naphthalenylamino)-1,3,4-thiadiazol-2-yl]-1-benzothiophene-2-carboxamide,
450) ethyl 4-[(5-{[(E)-3-(2-chlorophenyl)-2-propenoyl]amino}-1,3,4-thiadiazol-2-yl)amino]tetrahydro-1(2H)-pyridinecarboxylate,
451) ethyl 4-[(5-{[(2-ethoxy-1-naphthyl)carbonyl]amino}-1,3,4-thiadiazol-2-yl)amino]tetrahydro-1(2H)-pyridinecarboxylate,
452) ethyl 4-({5-[(E)-9-octadecenoylamino]-1,3,4-thiadiazol-2-yl}amino)tetrahydro-1(2H)-pyridinecarboxylate,
453) ethyl 4-({5-[(2,6-dichlorobenzoyl)amino]-1,3,4-thiadiazol-2-yl}amino)tetrahydro-1(2H)-pyridinecarboxylate,
454) ethyl 4-({5-[(1-benzothiophen-2-ylcarbonyl)amino]-1,3,4-thiadiazol-2-yl}amino)tetrahydro-1(2H)-pyridinecarboxylate,
455) N-{5-[(1-benzyl-4-piperidinyl)amino]-1,3,4-thiadiazol-2-yl}-4-bromobenzamide,
456) (E)-N-{5-[(1-benzyl-4-piperidinyl)amino]-1,3,4-thiadiazol-2-yl}-3-(2-chlorophenyl)-2-propenamide,
457) N-{5-[(1-benzyl-4-piperidinyl)amino]-1,3,4-thiadiazol-2-yl}-2-ethoxy-1-naphthamide,
458) (E)-N-{5-[(1-benzyl-4-piperidinyl)amino]-1,3,4-thiadiazol-2-yl}-9-octadecenamide,
459) N-{5-[(1-benzyl-4-piperidinyl)amino]-1,3,4-thiadiazol-2-yl}-2,6-dichlorobenzamide,
460) (E)-N-{5-[(1-benzyl-4-piperidinyl)amino]-1,3,4-thiadiazol-2-yl}-3-phenyl-2-propenamide,
461) N-{5-[(1-benzyl-4-piperidinyl)amino]-1,3,4-thiadiazol-2-yl}-4-iodobenzamide,
462) N-{5-[(1-benzyl-4-piperidinyl)amino]-1,3,4-thiadiazol-2-yl}-1,3-dioxo-1,3-dihydro-2-benzofuran-5-carboxamide,
463) 4-[({5-[(1-benzyl-4-piperidinyl)amino]-1,3,4-thiadiazol-2- yl}amino)carbonyl]benzenesulfonyl fluoride,
464) N-{5-[(1-benzyl-4-piperidinyl)amino]-1,3,4-thiadiazol-2-yl}-2,4,6-triisopropylbenzamide,
465) N-{5-[(1-benzyl-4-piperidinyl)amino]-1,3,4-thiadiazol-2-yl}-5-nitro-2-furamide,
466) N-{5-[(1-benzyl-4-piperidinyl)amino]-1,3,4-thiadiazol-2-yl}-1-benzothiophene-2-carboxamide,
467) (E)-N-(5-{[2-(dimethylamino)ethyl]amino}-1,3,4-thiadiazol-2-yl)-9-octadecenamide, or
468) N-(5-{[2-(dimethylamino)ethyl]amino}-1,3,4-thiadiazol-2-yl)-2,4,6-triisopropylbenzamide.

8. A compound of claim 1 which is
1) N-(5-{[3-(cyclohexylamino)propyl]amino}-1,3,4-thiadiazol-2-yl)-2-ethoxy-1-naphthamide,
2) N-(5-{[3-(cyclohexylamino)propyl]amino}-1,3,4-thiadiazol-2-yl)-1,3-dioxo-1,3-dihydro-2-benzofuran-5-carboxamide,
3) N-{5-[(3,3-diphenylpropyl)amino]-1,3,4-thiadiazol-2-yl}-1,3-dioxo-1,3-dihydro-2-benzofuran-5-carboxamide,
4) N-{5-[(2,2-diphenylethyl)amino]-1,3,4-thiadiazol-2-yl}-1,3-dioxo-1,3-dihydro-2-benzofuran-5-carboxamide,
5) 1,3-dioxo-N-[5-(undecylamino)-1,3,4-thiadiazol-2-yl]-1,3-dihydro-2-benzofuran-5-carboxamide,
6) N-[5-({[(2R)-6,6-dimethylbicyclo[3.1.1]hept-2-yl]methyl}amino)-1,3,4-thiadiazol-2-yl]-1,3-dioxo-1,3-dihydro-2-benzofuran-5-carboxamide,
7) 1,3-dioxo-N-{5-[(4-phenylbutyl)amino]-1,3,4-thiadiazol-2-yl}-1,3-dihydro-2-benzofuran-5-carboxamide,
8) N-(5-{[2-(1H-indol-3-yl)ethyl]amino}-1,3,4-thiadiazol-2-yl)-1,3-dioxo-1,3-dihydro-2-benzofuran-5-carboxamide,
9) (E)-N-(5-{[3-(cyclohexylamino)propyl]amino}-1,3,4-thiadiazol-2-yl)-9-octadecenamide,
10) 2-ethoxy-N-(5-{[2-(1H-indol-3-yl)ethyl]amino}-1,3,4-thiadiazol-2-yl)-1-naphthamide,
11) 2,6-dichloro-N-(5-{[3-(cyclohexylamino)propyl]amino}-1,3,4-thiadiazol-2-yl)benzamide,
12) N-[5-(cycloheptylamino)-1,3,4-thiadiazol-2-yl]-2-ethoxy-1-naphthamide,
13) N-[5-({[(2R)-6,6-dimethylbicyclo[3.1.1]hept-2-yl]methyl}amino)-1,3,4-thiadiazol-2-yl]-2-ethoxy-1-naphthamide,
14) (E)-N-(5-{[4-(aminosulfonyl)benzyl]amino}-1,3,4-thiadiazol-2-yl)-9-octadecenamide,
15) N-{5-[(2,2-diphenylethyl)amino]-1,3,4-thiadiazol-2-yl}-2-ethoxy-1-naphthamide,
16) (E)-N-(5-{[3-(cyclohexylamino)propyl]amino}-1,3,4-thiadiazol-2-yl)-3-phenyl-2-propenamide,
17) 2,6-dichloro-N-{5-[(3,3-diphenylpropyl)amino]-1,3,4-thiadiazol-2-yl}benzamide,
18) 2,6-dichloro-N-{5-[(2,2-diphenylethyl)amino]-1,3,4-thiadiazol-2-yl}benzamide,
19) (E)-N-{5-[(1,3-benzodioxol-5-ylmethyl)amino]-1,3,4-thiadiazol-2-yl}-9-octadecenamide,
20) N-(5-{[4-(aminosulfonyl)benzyl]amino}-1,3,4-thiadiazol-2-yl)-2,6-dichlorobenzamide,
21) 2,6-dichloro-N-(5-{[2-(1H-indol-3-yl)ethyl]amino}-1,3,4-thiadiazol-2-yl)benzamide,
22) 4-cyano-N-{5-[(2,2-diphenylethyl)amino]-1,3,4-thiadiazol-2-yl}benzamide,
23) N-{5-[(1,3-benzodioxol-5-ylmethyl)amino]-1,3,4-thiadiazol-2-yl}-1,3-dioxo-1,3-dihydro-2-benzofuran-5-carboxamide,
24) 4-cyano-N-(5-{[3-(cyclohexylamino)propyl]amino}-1,3,4-thiadiazol-2-yl)benzamide,
25) N-(5-{[2-(1H-indol-3-yl)ethyl]amino}-1,3,4-thiadiazol-2-yl)-5-nitro-2-furamide,
26) 2,6-dichloro-N-[5-{[(2R)-6,6-dimethylbicyclo[3.1.1]hept-2-yl]methyl}amino)-1,3,4-thiadiazol-2-yl]benzamide,
27) 4-cyano-N-(5-{[2-(1H-indol-3-yl)ethyl]amino}-1,3,4-thiadiazol-2-yl)benzamide,
28) N-[5-(cycloheptylamino)-1,3,4-thiadiazol-2-yl]-1,3-dioxo-1,3-dihydro-2-benzofuran-5-carboxamide, 29) N-{5-[(1,3-benzodioxol-5-ylmethyl)amino]-1,3,4-thiadiazol-2-yl}-2,6dichlorobenzamide, 30) N-{5-[(2,2-diphenylethyl)amino]-1,3,4-thiadiazol-2-yl}-2-methoxybenzamide, 31) (E)-N-(5-{[4-(aminosulfonyl)benzyl]amino}-1,3,4-thiadiazol-2-yl)-3-phenyl-2-propenamide, 32) (E)-N-[5-({[(2R)-6,6-dimethylbicyclo[3.1.1]hept-2-yl]methyl}amino)-1,3,4-thiadiazol-2-yl]-9-octadecenamide, 33) (E)-N-(5-{[2-(1H-indol-3-yl)ethyl]amino}-1,3,4-thiadiazol-2-yl)-9-octadecenamide, 34) (E)-N-[5-(cycloheptylamino)-1,3,4-thiadiazol-2-yl]-9-octadecenamide, 35) (E)-N-{5-[(4-fluorobenzyl)amino]-1,3,4-thiadiazol-2-yl}-9-octadecenamide, 36) 2,6-dichloro-N-{5-[(4-phenylbutyl)amino]-1,3,4-thiadiazol-2-yl}benzamide, or 37) N-(5-{[4-(aminosulfonyl)benzyl]amino}-1,3,4-thiadiazol-2-yl)-2-ethoxy-1-naphthamide.

9. A compound of claim 1 which is

1) N-(5-{[3-(cyclohexylamino)propyl]amino}-1,3,4-thiadiazol-2-yl)-2-ethoxy-1-naphthamide, 2) N-(5-{[3-(cyclohexylamino)propyl]amino}-1,3,4-thiadiazol-2-yl)-1,3-dioxo-1,3-dihydro-2-benzofuran-5-carboxamide, 3) N-{5-[(3,3-diphenylpropyl)amino]-1,3,4-thiadiazol-2-yl}-1,3-dioxo-1,3-dihydro-2-benzofuran-5-carboxamide, 4) N-{5-[(2,2-diphenylethyl)amino]-1,3,4-thiadiazol-2-yl}-1,3-dioxo-1,3-dihydro-2-benzofuran-5-carboxamide, 5) 1,3-dioxo-N-[5-(undecylamino)-1,3,4-thiadiazol-2-yl]-1,3-dihydro-2-benzofuran-5-carboxamide, 6) N-[5-({[(2R)-6,6-dimethylbicyclo[3.1.1]hept-2-yl]methyl}amino)-1,3,4-thiadiazol-2-yl]-1,3-dioxo-1,3-dihydro-2-benzofuran-5-carboxamide, 7) 1,3-dioxo-N-{5-[(4-phenylbutyl)amino]-1,3,4-thiadiazol-2-yl}-1,3-dihydro-2-benzofuran-5-carboxamide, 8) N-(5-{[2-(1H-indol-3-yl)ethyl]amino}-1,3,4-thiadiazol-2-yl)-1,3-dioxo-1,3-dihydro-2-benzofuran-5-carboxamide, or 9) (E)-N-(5-{[3-(cyclohexylamino)propyl]amino}-1,3,4-thiadiazol-2-yl)-9-octadecenamide.

10. A pharmaceutical composition which comprises an effective amount of the compound of claim 1 to treat cytomegalovirus infection and a pharmaceutically acceptable carrier.

11. A method for treating viral infections in a mammal comprising administering to said mammal in need thereof an effective amount of a compound of formula I of claim 1.

12. A method of claim 11 wherein said effective amount of a compound of formula is administered orally, parenterally or topically in a pharmaceutical composition.

13. A method of claim 11 wherein said viral infection is human cytomegalovirus infection.

14. A method of claim 11 wherein said effective amount of a compound of formula is administered in an amount of from about 0.1 to 300 mg/kg of mammal body weight.

* * * * *